(12) United States Patent
Sun et al.

(10) Patent No.: US 9,533,984 B2
(45) Date of Patent: Jan. 3, 2017

(54) BICYCLIC HETEROCYCLES AS FGFR INHIBITORS

(71) Applicants: Incyte Corporation, Wilmington, DE (US); Incyte Holdings Corporation, Wilmington, DE (US)

(72) Inventors: Yaping Sun, Hockessin, DE (US); Liang Lu, Hockessin, DE (US); Wenqing Yao, Chadds Ford, PA (US); Jincong Zhuo, Garnet Valley, PA (US); Liangxing Wu, Wilmington, PA (US); Meizhong Xu, Hockessin, DE (US); Ding-Quan Qian, Newark, DE (US); Chunhong He, Chadds Ford, PA (US); Fenglei Zhang, Ambler, PA (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

(21) Appl. No.: 14/256,438

(22) Filed: Apr. 18, 2014

(65) Prior Publication Data

US 2014/0315902 A1 Oct. 23, 2014

Related U.S. Application Data

(60) Provisional application No. 61/813,782, filed on Apr. 19, 2013.

(51) Int. Cl.
*C07D 471/04* (2006.01)
*A61P 35/00* (2006.01)
*A61K 31/4375* (2006.01)

(52) U.S. Cl.
CPC .................. *C07D 471/04* (2013.01)

(58) Field of Classification Search
CPC .................................. C07D 471/04
See application file for complete search history.

(56) References Cited

U.S. PATENT DOCUMENTS

| | | | |
|---|---|---|---|
| 850,370 | A | 4/1907 | Hynes |
| 3,894,021 | A | 7/1975 | Denzel et al. |
| 4,271,074 | A | 6/1981 | Lohmann et al. |
| 4,339,267 | A | 7/1982 | Levitt |
| 4,347,348 | A | 8/1982 | Chernikhov et al. |
| 4,402,878 | A | 9/1983 | D'Alelio et al. |
| 4,405,519 | A | 9/1983 | D'Alelio et al. |
| 4,405,520 | A | 9/1983 | D'Alelio et al. |
| 4,405,786 | A | 9/1983 | D'Alelio et al. |
| 4,460,773 | A | 7/1984 | Suzuki et al. |
| 4,874,803 | A | 10/1989 | Baron et al. |
| 4,940,705 | A | 7/1990 | Boshagen et al. |
| 5,159,054 | A | 10/1992 | Keller |
| 5,240,941 | A | 8/1993 | Bruneau |
| 5,480,887 | A | 1/1996 | Hornback et al. |
| 5,536,725 | A | 7/1996 | Cullen et al. |
| 5,541,324 | A | 7/1996 | TenBrink et al. |
| 5,783,577 | A | 7/1998 | Houghten et al. |
| 5,845,025 | A | 12/1998 | Garito et al. |
| 5,994,364 | A | 11/1999 | Njoroge et al. |
| 6,465,484 | B1 | 10/2002 | Bilodeau et al. |
| 6,998,408 | B2 | 2/2006 | Pinto |
| 7,074,801 | B1 | 7/2006 | Yoshida et al. |
| 7,125,880 | B1 | 10/2006 | Chen |
| 8,754,114 | B2 | 6/2014 | Yao et al. |
| 8,889,711 | B2 | 11/2014 | Bedjeguelal |
| 2003/0078255 | A1 | 4/2003 | Pinto |
| 2003/0078277 | A1 | 4/2003 | Hibi et al. |
| 2003/0181622 | A1 | 9/2003 | Chiu et al. |
| 2004/0044012 | A1 | 3/2004 | Dobrusin et al. |
| 2004/0067948 | A1 | 4/2004 | Hallett |
| 2004/0097493 | A1 | 5/2004 | Chen et al. |
| 2004/0122029 | A1 | 6/2004 | Liu et al. |
| 2004/0204427 | A1 | 10/2004 | Chen et al. |
| 2005/0070542 | A1 | 3/2005 | Hodgetts et al. |
| 2005/0148603 | A1 | 7/2005 | Jimenez et al. |
| 2005/0197340 | A1 | 9/2005 | Arora et al. |
| 2006/0222637 | A1 | 10/2006 | Bamdad |
| 2006/0270849 | A1 | 11/2006 | Nishino et al. |
| 2007/0116984 | A1 | 5/2007 | Park et al. |
| 2007/0197510 | A1 | 8/2007 | Ohmoto et al. |
| 2007/0280943 | A1 | 12/2007 | Friedman et al. |
| 2008/0249301 | A1 | 10/2008 | Hornberger et al. |
| 2009/0098086 | A1 | 4/2009 | Zask et al. |
| 2009/0099165 | A1 | 4/2009 | Hurley et al. |
| 2009/0099190 | A1 | 4/2009 | Flynn et al. |
| 2009/0105233 | A1 | 4/2009 | Chua et al. |
| 2009/0131467 | A1 | 5/2009 | Kanazawa et al. |
| 2009/0163545 | A1 | 6/2009 | Goldfarb |

(Continued)

FOREIGN PATENT DOCUMENTS

| | | |
|---|---|---|
| CN | 101007778 | 8/2007 |
| CN | 102399220 | 4/2012 |

(Continued)

OTHER PUBLICATIONS

International Preliminary Report on Patentability in International Application No. PCT/US2013/045309, mailed Dec. 24, 2014, 11 pages.
International Search Report dated Jun. 19, 2012 for International Appln. No. PCT/US2011/066473 (15 pgs.).
International Preliminary Report on Patentability and Written Opinion in International Application No. PCT/US2011/066473, issued Jun. 25, 2013, 10 pages.
International Search Report and Written Opinion in International Application No. PCT/US2013/054361, dated Oct. 16, 2013, 12 pages.
Invitation to Pay Additional Fees and, Where Applicable, Protest Fee in International Application No. PCT/US2013/045309, mailed Nov. 25, 2013, 5 pages.
International Search Report and Written Opinion in International Application No. PCT/US2013/045309, mailed on Jan. 22, 2014, 19 pages.
Berge et al., "Pharmaceutical Salts", Journal of Pharmaceutical Science, 66(2):1-19 (1977).
Blom et al., "Optimizing Preparative LC-MS Configurations and Methods for Parallel Synthesis Purification", *J. Combi Chem.*, 5, 670 (2003).

(Continued)

*Primary Examiner* — Susanna Moore
(74) *Attorney, Agent, or Firm* — Fish & Richardson P.C.

(57) ABSTRACT

The present invention relates to bicyclic heterocycles, and pharmaceutical compositions of the same, that are inhibitors of one or more FGFR enzymes and are useful in the treatment of FGFR-associated diseases such as cancer.

6 Claims, No Drawings

(56) References Cited

U.S. PATENT DOCUMENTS

| | | | |
|---|---|---|---|
| 2009/0246198 A1 | 10/2009 | Dong et al. |
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0210636 A1 | 8/2010 | Ishikawa et al. |
| 2010/0239496 A1 | 9/2010 | Gangadharmath et al. |
| 2011/0045511 A1 | 2/2011 | Graus Porta et al. |
| 2011/0159604 A1 | 6/2011 | Fan et al. |
| 2011/0160203 A1 | 6/2011 | Liu et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0338134 A1 | 12/2013 | Wu et al. |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0171405 A1 | 6/2014 | Zhuo et al. |
| 2014/0187559 A1 | 7/2014 | Miduturu |
| 2014/0243308 A1 | 8/2014 | Yao et al. |
| 2014/0296233 A1 | 10/2014 | Akullian et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Linnanen et al. |
| 2015/0011560 A1 | 1/2015 | Legeai-Mallet |
| 2015/0011579 A1 | 1/2015 | Clary-Ceccato et al. |
| 2015/0197519 A1 | 7/2015 | Bifulco |

FOREIGN PATENT DOCUMENTS

| | | |
|---|---|---|
| CN | 102399233 | 4/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S6310630 | 1/1988 |
| JP | 02009895 | 1/1990 |
| JP | H0348656 | 3/1991 |
| JP | H03275669 | 12/1991 |
| JP | 04179576 | 6/1992 |
| JP | H04158084 | 6/1992 |
| JP | H04328121 | 11/1992 |
| JP | H05320173 | 12/1993 |
| JP | H05320515 | 12/1993 |
| JP | H09188812 | 7/1997 |
| JP | H1060426 | 3/1998 |
| JP | H11171865 | 6/1999 |
| JP | 2000123973 | 4/2000 |
| JP | 2001265031 | 9/2001 |
| JP | 2002-296731 | 10/2002 |
| JP | 2003-335788 | 11/2003 |
| JP | 2004-203749 | 7/2004 |
| JP | 2004-346145 | 12/2004 |
| JP | 2005-15395 | 1/2005 |
| JP | 2005-320288 | 11/2005 |
| JP | 2006-28027 | 2/2006 |
| JP | 2006-284843 | 10/2006 |
| JP | 2006-316054 | 11/2006 |
| JP | 2008-198769 | 8/2008 |
| JP | 2010-180147 | 8/2010 |
| JP | 2010-248429 | 11/2010 |
| JP | 2010-267847 | 11/2010 |
| JP | 2010-270245 | 12/2010 |
| JP | 2010-272618 | 12/2010 |
| JP | 2010-272727 | 12/2010 |
| JP | 2010-278114 | 12/2010 |
| JP | 2011-9348 | 1/2011 |
| JP | 2011-44637 | 3/2011 |
| JP | 2011-116840 | 6/2011 |
| JP | 2011-222650 | 11/2011 |
| JP | 2012-116825 | 6/2012 |
| JP | 2012-136476 | 7/2012 |
| JP | 5120580 | 1/2013 |
| JP | 2013-49251 | 3/2013 |
| JP | 2013-179181 | 9/2013 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 2014009105 | 8/2014 |
| WO | WO 88/03025 | 5/1988 |
| WO | WO 91/09835 | 7/1991 |
| WO | WO 91/10172 | 7/1991 |
| WO | WO 92/06078 | 4/1992 |
| WO | WO 92/22552 | 12/1992 |
| WO | WO 93/24488 | 12/1993 |
| WO | WO 94/13669 | 6/1994 |
| WO | WO 94/15995 | 7/1994 |
| WO | WO 94/25438 | 11/1994 |
| WO | WO 95/20965 | 8/1995 |
| WO | WO 96/15128 | 5/1996 |
| WO | WO 96/40707 | 12/1996 |
| WO | WO 97/47601 | 12/1997 |
| WO | WO 98/05661 | 2/1998 |
| WO | WO 98/06703 | 2/1998 |
| WO | WO 98/11438 | 3/1998 |
| WO | WO 98/18781 | 5/1998 |
| WO | WO 98/28281 | 7/1998 |
| WO | WO 98/33798 | 8/1998 |
| WO | WO 98/46609 | 10/1998 |
| WO | WO 98/54156 | 12/1998 |
| WO | WO 99/06422 | 2/1999 |
| WO | WO 99/07732 | 2/1999 |
| WO | WO 99/09030 | 2/1999 |
| WO | WO 99/42442 | 8/1999 |
| WO | WO 99/59975 | 11/1999 |
| WO | WO 99/61444 | 12/1999 |
| WO | WO 99/64400 | 12/1999 |
| WO | WO 00/24744 | 5/2000 |
| WO | WO 00/68186 | 11/2000 |
| WO | WO 01/02369 | 1/2001 |
| WO | WO 01/22938 | 4/2001 |
| WO | WO 01/23386 | 4/2001 |
| WO | WO 01/29041 | 4/2001 |
| WO | WO 01/29042 | 4/2001 |
| WO | WO 01/42247 | 6/2001 |
| WO | WO 01/53273 | 7/2001 |
| WO | WO 01/55148 | 8/2001 |

(56) References Cited

FOREIGN PATENT DOCUMENTS

| | | |
|---|---|---|
| WO | WO 01/57037 | 8/2001 |
| WO | WO 01/57038 | 8/2001 |
| WO | WO 01/58899 | 8/2001 |
| WO | WO 01/66099 | 9/2001 |
| WO | WO 01/68647 | 9/2001 |
| WO | WO 01/83472 | 11/2001 |
| WO | WO 01/85722 | 11/2001 |
| WO | WO 02/00655 | 1/2002 |
| WO | WO 02/12442 | 2/2002 |
| WO | WO 02/14315 | 2/2002 |
| WO | WO 02/20011 | 3/2002 |
| WO | WO 02/055082 | 7/2002 |
| WO | WO 02/066481 | 8/2002 |
| WO | WO 02/074754 | 9/2002 |
| WO | WO 02/076953 | 10/2002 |
| WO | WO 02/088095 | 11/2002 |
| WO | WO 02/094825 | 11/2002 |
| WO | WO 02/096873 | 12/2002 |
| WO | WO 02/102793 | 12/2002 |
| WO | WO 03/000187 | 1/2003 |
| WO | WO 03/000688 | 1/2003 |
| WO | WO 03/000690 | 1/2003 |
| WO | WO 03/009852 | 2/2003 |
| WO | WO 03/014083 | 2/2003 |
| WO | WO 03/037891 | 5/2003 |
| WO | WO 03/040131 | 5/2003 |
| WO | WO 03/049542 | 6/2003 |
| WO | WO 03/062236 | 7/2003 |
| WO | WO 03/075836 | 9/2003 |
| WO | WO 03/082871 | 10/2003 |
| WO | WO 03/097609 | 11/2003 |
| WO | WO 03/099818 | 12/2003 |
| WO | WO 03/101985 | 12/2003 |
| WO | WO 2004/002986 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/048343 | 6/2004 |
| WO | WO 2004/052291 | 6/2004 |
| WO | WO 2004/052862 | 6/2004 |
| WO | WO 2004/056822 | 7/2004 |
| WO | WO 2004/056830 | 7/2004 |
| WO | WO 2004/065378 | 8/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/113307 | 12/2004 |
| WO | WO 2005/007653 | 1/2005 |
| WO | WO 2005/011597 | 2/2005 |
| WO | WO 2004/112793 | 3/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |

(56) References Cited

FOREIGN PATENT DOCUMENTS

| | | |
|---|---|---|
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/092181 | 8/2010 |
| WO | WO 2010/099938 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |

(56) References Cited

FOREIGN PATENT DOCUMENTS

| | | |
|---|---|---|
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |

(56) References Cited

FOREIGN PATENT DOCUMENTS

| WO | WO 2013/033981 | 3/2013 |
|---|---|---|
| WO | WO 2013/039854 | 3/2013 |
| WO | WO 2013/049352 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/108992 | 7/2015 |
| WO | WO 2016/064960 | 4/2016 |

OTHER PUBLICATIONS

Blom et al., Preparative LC-MS Purification: Improved Compound Specific Method Optimization, J. Combi. Chem. 2004, 6(6), 874-883.
Blom, K., "Two-Pump at Column Dilution Configuration for Preparative LC-MS", *J. Combi Chem*., 4, 295 (2002).
Chase et al., "Activity of TKI258 against primary cells and cell lines with FGFR1 fusion genes associated with the 8p11 myeloproliferative syndryome," Blood, 2007, 110:3729-3734.
Chesi et al., "Activated fibroblast growth factor receptor 3 is an oncogene that contributes to tumor progression in multiple myeloma," Blood, 2001, 97:729-736.
Cole et al., "Inhibition of FGFR2 and FGFR1 increases cisplatin sensitivity in ovarian cancer," Cancer Biol. Therapy, Sep. 1, 2010, 10(5):495-504.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dutt et al., "Drug-sensitive FGFR2 mutations in endometrial carcinoma," PNAS, Jun. 24, 2008, 105(25):8713-8717.
Eissa, "Synthesis and evaluation of some surface active agents from long chain fatty amine," Spanish National Research Council, Jan. 2007, 58(4):379-389.
Eswarakumar et al., "Cellular signaling by fibroblast growth factor receptors," Cytokine & Growth Factor Reviews, 2005, 16:139-149.
French et al., "Targeting FGFR4 Inhibits Hepatocellular Carcinoma in Preclinical Mouse Models," PLoS ONE, 2012, 7(5):e36713, 1-12.
Ghorab et al., "Synthesis of some sulfur containing Tetrahydrobenzoabuthieno[b] Thieno(Pyridines, Quinolines, Oxazines and Pyrimidines) as possible radioprotective and Antineoplastic agents," Phosphorus, Sulfur and Silicon, Jan. 1998, 134/135:57-76.
Greene, T. W. and Wuts, P. G. M., "Protective Groups in Organic Synthesis", 3rd Ed., Wiley & Sons, Inc., New York (1999).
Gu et al., "Phosphotyrosine profiling identifies the KG-1 cell line as a model for the study of FGFR1 fusions in acute myeloid leukemia," Blood, Dec. 15, 2006, 108(13):4202-42040.
Knights and Cook, "De-regulated FGF receptors as therapeutic targets in cancer," Pharmacology & Therapeutics, 2010, 125:105-117.
Koziczak et al., "Blocking of FGFR signaling inhibits breast cancer cell proliferation through downregulation of D-type cyclins," Oncogene, 2004, 23:3501-3508.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Lamont et al., "Small molecule FGF receptor inhibitors block FGFR-dependent urothelial carcinoma growth in vitro and in vivo," Br. J Cancer, 2011, 104:75-82.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Matsuda et al., "Fibroblast Growth Factor Receptor 2 IIIc as a Therapeutic Target for Colorectal Cancer Cells," Mol Cancer Ther., 2012, 52 pages.
McMahon, "VEGF Receptor Signaling in Tumor Angiogenesis," Oncologist, 2000, 5(suppl 1):3-10.
Metzner, "Fibroblast Growth Factor Receptors as Therapeutic Targets in Human Melanoma: Synergism with BRAF Inhibition," J Investigative Dermatol., 2011, 131:2087-2095.
Murphy et al., "Evidence for distinct alterations in the FGF axis in prostate cancer progression to an aggressive clinical phenotype," J Pathol., 2010, 220:452-460.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Pinedo and Slamon, "Translational Research: The Role of VEGF in Tumor Angiogenesis," Oncologist, 2000, 5(suppl 1):1-2.
Remington's Pharmaceutical Sciences, 17th ed., Mack Publishing Company, Easton, Pa., 1985, p. 1418.
Singh et al., "Transforming Fusions of FGFR and TACC Genes in Human Glioblastoma," Science, Sep. 2012, 337:1231-1235.
Turner and Grose, "Fibroblast growth factor signalling: from development to cancer," Nature Reviews Cancer, 2010, 10:116-129.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
"Sabiosciences.com" [online]. "FGF Pathway," 2000-2012, [retrieved on Jun. 23, 2015]. Retrieved from the Internet: URL <http://www.sabiosciences.com/pathway.php?sn=FGF_Signaling>, 3 pages.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.
Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.
Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.

(56) References Cited

OTHER PUBLICATIONS

Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Bergwitz and Juppner, "Regulation of Phosphate Homeostasis by PTH, Vitamin D, and FGF23," Annu. Rev. Med., 2010, 61:91-104.
Bhide et al., "Discovery and Preclinical Studies of (R)-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
BioCentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Bono et al., "Inhibition of Tumor Angiogenesis and Growth by a Small-Molecule Multi-FGF Receptor Blocker with Allosteric Properties," Cancer Cell, Apr. 2013, 477-488.
Brooks et al., "Fibroblast growth factor signaling: a new therapeutic opportunity in cancer," Clinical Cancer Research, 2012, 1-23.
Cappellen et al., "Frequent activating mutations of FGFR3 in human bladder and cervix carcinomas," Nature Genetics, Sep. 1999, 23: 18-20.
Carmichael et al., "Familial Tumoral Calcinosis: A Forty-Year Follow-up on One Family," The Journal of Bone & Joint Surgery, 2009, 664-671.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.
Chen et al., "FGFR3 as a therapeutic target of the small molecule inhibitor PKC412 in hematopoietic malignancies," Oncogene, 2005, 24: 8259-8267.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Coleman, "Positive and negative regulation of cellular sensitivity to anti-cancer drugs by FGF-2," Drug Resistance Updates, 2003, 85-94.
Corre et al., "Synthesis and biological evaluation of a triazole-based library of pyrido[2,3-d]pyrimidines as FGFR3 tyrosine kinase inhibitors," Organic & Biomolecular Chemistry, 2010, 8:2164-2173.
Covic et al., "Vascular calcification in chronic kidney disease," Clinical Science, 2010, 119: 111-121.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Dutt et al., "Drug-sensitive FGFR2 mutations in endometrial carcinoma," Supporting Information, Jun. 2008, 8 pages.
Elsheikh et al., "FGFR1 amplification in breast carcinomas: a chromogenic in situ hybridisation analysis," Breast Cancer Research, Mar. 2007, 9(2): 1-12.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.
Faul et al., "FGF23 induces left ventricular hypertrophy," The Journal of Clinical Investigation, 2010, 1-16.
Feng et al., "Targeting Fibroblast Growth Factor Receptor Signaling Inhibits Prostate Cancer Progression," Clinical Cancer Research, 2012, 1-9.

(56) References Cited

OTHER PUBLICATIONS

Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cel lung cancer cells: therapeutic implications and synergism with epidermal growth factor receptor inhibition," Mol Cancer Therapy, 2008, 3408-3419.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fukumoto and Yamashita, "FGF23 is a hormone-regulating phophate metabolism—Unique biological characteristics of FGF23," Bone, 2007, 1190-1195.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gerby et al., "2-Arylidenedihydroindole-3-ones: Design, synthesis, and biological activity on bladder carcinoma cell lines," Bioorganic & Medicinal Chemistry Letters, 2007, 208-213.
Goetz et al., "Isolated C-terminal tail of FGF23 alleviates hypophosphatemia by inhibiting FGF23-FGFR-Klotho complex formation," PNAS, Jan. 2010, 107(1): 407-412.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Grand et al., "Targeting FGFR3 in multiple myeloma: inhibition of t(4;14)-positive cells by SU5402 and PD173074," Leukemia, 2004, 18: 962-966.
Grose and Dickson, "Fibroblast growth factor signaling in tumorigenesis," Cytokine & Growth Factor Reviews, 2005, 179-186.
Guagnano et al., "Discovery of 3-(2,6-Dichloro-3,5-dimethoxy-phenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.

Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinzle et al., "Targeting fibroblast-growth-factor-receptor-dependent signaling for cancer therapy," Expert Opinion, 2011, 1-18.
Hideshima and Anderson, "Preclinical Studies of Novel Targeted Therapies," Hematol Oncol Clin N Am, 2007, 1071-1091.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hynes and Dey, "Potential for Targeting the Fibroblast Growth Factor Receptors in Breast Cancer," Cancer Res, 2010, 70:5199-5202.
Huynh, 15 Expert Opinion Emerging Drugs, 13-26 (2010).
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
International Prelimiary Report on Patentability in International Application No. PCT/US2013/054361, mailed Feb. 19, 2015, 7 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Jan de Beur, "Tumoral Calcinosis: A Look into the Metabolic Mirror of Phosphate Homeostasis," The Journal of Clinical Endocrinology & Metabolism, 2005, 90: 2469-2471.
Jebar et al., "FGFR3 and Ras gene mutations are mutually exclusive genetic events in urothelial cell carcinoma," Oncogene, 2005, 24: 5218-5225.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.

(56) References Cited

OTHER PUBLICATIONS

Kassack et al., "Structure-activity relationships of analogues of NF449 confirm NF449 as the most potent and selective known $P2X_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS ONE, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Krejci et al., "Molecular pathology of the fibroblast growth factor family," Hum Mutat, Sep. 2009, 30(9): 1245-1255.
Krejci et al., "NF449 is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kurosu et al., "Regulation of Fibroblast Growth Factor-23 Signaling by Klotho," The Journal of Biological Chemistry, Mar. 2006, 281(10): 6120-6123.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Liang et al., "Anticancer molecules targeting fibroblast growth factor receptors," Cell Press, 2012, 11 pages.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "In vitro Anti-leukaemia Activity of Pyrrolo[1,2-b][1,2,5]benzothiadiaze-pines (PBTDs)," Recent Patents on Anti-Cancer Drug Discovery, 2010, 58-68.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
McConkey et al., "Molecular genetics of bladder cancer: Emerging mechanisms of tumor initiation and progression," Urologic Oncology: Seminars and Original Investigations, 2010, 429-440.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)-mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
Nitta, "Relationship between Fibroblast Growth Factor-23 and Mineral Metabolism in Chronic Kidney Disease," International Journal of Nephrology, 2010, 1-7.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and Ileal

(56) References Cited

OTHER PUBLICATIONS

Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Piazza et al., "Towards a new age in the treatment of multiple myeloma," Ann Hematol, 2007, 86:159-172.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Ryan et al., "Toxicologic Pathology of Unique Biotechnology Agents and Biotherapies," Toxicologic Pathology, 1999, 27(1): 78-86.
Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search, Science IP, Apr. 2012, 78 pages.
Science IP Order 3101926, Chemical Structure Search, Science IP, Jan. 2015, 50 pages.
Science IP Order 3101983, Chemical Structure Search, Science IP, Jan. 2015, 70 pages.
Science IP Order 3104564, Patent Chemical Structure Search, Science IP, Mar. 2015, 90 pages.
Science IP Order 3104565, Patent Chemical Structure Search, Science IP, Mar. 2015, 521 pages.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-111c mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.

(56) References Cited

OTHER PUBLICATIONS

Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thome and Weil, "Post-translational modifications regulate distinct functions of CARMA1 and BCL10," Trends in Immunology, 2007, 28(6): 281-288.
Thompson et al., "3-(3,5-Dimethoxyphenyl)-1,6-naphthyridine-2,7-diamines and Related 2-Urea Derivatives are Potent and Selective Inhibitors of the FGF Receptor-1 Tyrosine Kinase," J. Med. Chem., 2000, 43: 4200-4211.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis in t(4;14) myeloma," Blood, May 2004, 103(9):3521-3528.
Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.
Turner et al., "FGFR1 Amplification Drives Endocrine Therapy Resistance and is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476.
Wang, 3 Nature Medicine, 887-893 (1997).
Wu, "Urothelial Tumorigenesis: A Tale of Divergent Pathways," Nature Reviews, Sep. 2005, 5: 713-725.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 is Efficacious in a Newly Developed Fibroblast Growth Factor Receptor 3-Expressing Orthotopic Multiple Myeloma Model in Mice," Clin Cancer Res, Aug. 2006, 4908-4915.
Yu et al., "Analysis of the Biochemical Mechanisms for the Endocrine Actions of Firbroblast Growth Factor-23," Endocrinology, Nov. 2005, 146(11): 4647-4656.
Zaid et al., "Identification of FGFR4 as a Potential Therapeutic Target for Advanced-Stage, High-Grade Serous Ovarian Cancer," Clin Cancer Res, 2013, 19(4): 809-820.
Zhang et al., "AZD4547, a potent and selective FGF-receptor inhibitor induces tumor regressions in a human primary model of FGF-receptor 2 amplified gastric cancer and is efficacious in combination with chemotherapy," 2012.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.
Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.
Zhang et al., "Receptor Specificity of the Fibroblast Growth Factor Family," Journal of Biological Chemistry, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.

(56) References Cited

OTHER PUBLICATIONS

Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.
H. Greulich, 17 Trends in Molecular Medicine, 283-292 (2011).
J. Bonaventure et al., 6 Clinical Pediatric Endocrinology, 105-113 (1997).
L. Tan et al., PNAS E4869-E4877 (2014).
Segev et al., 9 Human Molecular Genetics, 249-258 (2000).
International Search Report and Written Opinion in International Application No. PCT/US2014/034662, mailed Oct. 24, 2014, 18 pages.
Hackam and Redelmeier, "Translation of Research Evidence From Animals to Humans," JAMA, 2006, 296(14): 1731-1732.
Heinzle et al., "Is fibroblast growth factor receptor 4 a suitable target of cancer therapy?," Cur. Pharm. Des. 2014, 20:2881-98.
International Search Report and Written Opinion for International Application No. PCT/US2015/056583, dated Dec. 15, 2015, 10 pages.
Jordan, "Tamoxifen: A Most Unlikely Pioneering Medicine," Nature Reviews: Drug Discovery, 2003, 2:205.
Taylor et al., "Identification of FGFR4-activating mutations in human rhabdomyasarcomas that promote metastasis in xenotransplanted models," J Clin Invest, Nov. 2009, 119(11): 3395-407.
International Search Report and Written Opinion in International Application No. PCT/US2016/018737, dated Jun. 2, 2016, 12 pages.
International Preliminary Report on Patentability in International Application No. PCT/US2014/034662, dated Oct. 29, 2015, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
"Substance Record for SID 240993001," Feb. 13, 2015, pp. 1-8.
Cancer [online], [retrieved on Jul. 6, 2007] Retrieved from the Internet, URL: http://www.nlm.nih.gov/medlineplus/cancer.html.
Lala et al., "Role of nitric oxide in tumor progression: Lessons from experimental tumors," Cancer and Metastasis Reviews, 1998, 17: 91-106.
Golub et al., "Molecular Classification of Cancer: Class Discovery and Class Prediction by Gene Expression Monitoring," Science, 1999, 286: 531-537.
I S . M. 1 Chinese Office Action in Chinese Application No. 201480028858.7, dated Aug. 19, 2016, 18 pages (English Translation).

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
1               5                   10                  15
```

BICYCLIC HETEROCYCLES AS FGFR INHIBITORS

FIELD OF THE INVENTION

The present invention relates to bicyclic heterocycles, and pharmaceutical compositions of the same, that are inhibitors of one or more FGFR enzymes and are useful in the treatment of FGFR-associated diseases such as cancer.

BACKGROUND OF INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005).

Aberrant activation of this pathway either through over-expression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook Pharmacology & Therapeutics, 2010; Turner and Grose, Nature Reviews Cancer, 2010). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achrondroplasia and craniosynostosis syndromes.

There is a continuing need for the development of new drugs for the treatment of cancer and other diseases, and the FGFR inhibitors described herein help address this need.

SUMMARY OF INVENTION

The present invention is directed to inhibitors of FGFR having Formula I:

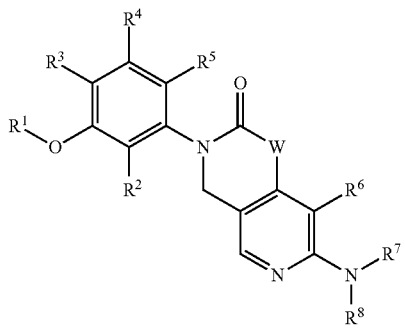

or a pharmaceutically acceptable salt thereof, wherein constituent variables are defined herein.

The present invention is further directed to pharmaceutical compositions comprising a compound of Formula I, or a pharmaceutically acceptable salt thereof, and at least one pharmaceutically acceptable carrier.

The present invention is further directed to methods of inhibiting an FGFR enzyme comprising contacting the enzyme with a compound of Formula I, or a pharmaceutically acceptable salt thereof.

The present invention is further directed to a method of treating a disease associated with abnormal activity or expression of an FGFR enzyme, comprising administering a compound of Formula I, or a pharmaceutically acceptable salt thereof, to a patient in need thereof.

The present invention is further directed to compounds of Formula I for use in treating a disease associated with abnormal activity or expression of an FGFR enzyme.

The present invention is further directed to the use of compounds of Formula I in the preparation of a medicament for use in therapy.

DETAILED DESCRIPTION

The present invention is directed to inhibitors of FGFR having Formula I:

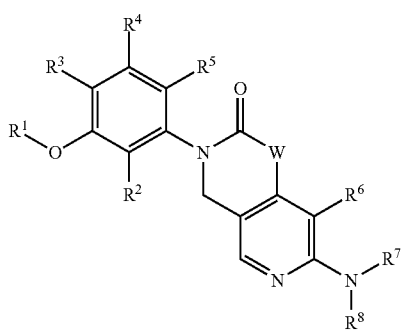

or a pharmaceutically acceptable salt thereof, wherein:
W is $NR^9$, O, or $CR^{10}R^{11}$;
$R^1$ is $C_{1-6}$ alkyl, $C_{1-6}$ haloalkyl, or $C_{3-7}$ cycloalkyl;

R², R³, and R⁵ are each independently selected from H, halo, $C_{1-6}$ alkyl, $C_{2-6}$ alkenyl, $C_{2-6}$ alkynyl, $C_{1-6}$ haloalkyl, cyclopropyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

R⁴ is H, halo, $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-7}$ cycloalkyl, and 4-7 membered heterocycloalkyl are each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

R⁶ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, or $S(O)_2NR^{c2}R^{d2}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{6a}$;

wherein R⁶ is other than H when W is $NR^9$;

each $R^{6a}$ is independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

R⁷ and R⁸ are each independently selected from H, $C_{1-6}$ alkyl, $C_{2-6}$ alkenyl, $C_{2-6}$ alkynyl, —$C(O)R^A$, $S(O)R^A$, $S(O)_2R^A$, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $R^{7a}$;

each $R^{7a}$ is independently selected from $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

R⁹ is H, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $R^{9a}$;

each $R^{9a}$ is independently selected from $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

R¹⁰ and R¹¹ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$;

each $R^{10a}$ is independently selected from $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2$ $NR^{c4}R^{d4}$, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

or $R^{10}$ and $R^{11}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^3$, $C_{1-6}$ alkyl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$, wherein said $C_{1-6}$ alkyl is optionally substituted by 1, 2, or 3 substituents independently selected from $Cy^3$, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

each $R^A$ is independently selected from H, $C_{1-6}$ alkyl, $C_{1-6}$ alkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, wherein said $C_{1-6}$ alkyl, $C_{1-6}$ alkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, or 3 substituents independently selected from $R^{7a}$;

$Cy^1$, $Cy^2$, and $Cy^3$ are each independently selected from $C_{6-10}$ aryl, $C_{3-10}$ cycloalkyl, 5-10 membered heteroaryl, and 4-10 membered heterocycloalkyl, each of which is optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 3-10 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^a$, $R^b$, $R^c$, and $R^d$ is independently selected from H, $C_{1-6}$ alkyl, $C_{1-4}$ haloalkyl, $C_{2-6}$ alkenyl, $C_{2-6}$ alkynyl, and cyclopropyl, wherein said $C_{1-6}$ alkyl, $C_{2-6}$ alkenyl, $C_{2-6}$ alkynyl, and cyclopropyl is optionally substituted with 1, 2, or 3 substituents independently selected from $C_{1-4}$ alkyl, $C_{1-4}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$, $R^{d4}$, $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)$ $NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^e$, $R^{e1}$, $R^{e2}$, $R^{e3}$, $R^{e4}$, and $R^{e5}$ is independently selected from H, $C_{1-4}$ alkyl, CN, $OR^{a6}$, $SR^{b6}$, $S(O)_2R^{b6}$, $C(O)R^{b6}$, $S(O)_2NR^{c6}R^{d6}$, and $C(O)NR^{c6}R^{d6}$;

each $R^{a6}$, $R^{b6}$, $R^{c6}$, and $R^{d6}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^{e6}$ is independently selected from H, $C_{1-4}$ alkyl, and CN.

The present invention is directed to inhibitors of FGFR having Formula I:

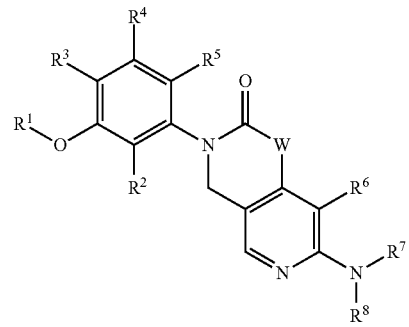

or a pharmaceutically acceptable salt thereof, wherein:

W is $NR^9$, O, or $CR^{10}R^{11}$;

$R^1$ is $C_{1-6}$ alkyl, $C_{1-6}$ haloalkyl, or $C_{3-7}$ cycloalkyl;

$R^2$, $R^3$, and $R^5$ are each independently selected from H, halo, $C_{1-6}$ alkyl, $C_{2-6}$ alkenyl, $C_{2-6}$ alkynyl, $C_{1-6}$ haloalkyl, cyclopropyl, CN, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

$R^4$ is H, halo, $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)$ $R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{3-7}$ cycloalkyl, and 4-7 membered heterocycloalkyl are each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^6$ is H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, or $S(O)_2NR^{c2}R^{d2}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{6a}$;

wherein $R^6$ is other than H when W is $NR^9$;

each $R^{6a}$ is independently selected from $Cy^1$, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl, $C_{2-6}$ alkenyl, and $C_{2-6}$ alkynyl are each optionally substituted with 1, 2, or 3 substituents independently selected from $Cy^1$, halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^7$ and $R^8$ are each independently selected from H, $C_{1-6}$ alkyl, $C_{2-6}$ alkenyl, $C_{2-6}$ alkynyl, $-C(O)R^A$, $S(O)R^A$, $S(O)_2R^A$, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $R^{7a}$;

each $R^{7a}$ is independently selected from $Cy^2$, halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

$R^9$ is H, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $R^{9a}$;

each $R^{9a}$ is independently selected from $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted with 1, 2, or 3 substituents independently selected from $Cy^3$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

$R^{10}$ and $R^{11}$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{10a}$;

each $R^{10a}$ is independently selected from $Cy^3$, halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted with 1, 2, or 3 substituents independently selected from $Cy^2$, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

or $R^{10}$ and $R^{11}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^3$, $C_{1-6}$ alkyl, C$_{1-6}$ haloalkyl, halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$)NR$^{c4}$R$^{d4}$, NR$^{c4}$C(=NR$^{e4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$, wherein said C$_{1-6}$ alkyl is optionally substituted by 1, 2, or 3 substituents independently selected from Cy$^3$, halo, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$)NR$^{c4}$R$^{d4}$, NR$^{c4}$C(=NR$^{e4}$)NR$^{c4}$R$^{d4}$, S(O)R$^{b4}$, S(O)NR$^{c4}$R$^{d4}$, S(O)$_2$R$^{b4}$, NR$^{c4}$S(O)$_2$R$^{b4}$, NR$^{c4}$S(O)$_2$NR$^{c4}$R$^{d4}$, and S(O)$_2$NR$^{c4}$R$^{d4}$;

each R$^A$ is independently selected from H, C$_{1-6}$ alkyl, C$_{1-6}$ alkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, and (4-10 membered heterocycloalkyl)-C$_{1-4}$ alkyl, wherein said C$_{1-6}$ alkyl, C$_{1-6}$ alkoxy, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, and (4-10 membered heterocycloalkyl)-C$_{1-4}$ alkyl are each optionally substituted with 1, 2, or 3 substituents independently selected from R$^{7a}$;

Cy$^1$, Cy$^2$, and Cy$^3$ are each independently selected from C$_{6-10}$ aryl, C$_{3-10}$ cycloalkyl, 5-10 membered heteroaryl, and 4-10 membered heterocycloalkyl, each of which is optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 3-10 membered heterocycloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, C(=NR$^{e5}$)R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$; wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, C(=NR$^{e5}$)NR$^{c5}$R$^{d5}$, NR$^{c5}$C(=NR$^{e5}$)NR$^{c5}$R$^{d5}$, NR$^{c5}$R$^{d5}$, NR$^{c5}$C(O)R$^{b5}$, NR$^{c5}$C(O)OR$^{a5}$, NR$^{c5}$C(O)NR$^{c5}$R$^{d5}$, NR$^{c5}$S(O)R$^{b5}$, NR$^{c5}$S(O)$_2$R$^{b5}$, NR$^{c5}$S(O)$_2$NR$^{c5}$R$^{d5}$, S(O)R$^{b5}$, S(O)NR$^{c5}$R$^{d5}$, S(O)$_2$R$^{b5}$, and S(O)$_2$NR$^{c5}$R$^{d5}$;

each R$^a$, R$^b$, R$^c$, and R$^d$ is independently selected from H, C$_{1-6}$ alkyl, C$_{1-4}$ haloalkyl, C$_{2-6}$ alkenyl, C$_{2-6}$ alkynyl, and cyclopropyl, wherein said C$_{1-6}$ alkyl, C$_{2-6}$ alkenyl, C$_{2-6}$ alkynyl, and cyclopropyl is optionally substituted with 1, 2, or 3 substituents independently selected from C$_{1-4}$ alkyl, C$_{1-4}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$;

each R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, R$^{d3}$, R$^{a4}$, R$^{b4}$, R$^{c4}$, and R$^{d4}$, R$^{a5}$, R$^{b5}$, R$^{c5}$, and R$^{d5}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, or (4-10 membered heterocycloalkyl)-C$_{1-4}$ alkyl, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl, C$_{3-10}$ cycloalkyl-C$_{1-4}$ alkyl, (5-10 membered heteroaryl)-C$_{1-4}$ alkyl, and (4-10 membered heterocycloalkyl)-C$_{1-4}$ alkyl is optionally substituted with 1, 2, 3, 4, or 5 substituents independently selected from C$_{1-4}$ alkyl, C$_{1-4}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$;

or any R$^c$ and R$^d$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$;

or any R$^{c1}$ and R$^{d1}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$;

or any R$^{c2}$ and R$^{d2}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, and 5-6 membered heteroaryl, C$_{1-6}$ haloalkyl, halo, CN, OR$^{a6}$, SR$^{a6}$, C(O)R$^{b6}$, C(O)NR$^{c6}$R$^{d6}$, C(O)OR$^{a6}$, OC(O)R$^{b6}$, OC(O)NR$^{c6}$R$^{d6}$, NR$^{c6}$R$^{d6}$, NR$^{c6}$C(O)R$^{b6}$, NR$^{c6}$C(O)NR$^{c6}$R$^{d6}$, NR$^{c6}$C(O)OR$^{a6}$, C(=NR$^{e6}$)NR$^{c6}$R$^{d6}$, NR$^{c6}$C(=NR$^{e6}$)NR$^{c6}$R$^{d6}$, S(O)R$^{b6}$, S(O)NR$^{c6}$R$^{d6}$, S(O)$_2$R$^{b6}$, NR$^{c6}$S(O)$_2$R$^{b6}$, NR$^{c6}$S(O)$_2$NR$^{c6}$R$^{d6}$, and S(O)$_2$NR$^{c6}$R$^{d6}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)$ $NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $C(=NR^{e6})NR^{c6}R^{d6}$, $NR^{c6}C(=NR^{e6})NR^{c6}R^{d6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^e$, $R^{e1}$, $R^{e2}$, $R^{e3}$, $R^{e4}$, and $R^{e5}$ is independently selected from H, $C_{1-4}$ alkyl, CN, $OR^{a6}$, $SR^{b6}$, $S(O)_2R^{b6}$, $C(O)R^{b6}$, $S(O)_2NR^{c6}R^{d6}$, and $C(O)NR^{c6}R^{d6}$;

each $R^{a6}$, $R^{b6}$, $R^{c6}$, and $R^{d6}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

or any $R^{c6}$ and $R^{d6}$ together with the N atom to which they are attached form a 4-, 5-, 6-, or 7-membered heterocycloalkyl group optionally substituted with 1, 2, or 3 substituents independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy; and each $R^{e6}$ is independently selected from H, $C_{1-4}$ alkyl, and CN.

In some embodiments, W is $NR^9$ or $CR^{10}R^{11}$.

In some embodiments, W is $NR^9$.

In some embodiments, $R^9$ is $C_{1-6}$ alkyl.

In some embodiments, $R^9$ is methyl.

In some embodiments, $R^9$ is $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $R^{9a}$.

In some embodiments, $R^9$ is $C_{6-10}$ aryl, $C_{3-10}$ cycloalkyl, 5-10 membered heteroaryl, $C_{6-10}$ aryl-$C_{1-4}$ alkyl, $C_{3-10}$ cycloalkyl-$C_{1-4}$ alkyl, or (5-10 membered heteroaryl)-$C_{1-4}$ alkyl, wherein said $C_{6-10}$ aryl, $C_{3-10}$ cycloalkyl, 5-10 membered heteroaryl, $C_{6-10}$ aryl-$C_{1-4}$ alkyl, $C_{3-10}$ cycloalkyl-$C_{1-4}$ alkyl, and (5-10 membered heteroaryl)-$C_{1-4}$ alkyl are each optionally substituted with 1 or 2 substituents independently selected from halo and $C_{1-4}$ alkyl.

In some embodiments, $R^9$ is phenyl, 2H-tetrazol-5-yl, benzyl, 1H-pyrazol-4-ylmethyl, cyclopentyl, or cyclopropylmethyl each optionally substituted with 1 or 2 substituents independently selected from F and methyl.

In some embodiments, W is $CR^{10}R^{11}$.

In some embodiments, $R^{10}$ and $R^{11}$ are each $C_{1-6}$ alkyl.

In some embodiments, $R^{10}$ and $R^{11}$ are each methyl.

In some embodiments, $R^{10}$ and $R^{11}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^3$, $C_{1-6}$ alkyl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$, wherein said $C_{1-6}$ alkyl is optionally substituted by 1, 2, or 3 substituents independently selected from $Cy^3$, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$.

In some embodiments, $R^{10}$ and $R^{11}$ together with the carbon atom to which they are attached form a 3-, 4-, 5-, 6-, or 7-membered cycloalkyl group.

In some embodiments, $R^{10}$ and $R^{11}$ together with the carbon atom to which they are attached form a cyclopropyl group.

In some embodiments, $R^1$ is methyl.
In some embodiments, $R^2$ is halo.
In some embodiments, $R^2$ is fluoro.
In some embodiments, $R^3$ is H.
In some embodiments, $R^4$ is $OR^{a1}$.
In some embodiments, $R^4$ is methoxy.
In some embodiments, $R^5$ is halo.
In some embodiments, $R^5$ is fluoro.
In some embodiments, $R^6$ is H.
In some embodiments, $R^6$ is H and W is $CR^{10}R^{11}$.

In some embodiments, $R^6$ is H, halo, $C_{1-6}$ alkyl, $C_{2-6}$ alkenyl, $C_{6-10}$ aryl, 5-10 membered heteroaryl, 4-10 membered heterocycloalkyl, CN, or $OR^{a2}$; wherein said $C_{1-6}$ alkyl, $C_{2-6}$ alkenyl, $C_{6-10}$ aryl, 5-10 membered heteroaryl, and 4-10 membered heterocycloalkyl are each optionally substituted with 1, 2, 3, 4, or 5 substituents independently selected from $R^{6a}$.

In some embodiments, $R^6$ is halo, $C_{1-6}$ alkyl, $C_{2-6}$ alkenyl, $C_{6-10}$ aryl, 5-10 membered heteroaryl, 4-10 membered heterocycloalkyl, CN, or $OR^{a2}$; wherein said $C_{1-6}$ alkyl, $C_{2-6}$ alkenyl, $C_{6-10}$ aryl, 5-10 membered heteroaryl, and 4-10 membered heterocycloalkyl are each optionally substituted with 1, 2, 3, 4, or 5 substituents independently selected from $R^{6a}$.

In some embodiments, $R^6$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, or $OR^{a2}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{6a}$.

In some embodiments, $R^6$ is halo, $C_{1-6}$ alkyl, $C_{2-6}$ alkenyl, phenyl, 5-6 membered heteroaryl, 6-membered heterocycloalkyl, CN, or $OR^{a2}$; wherein said $C_{1-6}$ alkyl, $C_{2-6}$ alkenyl, phenyl, 5-6 membered heteroaryl, and 6-membered heterocycloalkyl are each optionally substituted with 1, 2, 3, 4, or 5 substituents independently selected from $R^{6a}$.

In some embodiments, $R^6$ is $C_{1-6}$ alkyl, $C_{2-6}$ alkenyl, phenyl, 5-6 membered heteroaryl, 6-membered heterocycloalkyl, CN, or $OR^{a2}$; wherein said $C_{1-6}$ alkyl, $C_{2-6}$ alkenyl, phenyl, 5-6 membered heteroaryl, and 6-membered heterocycloalkyl are each optionally substituted with 1, 2, 3, 4, or 5 substituents independently selected from $R^{6a}$.

In some embodiments, $R^6$ is chloro, methyl, ethyl, CN, ethoxy, methoxyethoxy, phenoxy, 2-(4-methylpiperazin-1-yl)ethoxy, phenyl, 4-fluorophenyl, benzyl, phenylethyl, 2-phenylvinyl, 3,6-dihydro-2H-pyran-4-yl, 3-pyridyl, 4-pyridyl, 1H-pyrazol-4-yl, 1-methyl-1H-pyrazol-5-yl, 1-methyl-1H-pyrazol-4-yl, 1-ethyl-1H-pyrazol-4-yl, 1-(2-hydroxyethyl)-1H-pyrazol-4-yl, or 1-(piperidin-4-yl)-1H-pyrazol-4-yl.

In some embodiments, $R^6$ is methyl, ethyl, CN, ethoxy, methoxyethoxy, phenoxy, 2-(4-methylpiperazin-1-yl)ethoxy, phenyl, 4-fluorophenyl, benzyl, phenethyl, 2-phenylvinyl, 3,6-dihydro-2H-pyran-4-yl, 3-pyridyl, 4-pyridyl, 1H-pyrazol-4-yl, 1-methyl-1H-pyrazol-5-yl, 1-methyl-1H-pyrazol-4-yl, 1-ethyl-1H-pyrazol-4-yl, 1-(2-hydroxyethyl)-1H-pyrazol-4-yl, or 1-(piperidin-4-yl)-1H-pyrazol-4-yl.

In some embodiments, $R^6$ is methyl.

In some embodiments, $R^6$ is pyrazolyl optionally substituted with 1 or 2 substituents independently selected from $R^{6a}$.

In some embodiments, $R^7$ and $R^8$ are each independently selected from H, $C_{1-6}$ alkyl, —C(O)$R^A$, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{6-10}$ aryl, $C_{3-10}$ cycloalkyl, 5-10 membered heteroaryl, 4-10 membered heterocycloalkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $R^{7a}$.

In some embodiments, $R^7$ and $R^8$ are each independently selected from H, 2-hydroxypropyl, —C(O)OCH$_3$, 3-fluorophenyl, cyclopropyl, cyclobutyl, 3,3-difluorocyclobutyl, cyclopentyl, cyclohexyl, 4-hydroxycyclohexyl, methyl, 1-methyl-1H-pyrazol-4-yl, pyridin-3-yl, N-methylpiperidin-4-yl, tetrahydro-2H-pyran-4-yl, tetrahydrofuran-3-yl, 1-phenylethyl, (1-methyl-1H-pyrazol-4-yl)methyl, 2-morpholino-4-ylethyl, pyridin-2-ylmethyl, N-methylpiperazin-1-ylethyl, and tetrahydrofuran-2-ylmethyl.

In some embodiments, one of $R^7$ and $R^8$ is H.
In some embodiments, $R^7$ and $R^8$ are each H.
In some embodiments, the compounds of the invention have Formula IIa:

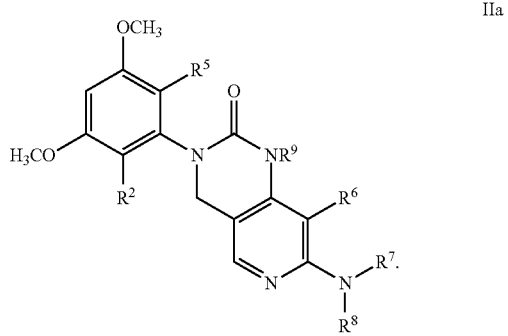

IIa

In some embodiments, wherein the compound has Formula IIa, $R^2$ is halo.

In some embodiments, wherein the compound has Formula IIa, $R^2$ is fluoro.

In some embodiments, wherein the compound has Formula IIa, $R^5$ is halo.

In some embodiments, wherein the compound has Formula IIa, $R^5$ is fluoro.

In some embodiments, wherein the compound has Formula IIa, $R^6$ is halo, $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, or $OR^{a2}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{6a}$.

In some embodiments, wherein the compound has Formula IIa, $R^6$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, or $OR^{a2}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{6a}$.

In some embodiments, wherein the compound has Formula IIa, $R^6$ is halo, $C_{1-6}$ alkyl, $C_{2-6}$ alkenyl, phenyl, 5-6 membered heteroaryl, 6-membered heterocycloalkyl, CN, or $OR^{a2}$; wherein said $C_{1-6}$ alkyl, $C_{2-6}$ alkenyl, phenyl, 5-6 membered heteroaryl, and 6-membered heterocycloalkyl are each optionally substituted with 1, 2, 3, 4, or 5 substituents independently selected from $R^{6a}$.

In some embodiments, wherein the compound has Formula IIa, $R^6$ is $C_{1-6}$ alkyl, $C_{2-6}$ alkenyl, phenyl, 5-6 membered heteroaryl, 6-membered heterocycloalkyl, CN, or $OR^{a2}$; wherein said $C_{1-6}$ alkyl, $C_{2-6}$ alkenyl, phenyl, 5-6 membered heteroaryl, and 6-membered heterocycloalkyl are each optionally substituted with 1, 2, 3, 4, or 5 substituents independently selected from $R^{6a}$.

In some embodiments, wherein the compound has Formula IIa, $R^6$ is chloro, methyl, ethyl, CN, ethoxy, methoxyethoxy, phenoxy, 2-(4-methylpiperazin-1-yl)ethoxy, phenyl, 4-fluorophenyl, benzyl, phenylethyl, 2-phenylvinyl, 3,6-dihydro-2H-pyran-4-yl, 3-pyridyl, 4-pyridyl, 1H-pyrazol-4-yl, 1-methyl-1H-pyrazol-5-yl, 1-methyl-1H-pyrazol-4-yl, 1-ethyl-1H-pyrazol-4-yl, 1-(2-hydroxyethyl)-1H-pyrazol-4-yl, or 1-(piperidin-4-yl)-1H-pyrazol-4-yl.

In some embodiments, wherein the compound has Formula IIa, $R^6$ is methyl, ethyl, CN, ethoxy, methoxyethoxy, phenoxy, 2-(4-methylpiperazin-1-yl)ethoxy, phenyl, 4-fluorophenyl, benzyl, phenethyl, 2-phenylvinyl, 3,6-dihydro-2H-pyran-4-yl, 3-pyridyl, 4-pyridyl, 1H-pyrazol-4-yl, 1-methyl-1H-pyrazol-5-yl, 1-methyl-1H-pyrazol-4-yl, 1-ethyl-1H-pyrazol-4-yl, 1-(2-hydroxyethyl)-1H-pyrazol-4-yl, or 1-(piperidin-4-yl)-1H-pyrazol-4-yl.

In some embodiments, wherein the compound has Formula IIa, $R^9$ is $C_{1-6}$ alkyl.

In some embodiments, wherein the compound has Formula IIa, $R^9$ is methyl.

In some embodiments, the compounds of the invention have Formula IIb:

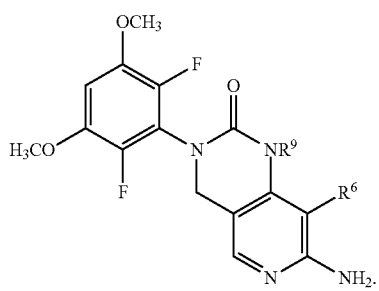

IIb

In some embodiments, wherein the compound has Formula IIb, $R^6$ is halo, $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, CN, or $OR^{a2}$; wherein said $C_{1-6}$ alkyl, $C_{2-6}$ alkenyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{6a}$.

In some embodiments, wherein the compound has Formula IIb, $R^6$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, or $OR^{a2}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^{6a}$.

In some embodiments, wherein the compound has Formula IIb, $R^6$ is halo, $C_{1-6}$ alkyl, $C_{2-6}$ alkenyl, phenyl, 5-6 membered heteroaryl, 6-membered heterocycloalkyl, CN, or $OR^{a2}$; wherein said $C_{1-6}$ alkyl, $C_{2-6}$ alkenyl, phenyl, 5-6 membered heteroaryl, and 6-membered heterocycloalkyl are each optionally substituted with 1, 2, 3, 4, or 5 substituents independently selected from $R^{6a}$.

In some embodiments, wherein the compound has Formula IIb, $R^6$ is $C_{1-6}$ alkyl, $C_{2-6}$ alkenyl, phenyl, 5-6 membered heteroaryl, 6-membered heterocycloalkyl, CN, or $OR^{a2}$; wherein said $C_{1-6}$ alkyl, $C_{2-6}$ alkenyl, phenyl, 5-6 membered heteroaryl, and 6-membered heterocycloalkyl are each optionally substituted with 1, 2, 3, 4, or 5 substituents independently selected from $R^{6a}$.

In some embodiments, wherein the compound has Formula IIb, $R^6$ is chloro, methyl, ethyl, CN, ethoxy, methoxyethoxy, phenoxy, 2-(4-methylpiperazin-1-yl)ethoxy, phenyl, 4-fluorophenyl, benzyl, phenylethyl, 2-phenylvinyl, 3,6-dihydro-2H-pyran-4-yl, 3-pyridyl, 4-pyridyl, 1H-pyrazol-4-yl, 1-methyl-1H-pyrazol-5-yl, 1-methyl-1H-pyrazol-4-yl, 1-ethyl-1H-pyrazol-4-yl, 1-(2-hydroxyethyl)-1H-pyrazol-4-yl, or 1-(piperidin-4-yl)-1H-pyrazol-4-yl.

In some embodiments, wherein the compound has Formula IIb, $R^6$ is methyl, ethyl, CN, ethoxy, methoxyethoxy, phenoxy, 2-(4-methylpiperazin-1-yl)ethoxy, phenyl, 4-fluorophenyl, benzyl, phenethyl, 2-phenylvinyl, 3,6-dihydro-2H-pyran-4-yl, 3-pyridyl, 4-pyridyl, 1H-pyrazol-4-yl, 1-methyl-1H-pyrazol-5-yl, 1-methyl-1H-pyrazol-4-yl, 1-ethyl-1H-pyrazol-4-yl, 1-(2-hydroxyethyl)-1H-pyrazol-4-yl, or 1-(piperidin-4-yl)-1H-pyrazol-4-yl.

In some embodiments, wherein the compound has Formula IIb, $R^9$ is $C_{1-6}$ alkyl.

In some embodiments, wherein the compound has Formula IIb, $R^9$ is methyl.

In some embodiments, the compounds of the invention have Formula IIIa:

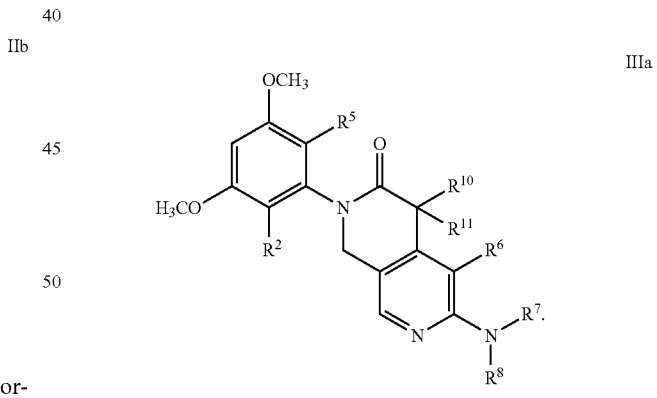

IIIa

In some embodiments, wherein the compound has Formula IIIa, $R^2$ is halo.

In some embodiments, wherein the compound has Formula IIIa, $R^2$ is fluoro.

In some embodiments, wherein the compound has Formula IIIa, $R^5$ is halo.

In some embodiments, wherein the compound has Formula IIIa, $R^5$ is fluoro.

In some embodiments, wherein the compound has Formula IIIa, $R^6$ is H.

some embodiments, wherein the compound has Formula IIIa, $R^{10}$ and $R^{11}$ are both $C_{1-6}$ alkyl.

In some embodiments, wherein the compound has Formula IIIa, $R^{10}$ and $R^{11}$ are both methyl.

In some embodiments, wherein the compound has Formula IIIa, $R^{10}$ and $R^{11}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^3$, $C_{1-6}$ alkyl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$, wherein said $C_{1-6}$ alkyl is optionally substituted by 1, 2, or 3 substituents independently selected from $Cy^3$, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$.

In some embodiments, wherein the compound has Formula IIIa, $R^{10}$ and $R^{11}$ together with the carbon atom to which they are attached form a 3-, 4-, 5-, 6-, or 7-membered cycloalkyl group.

In some embodiments, wherein the compound has Formula IIIa, $R^{10}$ and $R^{11}$ together with the carbon atom to which they are attached form a cyclopropyl group.

In some embodiments, wherein the compound has Formula IIIa, $R^7$ and $R^8$ are each independently selected from H, $C_{1-6}$ alkyl, —$C(O)R^A$, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{6-10}$ aryl, $C_{3-10}$ cycloalkyl, 5-10 membered heteroaryl, 4-10 membered heterocycloalkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $R^{7a}$.

In some embodiments, wherein the compound has Formula IIIa, $R^7$ and $R^8$ are each independently selected from H, 2-hydroxypropyl, —$C(O)OCH_3$, 3-fluorophenyl, cyclopropyl, cyclobutyl, 3,3-difluorocyclobutyl, cyclopentyl, cyclohexyl, 4-hydroxycyclohexyl, methyl, 1-methyl-1H-pyrazol-4-yl, pyridin-3-yl, N-methylpiperidin-4-yl, tetrahydro-2H-pyran-4-yl, tetrahydrofuran-3-yl, 1-phenylethyl, (1-methyl-1H-pyrazol-4-yl)methyl, 2-morpholino-4-yl-ethyl, pyridin-2-ylmethyl, N-methylpiperazin-1-ylethyl, and tetrahydrofuran-2-ylmethyl.

In some embodiments, wherein the compound has Formula IIIa, one of $R^7$ and $R^8$ is H.

In some embodiments, wherein the compound has Formula IIIa, $R^7$ and $R^8$ are each H.

In some embodiments, the compounds of the invention have Formula IIIb:

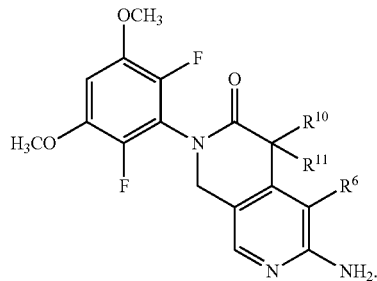

IIIb

In some embodiments, wherein the compound has Formula IIIb, $R^6$ is H.

In some embodiments, wherein the compound has Formula IIIb, $R^{10}$ and $R^{11}$ are both $C_{1-6}$ alkyl.

In some embodiments, wherein the compound has Formula IIIb, $R^{10}$ and $R^{11}$ are both methy.

In some embodiments, wherein the compound has Formula IIIb, $R^{10}$ and $R^{11}$ together with the carbon atom to which they are attached form a 3-, 4-, 5-, 6-, or 7-membered cycloalkyl group or a 4-, 5-, 6-, or 7-membered heterocycloalkyl group, each optionally substituted with 1, 2, or 3 substituents independently selected from $Cy^3$, $C_{1-6}$ alkyl, $C_{1-6}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$, wherein said $C_{1-6}$ alkyl is optionally substituted by 1, 2, or 3 substituents independently selected from $Cy^3$, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$.

In some embodiments, wherein the compound has Formula IIIb, $R^{10}$ and $R^{11}$ together with the carbon atom to which they are attached form a 3-, 4-, 5-, 6-, or 7-membered cycloalkyl group.

In some embodiments, wherein the compound has Formula IIIb, $R^{10}$ and $R^{11}$ together with the carbon atom to which they are attached form a cyclopropyl group.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$", where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl", employed alone or in combination with other terms, refers to a saturated hydrocarbon group that may be straight-chain or branched. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, "alkenyl", employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl", employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo. In some embodiments, halo is F or Cl. In some embodiments, halo is F.

As used herein, the term "haloalkyl", employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy", employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy", employed alone or in combination with other terms, refers to a group of formula —O-(haloalkyl). In some embodiments, the alkyl group has 1 to 6 or 1 to 4 carbon atoms. An example haloalkoxy group is —$OCF_3$.

As used herein, "amino", employed alone or in combination with other terms, refers to $NH_2$.

As used herein, the term "alkylamino", employed alone or in combination with other terms, refers to a group of formula —). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino", employed alone or in combination with other terms, refers to a group of formula —$N(alkyl)_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "alkylthio", employed alone or in combination with other terms, refers to a group of formula —S-alkyl. In some embodiments, the alkyl group has 1 to 6 or 1 to 4 carbon atoms.

As used herein, the term "cycloalkyl", employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5] octane and the like). In some embodiments, the cycloalkyl group has 3 to 10 ring members, or 3 to 7 ring members, or 3 to 6 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "cycloalkylalkyl", employed alone or in combination with other terms, refers to a group of formula cycloalkyl-alkyl-. In some embodiments, the alkyl portion has 1 to 4, 1 to 3, 1 to 2, or 1 carbon atom(s). In some embodiments, the alkyl portion is methylene. In some embodiments, the cycloalkyl portion has 3 to 10 ring members or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "heterocycloalkyl", employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-azaspiro[4.5]decan-N-yl] and the like). In some embodiments, the heterocycloalkyl group has 3 to 10 ring-forming atoms, 4 to 10 ring-forming atoms, or 3 to 8 ring forming atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, dihydropyran ring, tetrahydropyran ring, tetrahyropyridine, azetidine ring, or tetrahydrofuran ring.

As used herein, the term "heterocycloalkylalkyl", employed alone or in combination with other terms, refers to a group of formula heterocycloalkyl-alkyl-. In some embodiments, the alkyl portion has 1 to 4, 1 to 3, 1 to 2, or 1 carbon atom(s). In some embodiments, the alkyl portion is methylene. In some embodiments, the heterocycloalkyl portion has 3 to 10 ring members, 4 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "aryl", employed alone or in combination with other terms, refers to a monocyclic or polycyclic (e.g., having 2 fused rings) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "arylalkyl", employed alone or in combination with other terms, refers to a group of formula aryl-alkyl-. In some embodiments, the alkyl portion has 1 to 4, 1 to 3, 1 to 2, or 1 carbon atom(s). In some embodiments, the alkyl portion is methylene. In some embodiments, the aryl portion is phenyl. In some embodiments, the aryl group is a monocyclic or bicyclic group. In some embodiments, the arylalkyl group is benzyl.

As used herein, the term "heteroaryl", employed alone or in combination with other terms, refers to a monocyclic or polycyclic (e.g., having 2 or 3 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In one embodiment the heteroaryl group is a 3 to 10 membered heteroaryl group. In another embodiment the heteroaryl group is a 4 to 10 membered heteroaryl group. In another embodiment the heteroaryl group is a 3 to 7 membered heteroaryl group. In another embodiment the heteroaryl group is a 5 to 6 membered heteroaryl group.

As used herein, the term "heteroarylalkyl", employed alone or in combination with other terms, refers to a group of formula heteroaryl-alkyl-. In some embodiments, the alkyl portion has 1 to 4, 1 to 3, 1 to 2, or 1 carbon atom(s). In some embodiments, the alkyl portion is methylene. In some embodiments, the heteroaryl portion is a monocyclic or bicyclic group having 1, 2, 3, or 4 heteroatoms independently selected from nitrogen, sulfur and oxygen.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzyl-amine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The following abbreviations may be used herein: AcOH (acetic acid); $Ac_2O$ (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography mass spectrometry); m (multiplet); M (molar); mCPBA (3-chloroperoxybenzoic acid); $MgSO_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); $NaHCO_3$ (sodium bicarbonate); NaOH (sodium hydroxide); $Na_2SO_4$ (sodium sulfate); $NH_4Cl$ (ammonium chloride); $NH_4OH$ (ammonium hydroxide); nM (nanomolar); NMR (nuclear magnetic resonance spectroscopy); OTf (trifluoromethanesulfonate); Pd (palladium); Ph (phenyl); pM (picomolar); PMB (para-methoxybenzyl), $POCl_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); µg (microgram(s)); µL (microliter(s)); µM (micromolar); wt % (weight percent), Synthesis Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

Compounds of the invention can be prepared according to numerous preparatory routes known in the literature. Example synthetic methods for preparing compounds of the invention are provided in the Schemes below.

A series of bicyclic urea derivatives of formula 10 can be prepared by the methods outlined in Scheme 1. Amino ester 2 can be prepared by treating suitable amines $R^9NH_2$ with ester 1. The resulting ester 2 is subjected to a reduction-oxidation sequence to afford aldehyde 3. Example reducing reagents include DIBAL-H (diisobutylaluminium hydride), LAH (lithium aluminium hydride), Super-H (lithium triethylborohydride), etc; and example oxidants include Dess-Martin Periodinane, $MnO_2$, Swern Oxidation, etc. The aniline compound 5 is synthesized by coupling aldehyde 3 and aniline 4 through reductive amination. Then cyclization of diamino compound 5 can be carried out with triphosgene or the equivalent such as carbonyldiimidazole (CDI), phosgene, diphosgene, etc. affording the bicyclic urea derivatives of formula 6. Displacement of the chloride with 4-methoxybenzylamine (PMB-$NH_2$) with the aid of a palladium catalyst and then deprotection of PMB (4-methoxybenzyl) group with Trifluoroacetic acid (TFA) can provide the aminopyridine compound 8. Halogenation of the pyridine ring with an appropriate halogenation reagent such as, for example, NBS (N-bromosuccinimide), NCS (N-chlorosuccinimide) NIS (N-iodosuccinimide), etc., can introduce a halogen for further elaboration. A variety of groups can be attached through palladium catalyzed coupling including, but not limited to, Suzuki coupling, Stille coupling, Neigishi coupling, Sonogashira coupling, ect. and copper catalyzed Ullmann coupling to afford compound 10.

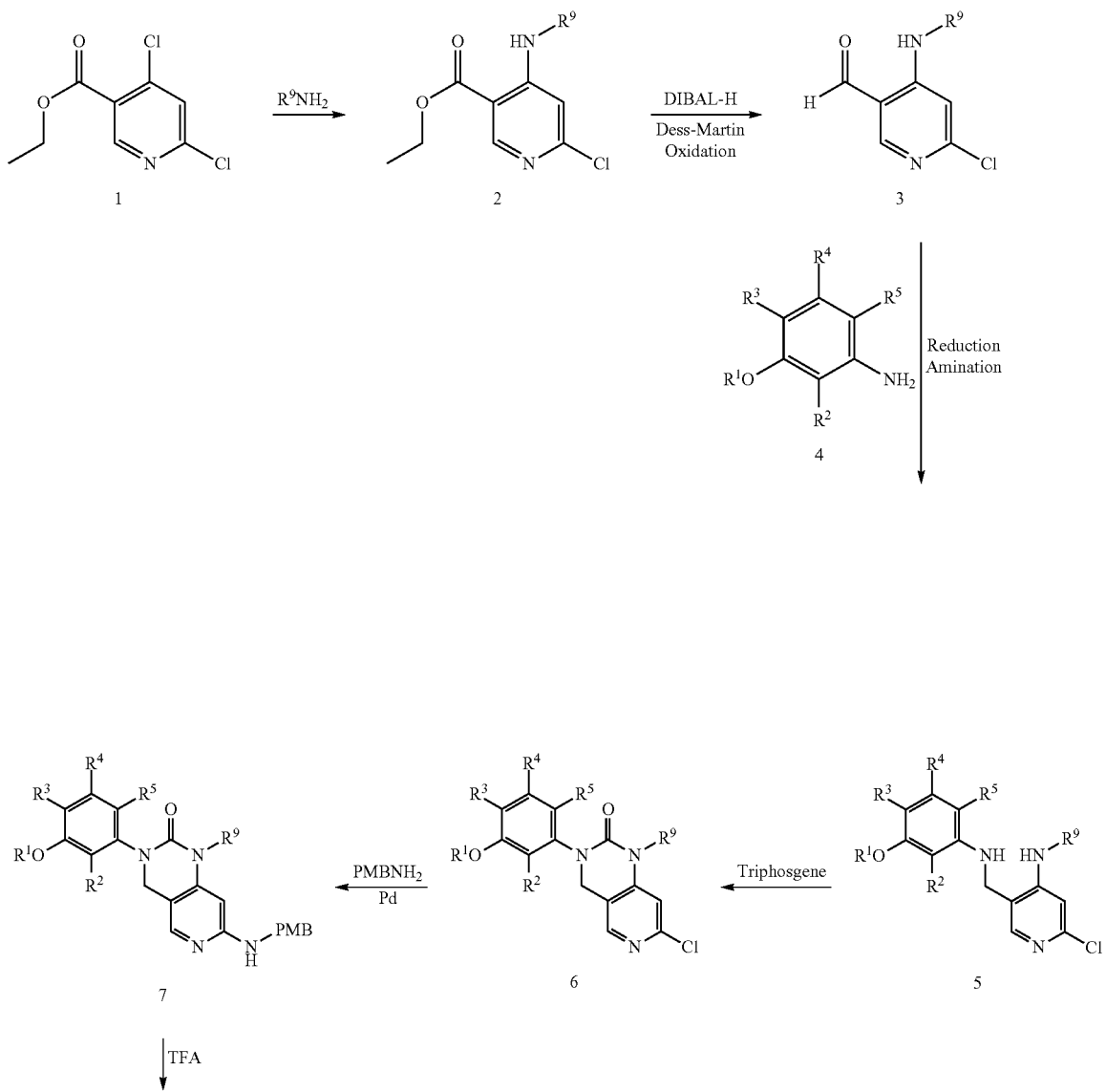

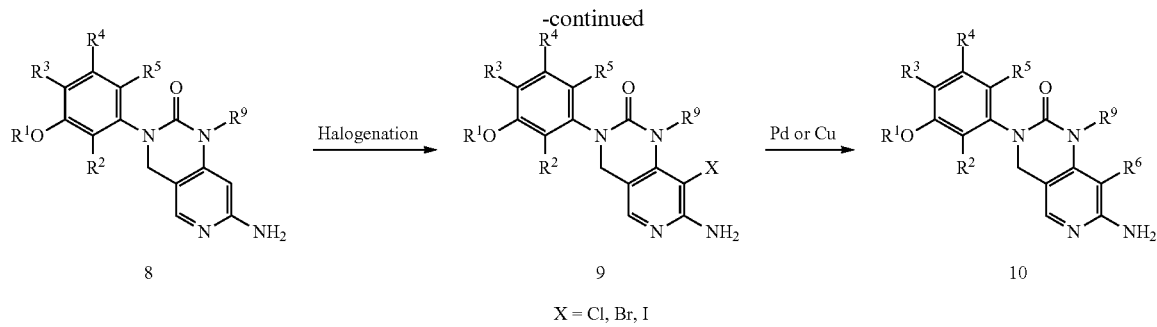

X = Cl, Br, I

A series of aniline derivatives of formula 13 can be prepared by the methods outlined in Scheme 2. Displacement of the chloride 6 with $R^8$—$NH_2$ in the presence of palladium catalyst can provide the aminopyridine compound 11. Halogenation of the pyridine ring with an appropriate halogenating reagent such as NBS, NCS, NIS, etc. can provide compound 12 for further elaboration. Palladium catalyzed coupling of compound 12 by, for example, Suzuki coupling, Stille coupling, Neigishi coupling, Sonogashira coupling, etc. or copper catalyzed Ullmann coupling can afford compound 13.

Scheme 2

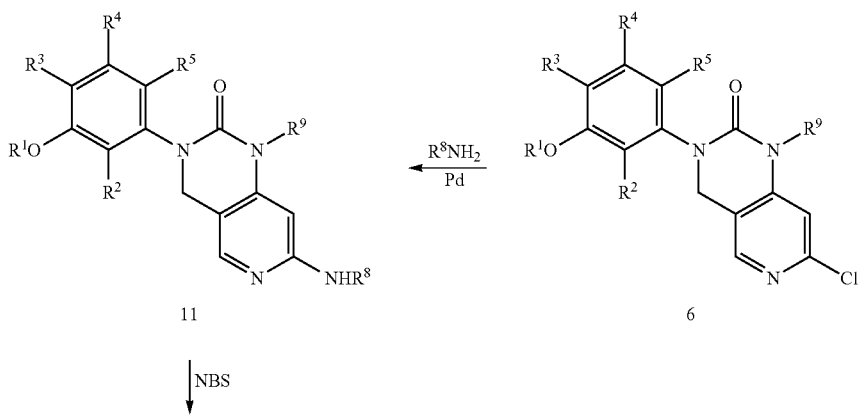

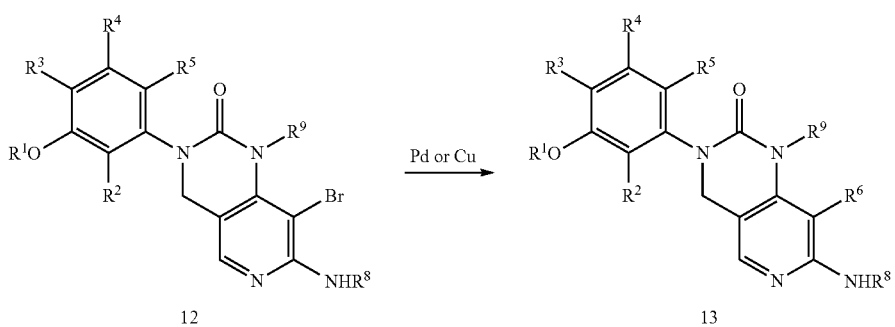

A series of aniline derivatives 14 can be prepared according to the procedures outlined in Scheme 3. Displacement of fluorine in compound 15 with benzylamine (BnNH$_2$) provides the aniline 16 which can be converted to bis-ether by reacting with a suitable sodium alkoxide (NaOR where R is alkyl) followed by saponification to provide acid 17. Compound 18 can be obtained by decarboxylation of benzoic acid 17, followed by hydrogenation to remove the protecting group to afford aniline 14.

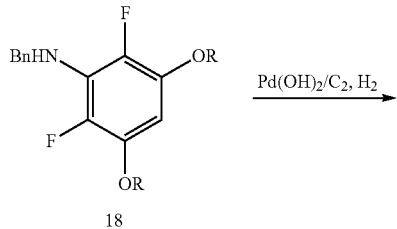

Scheme 3

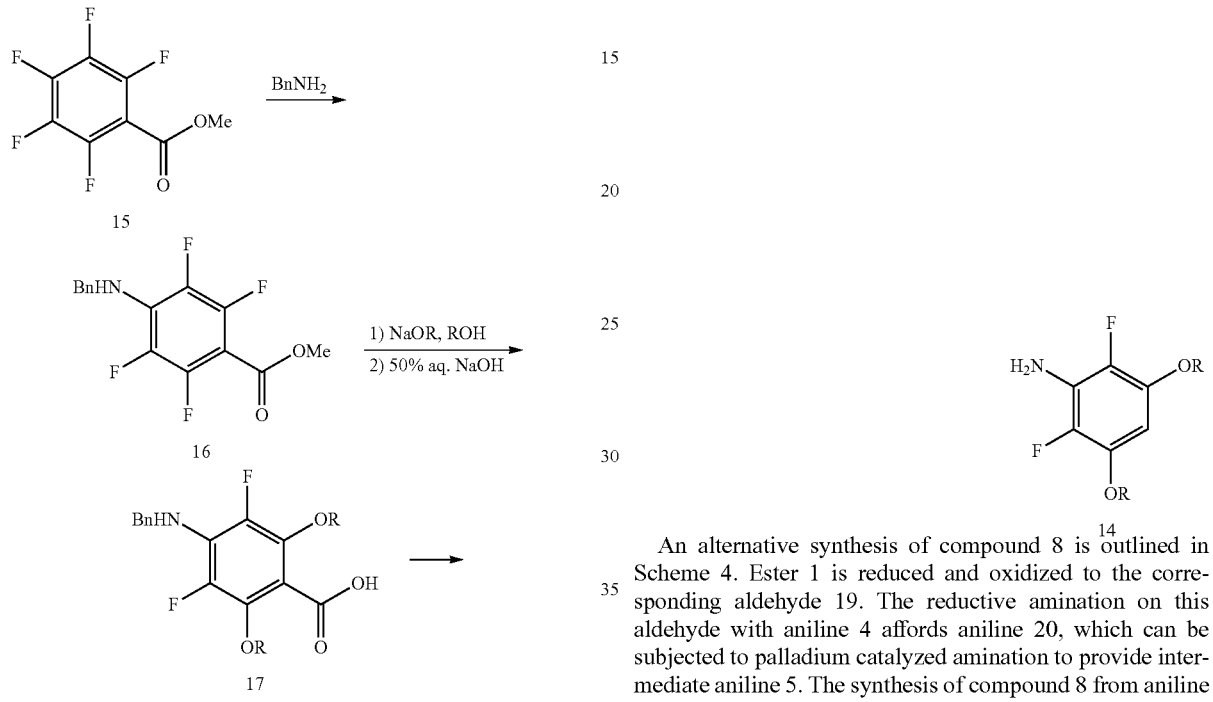

An alternative synthesis of compound 8 is outlined in Scheme 4. Ester 1 is reduced and oxidized to the corresponding aldehyde 19. The reductive amination on this aldehyde with aniline 4 affords aniline 20, which can be subjected to palladium catalyzed amination to provide intermediate aniline 5. The synthesis of compound 8 from aniline 5 follows the same procedure described in Scheme 1.

Scheme 4

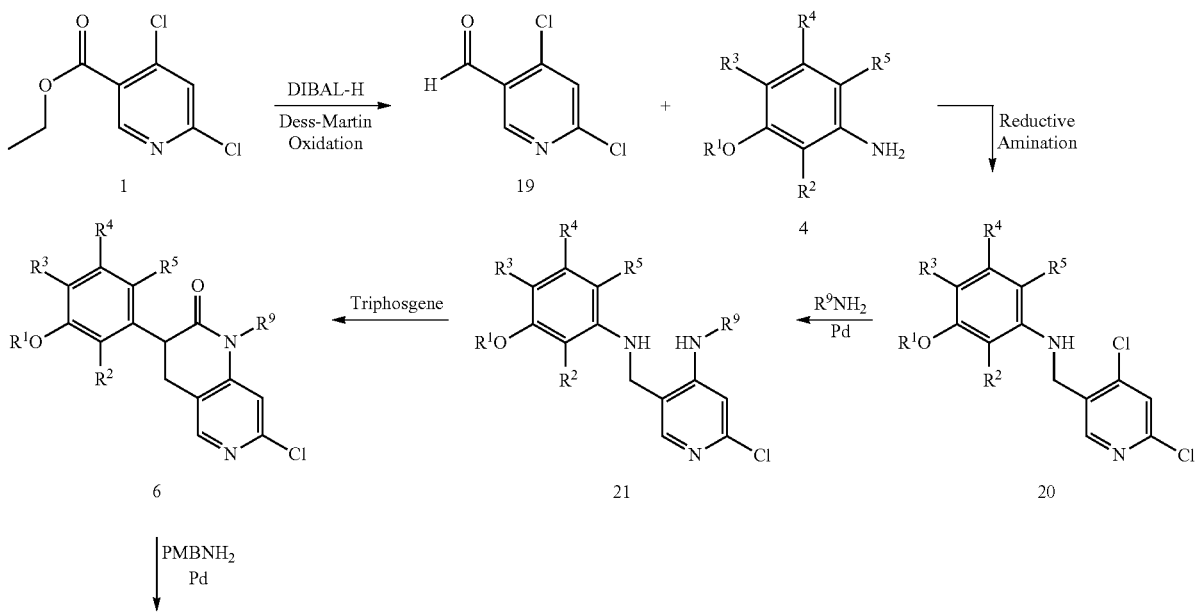

33

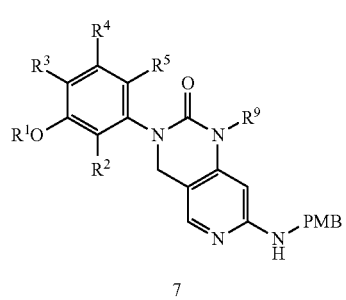 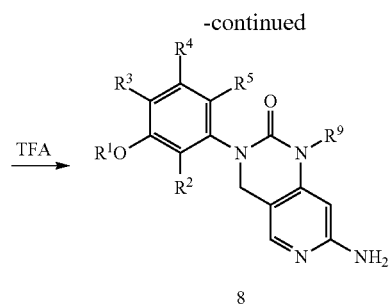 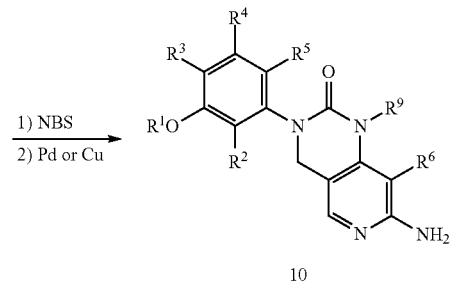

Compounds of formula 26 can be prepared by the methods outlined in Scheme 5. Lactam 24 can be prepared from compounds 22 and 23 using Palladium-catalyzed Buchwald-Hartwig-type reactions or copper-mediated Ullmann-type and Chan-Lam-type N-arylation reactions. α-Substituted lactam 25 can be obtained by treating compound 24 with a base such as, for example, $K_2CO_3$ or $Cs_2CO_3$ in DMF or acetonitrile, and followed by the addition of halides $R^{10}X$ and/or $R^{11}X$ (X is halo such as Cl or Br). Chloride 25 can be converted to the corresponding aminopyridine 26 under Buchwald-Hartwig amination conditions using reagents such as, for example, $Pd(OAc)_2$/Xantphos/$Cs_2CO_3$ or $Pd_2(dba)_3$/BINAP/NaOtBu, etc.

Scheme 5

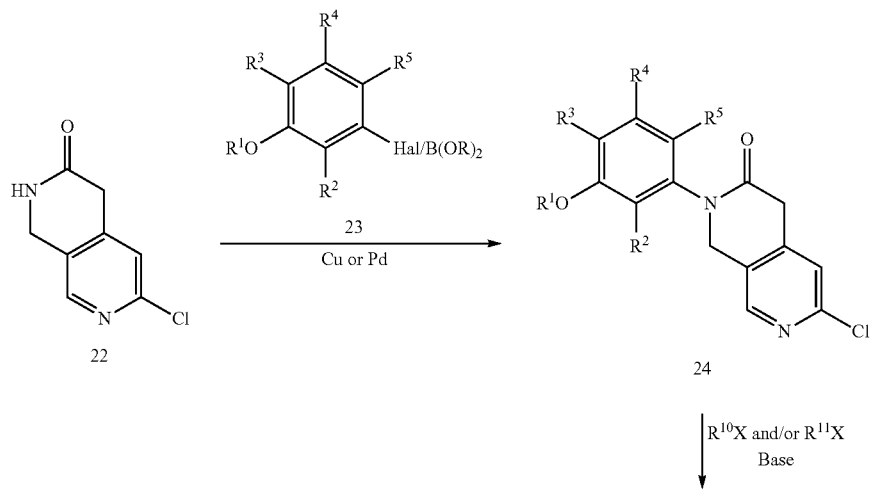

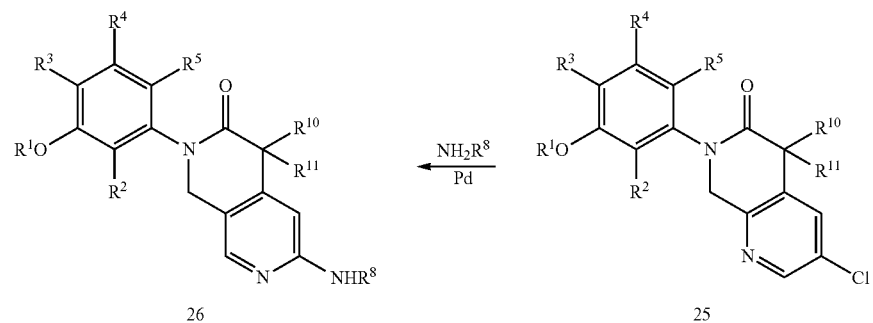

Compounds of formula 34 can be prepared by the methods outlined in Scheme 6. Ester 27 can be prepared by selective displacement of chloride with sodium allyloxide. The resulting ester 27 is subjected to a reduction-oxidation sequence to afford aldehyde 28. Example reducing reagents include DIBAL-H (diisobutylaluminium hydride), LAH (lithium aluminium hydride), Super-H (lithium triethylborohydride), etc; and example oxidants include Dess-Martin Periodinane, $MnO_2$, Swern Oxidation, etc. The aniline compound 29 is synthesized by coupling aldehyde 28 and aniline 4 through reductive amination. After the removal of allyl group by palladium dichloride, then cyclization of amino hydroxyl intermediate can be carried out with triphosgene or the equivalent such as carbonyldiimidazole (CDI), phosgene, diphosgene, etc. affording the bicyclic carbamate derivatives of formula 30. The synthesis of compound 34 from carbamate 30 follows the same procedure as described in Scheme 1.

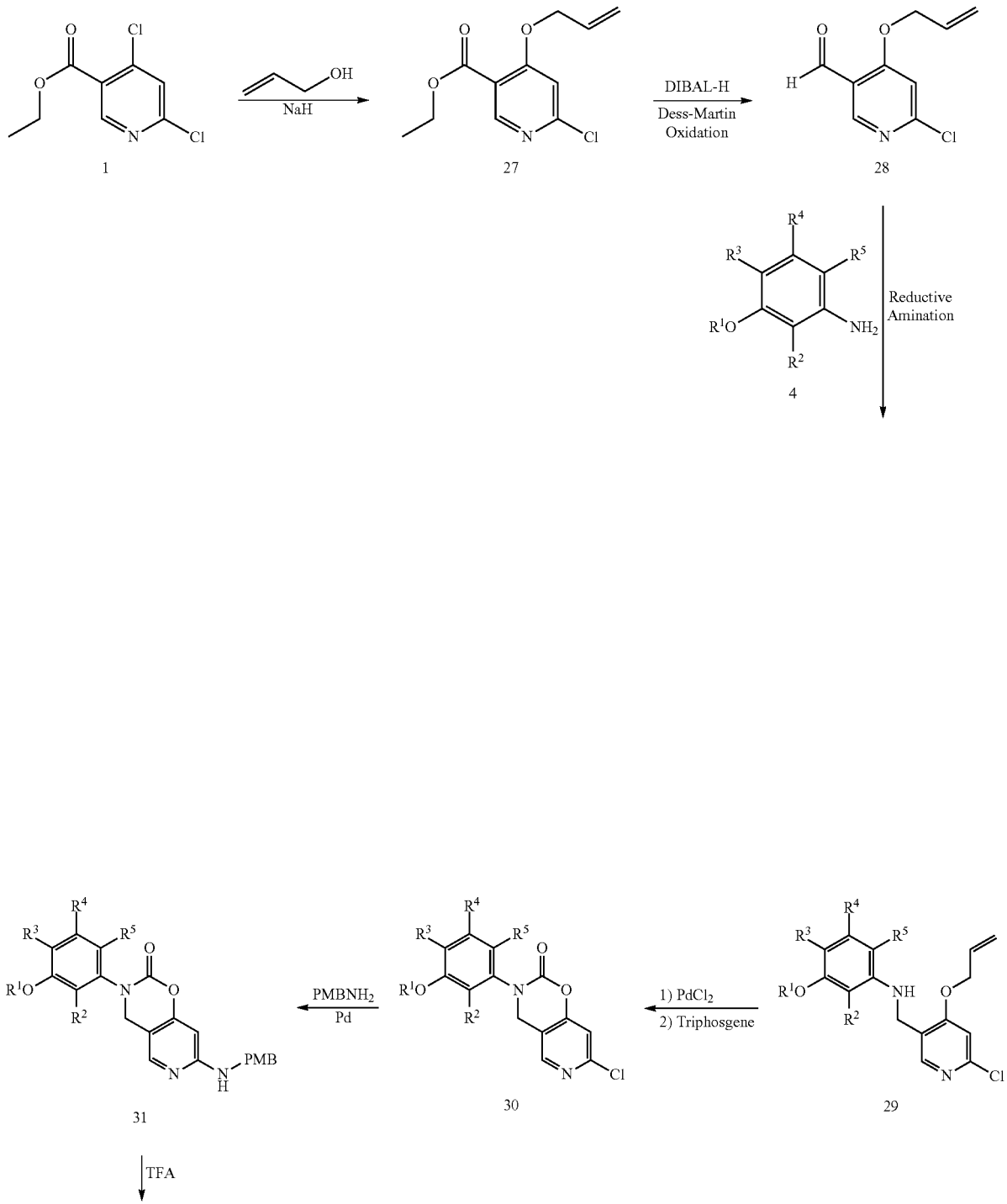

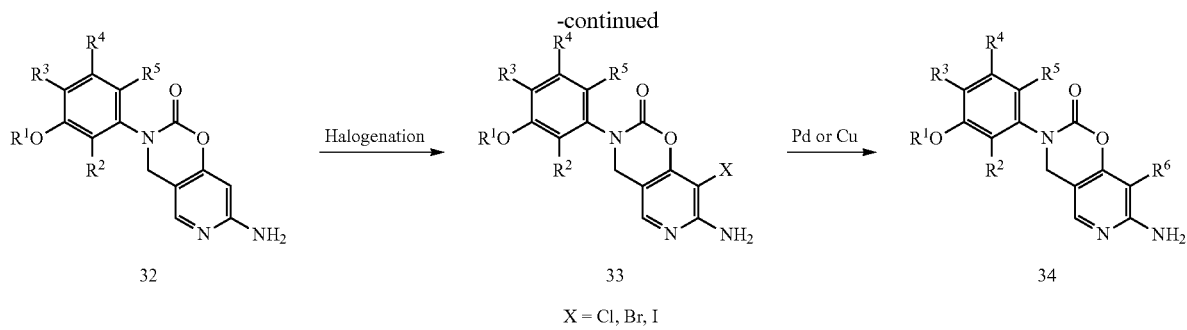

32 → 33 → 34

X = Cl, Br, I

An alternative synthesis of compound 26 is outlined in Scheme 7. Ester 1 is reduced to the corresponding aldehyde 19. Then reductive amination of aldehyde 19 with aniline 4 affords compound 20, which can be treated with ethyl 3-chloro-3-oxopropanoate in the presence of NaH in THF to provide intermediate aniline 35. Lactam 24 can be prepared by treatment of compound 35 with a strong base such as, but not limited to, NaH or $Cs_2CO_3$ in DMF, then followed by an acid, for example, HCl mediated decarboxylation. α-Substituted lactam 25 can be obtained by treating compound 24 with a suitable base such as, NaH or $Cs_2CO_3$ in DMF and followed by the addition of halides $R^{10}X$ and/or $R^{11}X$ (X is halo such as Cl or Br). Chloride 25 can be converted to the corresponding aminopyridine 26 under Buchwald-Hartwig amination conditions using reagents such as, but not limited to, $Pd(OAc)_2$/Xantphos/$Cs_2CO_3$ or $Pd(OAc)_2$/BrettPhos/NaOtBu.

Scheme 7

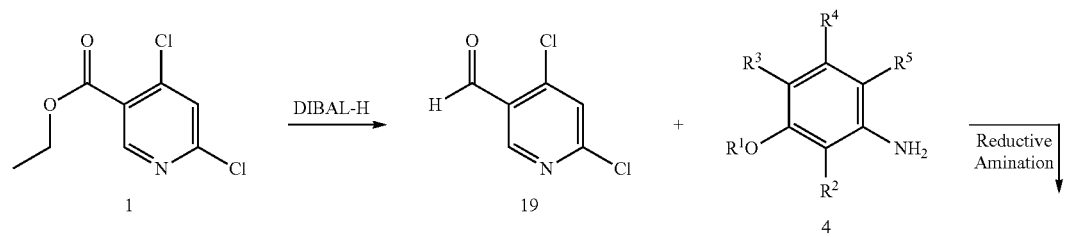

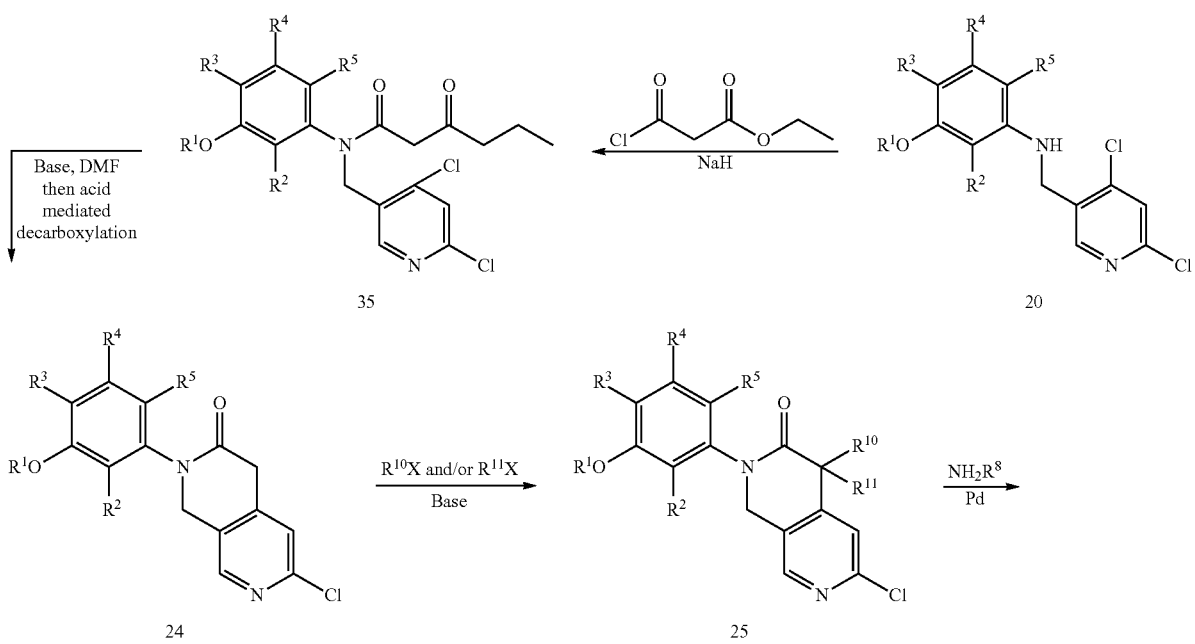

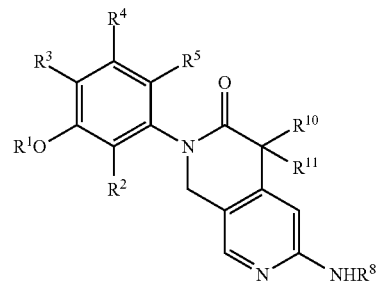

26

Methods of Use

Compounds of the invention can inhibit activity of one or more FGFR enzymes. For example, the compounds of the invention can be used to inhibit activity of an FGFR enzyme in a cell or in an individual or patient in need of inhibition of the enzyme by administering an inhibiting amount of a compound of the invention to the cell, individual, or patient.

In some embodiments, the compounds of the invention are inhibitors of one or more of FGFR1, FGFR2, FGFR3, and FGFR4. In some embodiments, the compounds of the invention inhibit each of FGFR1, FGFR2, and FGFR3. In some embodiments, the compounds of the invention are selective for one or more FGFR enzymes. In some embodiments, the compounds of the invention are selective for one or more FGFR enzymes over VEGFR2. In some embodiments, the selectivity is 2-fold or more, 3-fold or more, 5-fold or more, 10-fold or more, 50-fold or more, or 100-fold or more.

As FGFR inhibitors, the compounds of the invention are useful in the treatment of various diseases associated with abnormal expression or activity of FGFR enzymes or FGFR ligands.

For example, the compounds of the invention are useful in the treatment of cancer. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with the compounds of the invention include tumors of the eye, glioblastoma, melanoma, rhabdosarcoma, lymphosarcoma, and osteosarcoma.

In addition to oncogenic neoplasms, the compounds of the invention can be useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes.

The compounds of the invention can also be useful in the treatment of hypophosphatemia disorders including, for example, X-linked hypophosphatemic rickets, autosomal recessive hypophosphatemic rickets, autosomal dominant hypophosphatemic rickets, and tumor-induced osteromalacia.

The compounds of the invention may further be useful in the treatment of fibrotic diseases, such as where a disease symptom or disorder is characterized by fibrosis. Example fibrotic diseases include liver cirrhosis, glomerulonephritis, pulmonary fibrosis, systemic fibrosis, rheumatoid arthritis, and wound healing.

The compounds of the invention can also be useful in the treatment of psoriasis, keloids, bullous skin disorders, atherosclerosis, restenosis, mesangial cell proliferative disorders, glomerulopathy, diabetic nephropathy, kidney diseases, and benign prostate hyperplasia.

The compounds of the invention can also be useful in the treatment of various eye diseases including, for example, age-related macular degeneration, dry macular degeneration, ischemic retinal vein occlusion, diabetic macula edema, diebetic retinopathy, and retinopathy of prematurity.

The compounds of the invention can also be useful in the inhibition of tumor metastisis.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound of the invention includes the administration of a compound of the present invention to an individual or patient, such as a human, having FGFR, as well as, for example, introducing a compound of the invention into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 2) inhibiting the disease; for example, inhibiting a disease, condition or disorder in an individual who is experiencing or displaying the pathology or symptomatology of the disease, condition or disorder (i.e., arresting further development of the pathology and/or symptomatology), or 3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of the present invention for treatment of FGFR-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compounds of the present invention may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present invention include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds of the present invention. In some embodiments, the JAK inhibitor is selective for JAK1 over JAK2 and JAK3.

Other suitable agents for use in combination with the compounds of the present invention include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the FGFR enzyme in tissue samples, including human, and for identifying FGFR enzyme ligands by inhibition binding of a labeled compound. Accordingly, the present invention includes FGFR enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro FGFR enzyme labeling and competition assays, compounds that incorporate $^3$H, $^{14}$C, $^{82}$Br, $^{125}$I $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the FGFR enzyme. Accordingly, the ability of a test compound to compete with the radio-labeled compound for binding to the FGFR enzyme directly correlates to its binding affinity.

Kits

The present invention also includes pharmaceutical kits useful, for example, in the treatment or prevention of FGFR-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more FGFR's as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Hague, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the 30×100 mm column was 60 mL/minute.

pH=10 purifications: Waters XBridge $C_{18}$ 5 μm, 19×100 mm column, eluting with mobile phase A: 0.15% NH$_4$OH in water and mobile phase B: 0.15% NH$_4$OH in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute.

Example 1

7-amino-3-(2,6-difluoro-3,5-dimethoxyphenyl)-1,8-dimethyl-3,4-dihydropyrido[4,3-d]pyrimidin-2(1H)-one

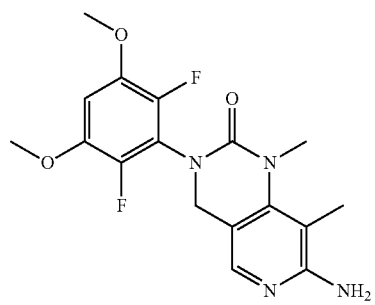 [SMILES: COc1cc(OC)c(F)c(N2Cc3cnc(N)c(C)c3N(C)C2=O)c1F]

Step 1: ethyl 6-chloro-4-(methylamino)nicotinate

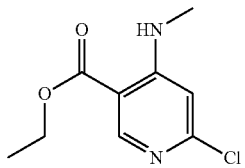

To a solution of 2,4-dichloro-5-carbethoxypyridine (10.0 g, 45.4 mmol, purchased from Ark, catalog No. AK-25933) in acetonitrile (40 mL) was added methylamine (8.52 mL, 8.0 M in EtOH, 68.2 mmol) dropwise at 0° C. The resulting solution was stirred at room temperature for 6 h before it was concentrated in vacuo. The crude residue was taken to the next step directly without further purification. LC-MS calculated for $C_9H_{12}ClN_2O_2$ [M+H]$^+$ m/z: 215.1. found 215.1.

Step 2: 6-chloro-4-(methylamino)nicotinaldehyde

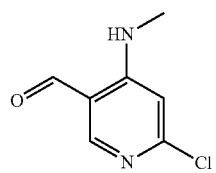

To a solution of ethyl 6-chloro-4-(methylamino)nicotinate (11.0 g, 50.2 mmol) in methylene chloride (400 mL) was added 1.0 M diisobutylaluminum hydride in THF (150 mL, 150 mmol). The resulting mixture was stirred at room temperature for 6 h before it was quenched by a solution of Rochelle's salt. After stirring for 12 h, the aqueous solution was extracted with EtOAc (3×150 mL) and the organic layer was dried over $Na_2SO_4$ and concentrated in vacuo to afford the crude alcohol. LC-MS calculated for $C_7H_{10}ClN_2O$ [M+H]$^+$ m/z: 173.0. found 173.0. To the solution of crude alcohol in methylene chloride (300 mL) were added sodium bicarbonate (42 g, 500 mmol) and Dess-Martin periodinane (42 g, 100 mmol). The resulting mixture was stirred for 1 h before it was quenched with $Na_2S_2O_3$ (sat. aq, 100 mL) and $NaHCO_3$ (sat. aq, 100 mL). The aqueous phase was extracted with EtOAc (3×100 mL) and the organic layer was dried over $Na_2SO_4$ and concentrated in vacuo. Purified by flash column chromatography to afford the the aldehyde (6.2 g, 80% yield over two steps). LC-MS calculated for $C_7H_8ClN_2O$ [M+H]$^+$ m/z: 171.0. found 171.0.

Step 3: 2-chloro-5-{[(2,6-difluoro-3,5-dimethoxyphenyl)amino]methyl}-N-methylpyridin-4-amine

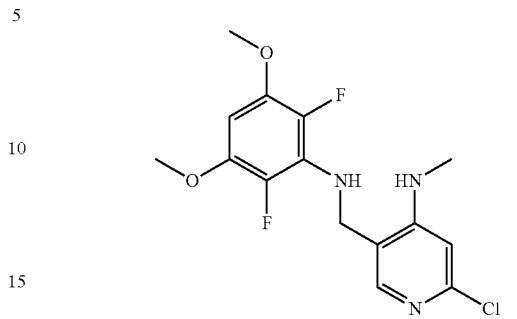

To a mixture of 2,6-difluoro-3,5-dimethoxyaniline (CAS #651734-54-2, LakeStar Tech, LSP-210C, Lot: 132-110-05: 1.07 g, 5.68 mmol) in trifluoroacetic acid (7.9 mL, 0.1 mol) was added sodium triacetoxyborohydride (3.6 g, 17.0 mmol). The mixture was stirred at 0° C. for 2 minutes before a solution of 6-chloro-4-(methylamino)-nicotinaldehyde (0.97 g, 5.7 mmol) in methylene chloride (8.0 mL) was added dropwise. The reaction mixture was stirred at room temperature overnight before it was concentrated in vacuo to remove the excess trifluoroacetic acid. The residue was neutralized by $NaHCO_3$ solution. The aqueous phase was extracted with EtOAc (3×10 mL) and the organic layer was dried over $Na_2SO_4$ and concentrated in vacuo. The crude product was purified by flash column chromatography to afford the aniline (1.36 g, 68%). LC-MS calculated for $C_{15}H_{17}ClF_2N_3O_2$ [M+H]$^+$ m/z: 344.1. found 344.1.

Step 4: 7-chloro-3-(2,6-difluoro-3,5-dimethoxyphenyl)-1-methyl-3,4-dihydropyrido[4,3-d]pyrimidin-2(1H)-one

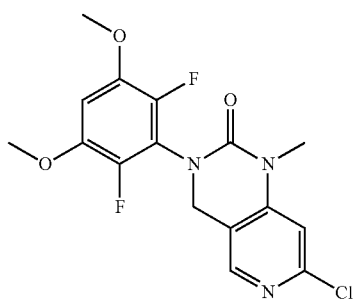 [SMILES: COc1cc(OC)c(F)c(N2Cc3cnc(Cl)cc3N(C)C2=O)c1F]

To a mixture of dianiline (206 mg, 0.60 mmol) in THF (6.0 mL) were added triethylamine (0.41 mL, 2.9 mmol) and triphosgene (70.0 mg, 0.23 mmol) at 0° C. The resulting mixture was stirred for 1 h at 0° C. before it was quenched with sodium carbonate. The aqueous phase was extracted with EtOAc (3×10 mL) and the organic layer was dried over $Na_2SO_4$ and concentrated in vacuo. The crude product was purified by flash column chromatography to afford the urea (190 mg, 90%). LC-MS calculated for $C_{16}H_{15}ClF_2N_3O_3$ [M+H]$^+$ m/z: 370.1. found 370.1.

Step 5: 3-(2,6-difluoro-3,5-dimethoxyphenyl)-7-[(4-methoxybenzyl)amino]-1-methyl-3,4-dihydropyrido[4,3-d]pyrimidin-2(1H)-one

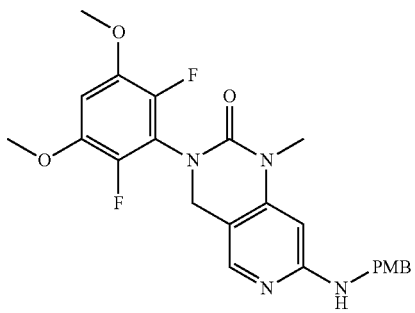

To a mixture of 4-methoxybenzylamine (2.65 mL, 20.3 mmol), 7-chloro-3-(2,6-difluoro-3,5-dimethoxyphenyl)-1-methyl-3,4-dihydropyrido[4,3-d]pyrimidin-2(1H)-one (1.5 g, 4.0 mmol), palladium acetate (90 mg, 0.4 mmol), (R)-(+)-2,2'-bis(diphenylphosphino)-1,1'-binaphthyl (200 mg, 0.4 mmol) and cesium carbonate (2.6 g, 8.1 mmol) in 1,4-dioxane (30 mL, 400 mmol) was heated at 100° C. for 12 h. The mixture was filtered and concentrated in vacuo. The crude product was purified by flash column chromatography to afford the aniline. LC-MS calculated for $C_{24}H_{25}F_2N_4O_4$ [M+H]+ m/z: 471.2. found 471.2.

Step 6: 7-amino-3-(2,6-difluoro-3,5-dimethoxyphenyl)-1-methyl-3,4-dihydropyrido[4,3-d]pyrimidin-2(1H)-one

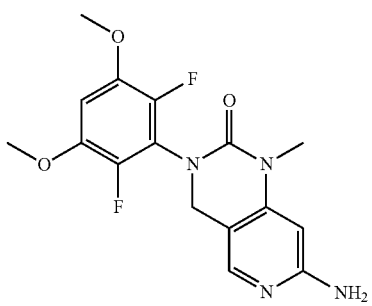 [SMILES: COc1cc(OC)c(F)c(N2Cc3cnc(N)cc3N(C)C2=O)c1F]

A solution of 3-(2,6-difluoro-3,5-dimethoxyphenyl)-7-[(4-methoxybenzyl)amino]-1-methyl-3,4-dihydropyrido[4,3-d]pyrimidin-2(1H)-one (1.1 g, 2.3 mmol) in TFA (10.0 mL) was heated to 85° C. for 3 h before it was concentrated in vacuo and neutralized with sodium bicarbonate solution. The aqueous phase was extracted with EtOAc (3×20 mL) and the organic layer was dried over $Na_2SO_4$ and concentrated in vacuo. The crude product was purified by flash column chromatography to afford the aniline (0.55 g, 67%). LC-MS calculated for $C_{16}H_{17}F_2N_4O_3$ [M+H]+ m/z: 351.1. found 351.1.

Step 7: 7-amino-8-bromo-3-(2,6-difluoro-3,5-dimethoxyphenyl)-1-methyl-3,4-dihydropyrido[4,3-d]pyrimidin-2(1H)-one

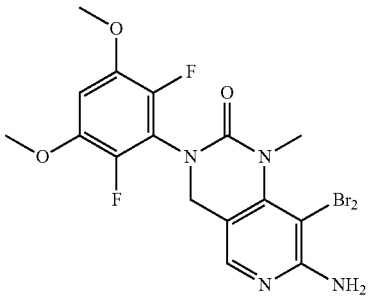

To a solution of 7-amino-3-(2,6-difluoro-3,5-dimethoxyphenyl)-1-methyl-3,4-dihydropyrido[4,3-d]pyrimidin-2(1H)-one (37 mg, 0.106 mmol) in acetonitrile (2.0 mL) was added NBS (23 mg, 0.13 mmol). The resulting mixture was stirred for 1 h before it was concentrated in vacuo. The crude product was purified by flash column chromatography to afford the bromide. LC-MS calculated for $C_{16}H_{16}BrF_2N_4O_3$ [M+H]+ m/z: 429.1. found 429.1.

Step 8: 7-amino-3-(2,6-difluoro-3,5-dimethoxyphenyl)-1,8-dimethyl-3,4-dihydropyrido[4,3-d]pyrimidin-2 (1H)-one To a solution of 7-amino-8-bromo-3-(2,6-difluoro-3,5-dimethoxyphenyl)-1-methyl-3,4-dihydropyrido[4,3-d]pyrimidin-2(1H)-one (34.0 mg, 0.080 mmol) in 1,4-dioxane (0.8 mL) were added $Pd(dppf)Cl_2$ (8.0 mg, 0.01 mmol) and $ZnMe_2$ (2.0 M solution in toluene, 0.11 mL, 0.22 mmol). The resulting mixture was stirred for 1 h at 110° C. before it was diluted with MeOH (4 mL) and purified by RP-HPLC (pH 2) to afford the product as its TFA salt. LC-MS calculated for $C_{17}H_{19}F_2N_4O_3$ [M+H]+ m/z: 365.1. found 365.1. $^1$H NMR (500 MHz, DMSO) δ 7.73 (s, 3H), 7.04 (t, J=7.5 Hz, 1H), 4.59 (s, 2H), 3.88 (s, 6H), 3.39 (s, 3H), 2.80 ppm (s, 3H).

Example 2

7-amino-3-(2,6-difluoro-3,5-dimethoxyphenyl)-8-ethyl-1-methyl-3,4-dihydropyrido[4,3-d]pyrimidin-2(1H)-one

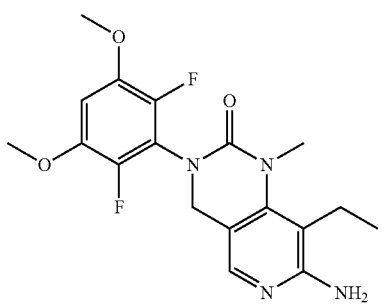 [SMILES: CCc1c(N)ncc2c1N(C)C(=O)N(c1c(F)c(OC)cc(OC)c1F)C2]

This compound was synthesized by the same method described in Example 1 by using diethylzinc (purchased from Sigma-Aldrich, catalog No. 220809) instead of dimethylzinc. LC-MS calculated for $C_{18}H_{21}F_2N_4O_3$ [M+H]$^+$ m/z: 379.1. found 379.1.

Example 3

7-amino-3-(2,6-difluoro-3,5-dimethoxyphenyl)-1-methyl-2-oxo-1,2,3,4-tetrahydropyrido-[4,3-d]pyrimidine-8-carbonitrile

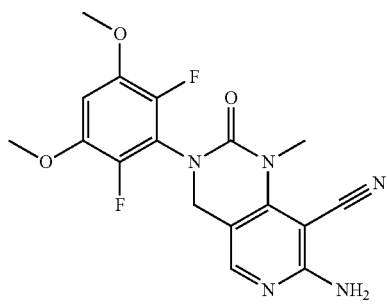 [SMILES: COc1cc(OC)c(F)c(N2Cc3cnc(N)c(C#N)c3N(C)C2=O)c1F]

To a solution of 7-amino-8-bromo-3-(2,6-difluoro-3,5-dimethoxyphenyl)-1-methyl-3,4-dihydropyrido[4,3-d]pyrimidin-2(1H)-one (10.0 mg, 0.0233 mmol) in DMF (1.0 mL) was added Pd(dppf)Cl$_2$ (4.0 mg, 0.005 mmol) and zinc cyanide (8.2 mg, 0.070 mmol). The resulting mixture was stirred for 1 h at 180° C. before it was diluted with MeOH (4 mL) and purified by RP-HPLC (pH 2) to afford the product. LC-MS calculated for $C_{17}H_{16}F_2N_5O_3$ [M+H]$^+$ m/z: 376.1. found 376.1. $^1$H NMR (500 MHz, DMSO) δ 7.90 (s, 1H), 7.15 (s, 2H), 7.05 (t, J=7.5 Hz, 1H), 4.55 (s, 2H), 3.89 (s, 6H), 3.53 ppm (s, 3H).

Example 4

7-amino-3-(2,6-difluoro-3,5-dimethoxyphenyl)-8-ethoxy-1-methyl-3,4-dihydropyrido[4,3-d]pyrimidin-2(1H)-one

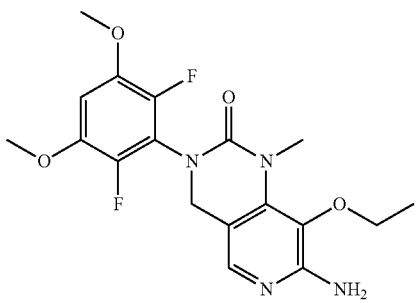 [SMILES: CCOc1c(N)ncc2c1N(C)C(=O)N(c1c(F)c(OC)cc(OC)c1F)C2]

To a solution of 7-amino-8-bromo-3-(2,6-difluoro-3,5-dimethoxyphenyl)-1-methyl-3,4-dihydropyrido[4,3-d]pyrimidin-2(1H)-one (10.0 mg, 0.0233 mmol) in ethanol (1.0 mL) were added copper (10.0 mg, 0.157 mmol) and potassium hydroxide (10.0 mg, 0.178 mmol). The resulting mixture was heated to 150° C. for 3 h and then diluted with MeOH (4 mL) and purified by RP-HPLC (pH 2). LC-MS calculated for $C_{18}H_{21}F_2N_4O_4$ [M+H]$^+$ m/z: 395.1. found 395.1. $^1$H NMR (500 MHz, DMSO) δ 7.57 (s, 1H), 7.03 (t, J=7.5 Hz, 1H), 6.48 (s, 2H), 4.58 (s, 2H), 3.88 (s, 6H), 3.82 (q, J=7.5 Hz, 2H), 3.42 (s, 3H), 1.34 ppm (t, J=7.5 Hz, 3H).

Example 5

7-amino-3-(2,6-difluoro-3,5-dimethoxyphenyl)-8-(2-methoxyethoxy)-1-methyl-3,4-dihydropyrido[4,3-d]pyrimidin-2(1H)-one

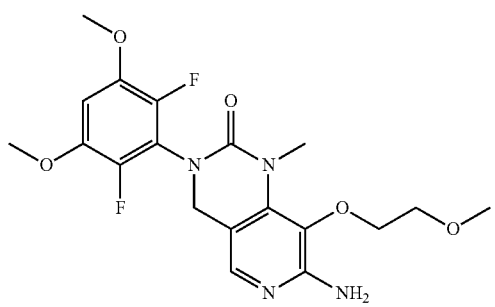

This compound was synthesized by the same method described in Example 4 by using 2-methoxyethanol instead of ethanol. LC-MS calculated for $C_{19}H_{23}F_2N_4O_5$ [M+H]$^+$ m/z: 424.2. found 424.1.

Example 6

7-amino-3-(2,6-difluoro-3,5-dimethoxyphenyl)-1-methyl-8-[2-(4-methylpiperazin-1-yl)ethoxy]-3,4-dihydropyrido[4,3-d]pyrimidin-2(1H)-one

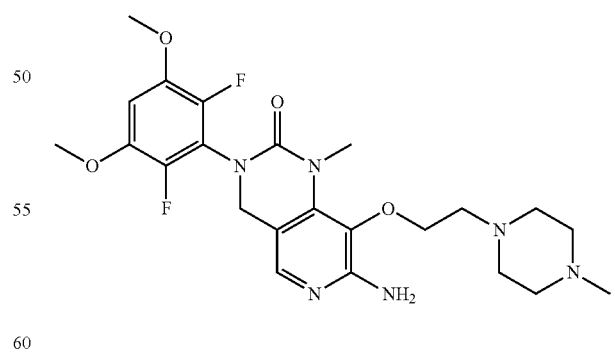

This compound was synthesized by the same method described in Example 4 by using 2-(4-methylpiperazin-1-yl)ethanol (purchased from Oakwood, catalog No. 021290) instead of ethanol. LC-MS calculated for $C_{23}H_{31}F_2N_6O_4$ [M+H]$^+$ m/z: 493.2. found 493.2.

Example 7

7-amino-3-(2,6-difluoro-3,5-dimethoxyphenyl)-1-methyl-8-phenoxy-3,4-dihydropyrido[4,3-d]pyrimidin-2(1H)-one

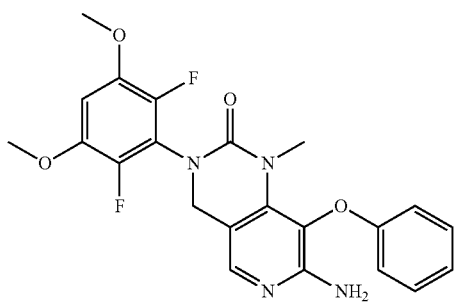 [SMILES: COc1cc(OC)c(F)c(N2Cc3cnc(N)c(Oc4ccccc4)c3N(C)C2=O)c1F]

This compound was synthesized by the same method described in Example 4 by using phenol instead of ethanol. LC-MS calculated for $C_{22}H_{21}F_2N_4O_4$ [M+H]$^+$ m/z: 443.1. found 443.1.

Example 8

7-amino-3-(2,6-difluoro-3,5-dimethoxyphenyl)-1-methyl-8-(1-methyl-1H-pyrazol-4-yl)-3,4-dihydropyrido[4,3-d]pyrimidin-2(1H)-one

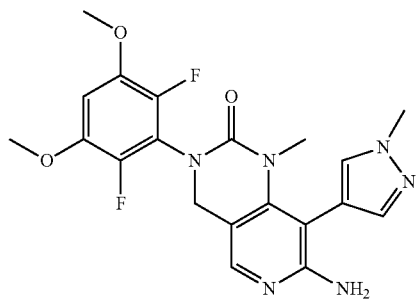 [SMILES: COc1cc(OC)c(F)c(N2Cc3cnc(N)c(-c4cnn(C)c4)c3N(C)C2=O)c1F]

To a solution of 7-amino-8-bromo-3-(2,6-difluoro-3,5-dimethoxyphenyl)-1-methyl-3,4-dihydropyrido[4,3-d]pyrimidin-2(1H)-one (Example 1, Step 7: 9.0 mg, 0.021 mmol) and 1-methyl-4-(4,4,5,5-tetramethyl-1,3,2-dioxaborolan-2-yl)-4,5-dihydro-1H-pyrazole (6.5 mg, 0.031 mmol, purchased from Sigma-Aldrich, catalog No. 595314) in 1,4-dioxane (0.6 mL) water (0.15 mL) were added potassium carbonate (8.6 mg, 0.062 mmol) and tetrakis(triphenylphosphine)palladium(0) (3.6 mg, 0.0031 mmol). The resulting mixture was stirred for 2 h at 110° C. before it was diluted with MeOH (4 mL) and purified by RP-HPLC (pH 2) to give the product as its TFA salt. LC-MS calculated for $C_{20}H_{21}F_2N_6O_3$ [M+H]$^+$ m/z: 431.2. found 431.1. $^1$H NMR (500 MHz, DMSO) δ 7.87 (s, 1H), 7.81 (s, 1H), 7.49 (s, 1H), 7.20 (s, 2H), 7.04 (t, J=7.5 Hz, 1H), 4.61 (s, 2H), 3.90 (s, 3H), 3.88 (s, 6H), 2.67 ppm (s, 3H).

Example 9

7-amino-3-(2,6-difluoro-3,5-dimethoxyphenyl)-1-methyl-8-(1-ethyl-1H-pyrazol-4-yl)-3,4-dihydropyrido[4,3-d]pyrimidin-2(1H)-one

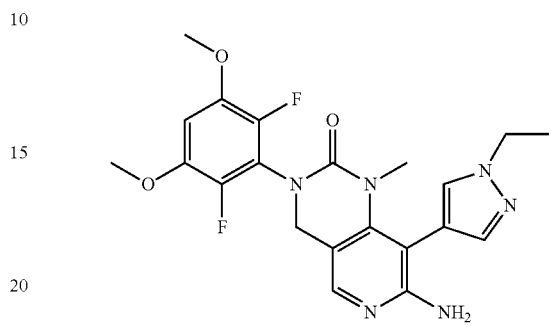

This compound was synthesized by the same method described in Example 8 by using 1-ethyl-4-(4,4,5,5-tetramethyl-1,3,2-dioxaborolan-2-yl)-4,5-dihydro-1H-pyrazole (purchased from Combi-Blocks, catalog No. BB-8817) instead of 1-methyl-4-(4,4,5,5-tetramethyl-1,3,2-dioxaborolan-2-yl)-4,5-dihydro-1H-pyrazole. LC-MS calculated for $C_{21}H_{23}F_2N_6O_3$ [M+H]$^+$ m/z: 443.2. found 443.1.

Example 10

7-amino-3-(2,6-difluoro-3,5-dimethoxyphenyl)-8-[1-(2-hydroxyethyl)-1H-pyrazol-4-yl]-1-methyl-3,4-dihydropyrido[4,3-d]pyrimidin-2(1H)-one

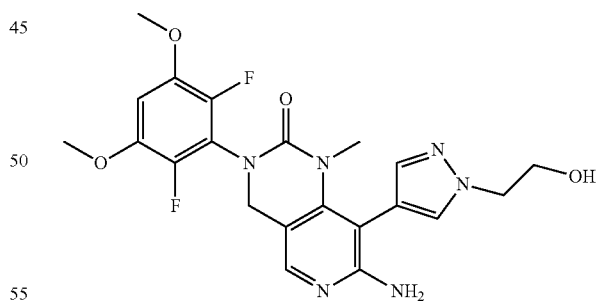

This compound was synthesized by the same method described in Example 8 by using 2-[4-(4,4,5,5-tetramethyl-1,3,2-dioxaborolan-2-yl)-4,5-dihydro-1H-pyrazol-1-yl]ethanol instead of 1-methyl-4-(4,4,5,5-tetramethyl-1,3,2-dioxaborolan-2-yl)-4,5-dihydro-1H-pyrazole (purchased from Syntech Solution, catalog No. BH-3012). LC-MS calculated for $C_{21}H_{23}F_2N_6O_3$ [M+H]$^+$ m/z: 461.2. found 461.2.

Example 11

7-amino-3-(2,6-difluoro-3,5-dimethoxyphenyl)-1-methyl-8-(1-piperidin-4-yl-1H-pyrazol-4-yl)-3,4-dihydropyrido[4,3-d]pyrimidin-2(1H)-one

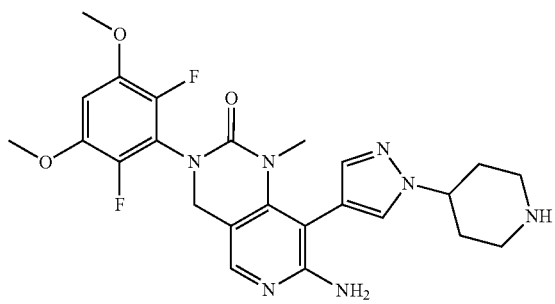 [SMILES: COc1cc(OC)c(F)c(N2Cc3cnc(N)c(-c4cnn(C5CCNCC5)c4)c3N(C)C2=O)c1F]

This compound was synthesized by the same method described in Example 8 by using {1-[1-(tert-butoxycarbonyl)piperidin-4-yl]-4,5-dihydro-1H-pyrazol-4-yl}boronic acid (purchased from Combi-Blocks, catalog No. BB-6007) instead of 1-methyl-4-(4,4,5,5-tetramethyl-1,3,2-dioxaborolan-2-yl)-4,5-dihydro-1H-pyrazole. After the reaction was completed, it was diluted with TFA (4 mL) and purified by RP-HPLC to afford the product. LC-MS calculated for $C_{24}H_{28}F_2N_7O_3$ $[M+H]^+$ m/z: 500.2. found 500.1.

Example 12

7-amino-3-(2,6-difluoro-3,5-dimethoxyphenyl)-1-methyl-8-(1H-pyrazol-4-yl)-3,4-dihydropyrido[4,3-d]pyrimidin-2(1H)-one

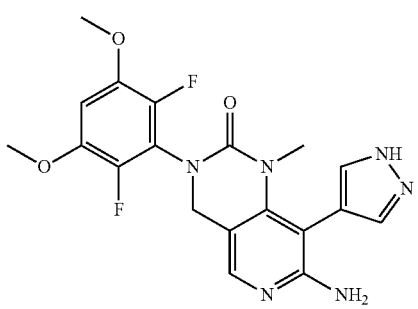 [SMILES: COc1cc(OC)c(F)c(N2Cc3cnc(N)c(-c4cn[nH]c4)c3N(C)C2=O)c1F]

This compound was synthesized by the same method described in Example 8 by using 4-(4,4,5,5-tetramethyl-1,3,2-dioxaborolan-2-yl)-1H-pyrazole (purchased from Sigma-Aldrich, catalog No. 525057) instead of 1-methyl-4-(4,4,5,5-tetramethyl-1,3,2-dioxaborolan-2-yl)-4,5-dihydro-1H-pyrazole. LC-MS calculated for $C_{19}H_{19}F_2N_6O_3$ $[M+H]^+$ m/z: 417.1. found 417.1.

Example 13

7-amino-3-(2,6-difluoro-3,5-dimethoxyphenyl)-1-methyl-8-(1-methyl-1H-pyrazol-5-yl)-3,4-dihydropyrido[4,3-d]pyrimidin-2(1H)-one

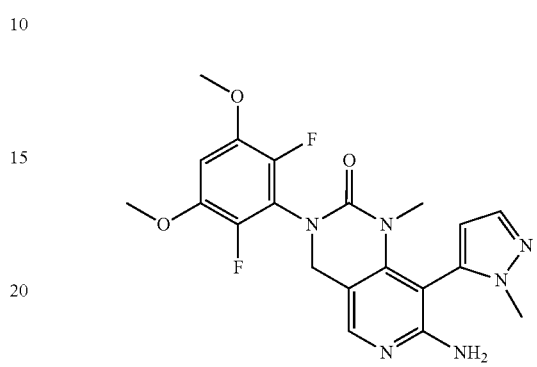

This compound was synthesized by the same method described in Example 8 by using 1-methyl-5-(4,4,5,5-tetramethyl-1,3,2-dioxaborolan-2-yl)-1H-pyrazole (purchased from ChemBridge Corp., catalog No. 4003213) instead of 1-methyl-4-(4,4,5,5-tetramethyl-1,3,2-dioxaborolan-2-yl)-4,5-dihydro-1H-pyrazole. LC-MS calculated for $C_{20}H_{21}F_2N_6O_3$ $[M+H]^+$ m/z: 431.2. found 431.1.

Example 14

7-amino-3-(2,6-difluoro-3,5-dimethoxyphenyl)-1-methyl-8-phenyl-3,4-dihydropyrido[4,3-d]pyrimidin-2(1H)-one

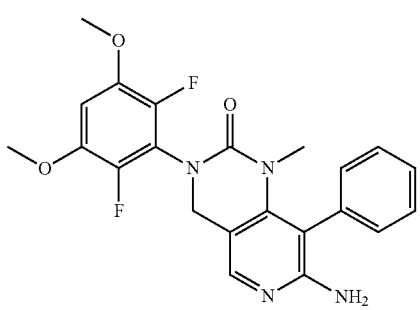 [SMILES: COc1cc(OC)c(F)c(N2Cc3cnc(N)c(-c4ccccc4)c3N(C)C2=O)c1F]

This compound was synthesized by the same method described in Example 8 by using phenylboronic acid (purchased from Sigma-Aldrich, catalog No. 20009) instead of 1-methyl-4-(4,4,5,5-tetramethyl-1,3,2-dioxaborolan-2-yl)-4,5-dihydro-1H-pyrazole. LC-MS calculated for $C_{22}H_{21}F_2N_4O_3$ $[M+H]^+$ m/z: 427.2. found 427.1.

Example 15

7-amino-3-(2,6-difluoro-3,5-dimethoxyphenyl)-8-(4-fluorophenyl)-1-methyl-3,4-dihydro-pyrido[4,3-d]pyrimidin-2(1H)-one

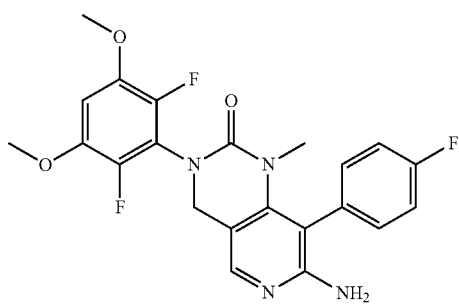 [SMILES: COc1cc(OC)c(F)c(N2Cc3cnc(N)c(-c4ccc(F)cc4)c3N(C)C2=O)c1F]

This compound was synthesized by the same method described in Example 8 by using 4-fluorophenylboronic acid (purchased from Sigma-Aldrich, catalog No. 417556) instead of 1-methyl-4-(4,4,5,5-tetramethyl-1,3,2-dioxaborolan-2-yl)-4,5-dihydro-1H-pyrazole. LC-MS calculated for $C_{22}H_{20}F_3N_4O_3$ $[M+H]^+$ m/z: 445.1. found 445.1.

Example 16

7-amino-3-(2,6-difluoro-3,5-dimethoxyphenyl)-1-methyl-8-pyridin-3-yl-3,4-dihydropyrido[4,3-d]pyrimidin-2(1H)-one

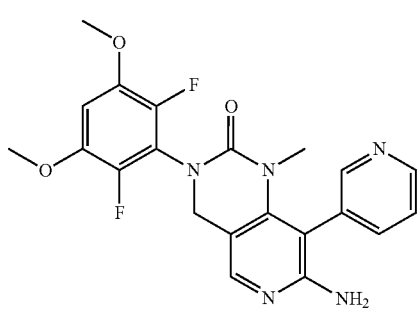 [SMILES: COc1cc(OC)c(F)c(N2Cc3cnc(N)c(-c4cccnc4)c3N(C)C2=O)c1F]

This compound was synthesized by the same method described in Example 8 by using 3-pyridylboronic acid (purchased from Sigma-Aldrich, catalog No. 512125) instead of 1-methyl-4-(4,4,5,5-tetramethyl-1,3,2-dioxaborolan-2-yl)-4,5-dihydro-1H-pyrazole. LC-MS calculated for $C_{21}H_{20}F_2N_5O_3$ $[M+H]^+$ m/z: 428.1. found 428.1.

Example 17

7-amino-3-(2,6-difluoro-3,5-dimethoxyphenyl)-1-methyl-8-pyridin-4-yl-3,4-dihydropyrido[4,3-d]pyrimidin-2(1H)-one

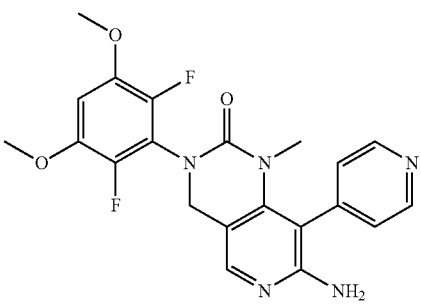 [SMILES: COc1cc(OC)c(F)c(N2Cc3cnc(N)c(-c4ccncc4)c3N(C)C2=O)c1F]

This compound was synthesized by the same method described in Example 8 by using 4-pyridylboronic acid (purchased from Sigma-Aldrich, catalog No. 634492) instead of 1-methyl-4-(4,4,5,5-tetramethyl-1,3,2-dioxaborolan-2-yl)-4,5-dihydro-1H-pyrazole. LC-MS calculated for $C_{21}H_{20}F_2N_5O_3$ $[M+H]^+$ m/z: 428.1. found 428.1.

Example 18

7-amino-3-(2,6-difluoro-3,5-dimethoxyphenyl)-1-methyl-8-[(E)-2-phenylvinyl]-3,4-dihydropyrido[4,3-d]pyrimidin-2(1H)-one

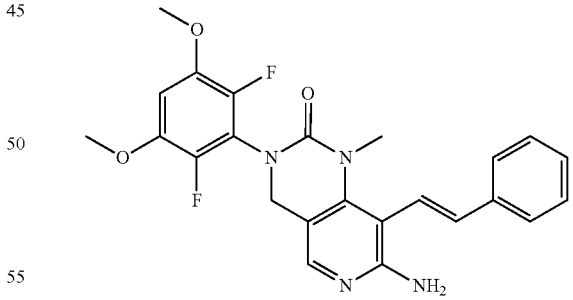

This compound was synthesized from Suzuki coupling of the bromide (Example 1, Step 7) with (E)-2-phenylvinyl boronic acid (purchased from Sigma-Aldrich, catalog No. 473790) by the same method described in Example 2. LC-MS calculated for $C_{24}H_{23}F_2N_4O_3$ $[M+H]^+$ m/z: 453.2. found 453.1.

Example 19

7-amino-3-(2,6-difluoro-3,5-dimethoxyphenyl)-1-methyl-8-phenylethyl-3,4-dihydropyrido-[4,3-d]pyrimidin-2(1H)-one

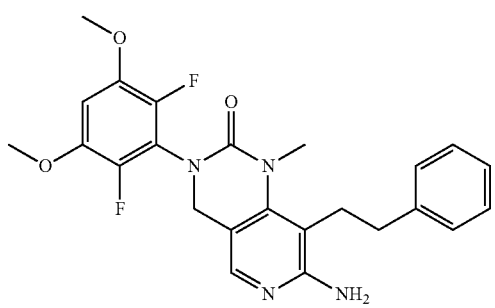 [SMILES: COc1cc(OC)c(F)c(N2Cc3cnc(N)c(CCc4ccccc4)c3N(C)C2=O)c1F]

To a solution of 7-amino-3-(2,6-difluoro-3,5-dimethoxyphenyl)-1-methyl-8-[(E)-2-phenylvinyl]-3,4-dihydropyrido[4,3-d]pyrimidin-2(1H)-one (10.0 mg) in MeOH (1 mL) was added palladium on charcoal (10.0 mg). The reaction was kept under $H_2$ atmosphere for 2 h before it was filtered, and purified by RP-HPLC (pH 2). LC-MS calculated for $C_{24}H_{25}F_2N_4O_3$ $[M+H]^+$ m/z: 455.2. found 455.1.

Example 20

7-amino-8-benzyl-3-(2,6-difluoro-3,5-dimethoxyphenyl)-1-methyl-3,4-dihydropyrido[4,3-d]pyrimidin-2(1H)-one

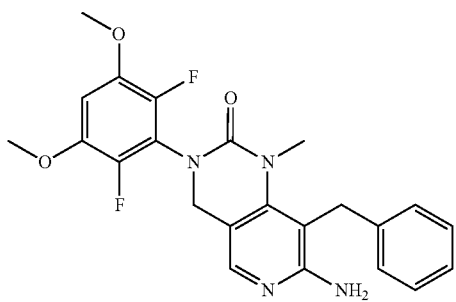

This compound was synthesized from Suzuki coupling of the bromide (Example 1, Step 7) with 2-benzyl-4,4,5,5-tetramethyl-1,3,2-dioxaborolane (purchased from Ark, catalog No. AK-23881) by the same method described in Example 2. LC-MS calculated for $C_{23}H_{23}F_2N_4O_3$ $[M+H]^+$ m/z: 441.1. found 441.1.

Example 21

7-amino-3-(2,6-difluoro-3,5-dimethoxyphenyl)-8-(3,6-dihydro-2H-pyran-4-yl)-1-methyl-3,4-dihydropyrido[4,3-d]pyrimidin-2(1H)-one

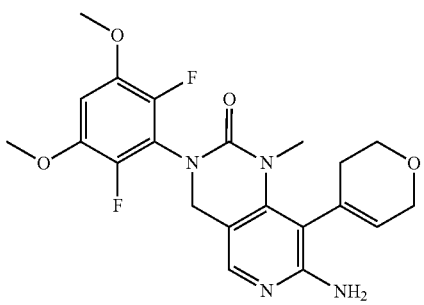 [SMILES: COc1cc(OC)c(F)c(N2Cc3cnc(N)c(C4=CCOCC4)c3N(C)C2=O)c1F]

This compound was synthesized from Suzuki coupling of the bromide (Example 1, Step 7) with 4-(4,4,5,5-tetramethyl-1,3,2-dioxaborolan-2-yl)-3,6-dihydro-2H-pyran (purchased from Sigma-Aldrich, catalog No. 721352) by the same method described in Example 2. LC-MS calculated for $C_{21}H_{23}F_2N_4O_4$ $[M+H]^+$ m/z: 433.2. found 433.1.

Example 22

6-amino-2-(2,6-difluoro-3,5-dimethoxyphenyl)-4,4-dimethyl-1,2-dihydro-2,7-naphthyridin-3(4H)-one

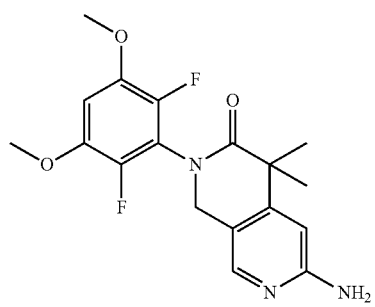 [SMILES: COc1cc(OC)c(F)c(N2Cc3cnc(N)cc3C(C)(C)C2=O)c1F]

Step 1. 6-chloro-2-(3,5-dimethoxyphenyl)-1,4-dihydro-2,7-naphthyridin-3(2H)-one

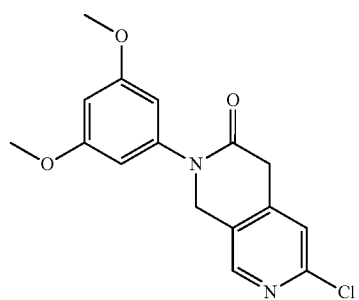 [SMILES: COc1cc(OC)cc(N2Cc3cnc(Cl)cc3CC2=O)c1]

To a stirred slurry of 6-chloro-1,4-dihydro-2,7-naphthyridin-3(2H)-one (from Anichem, cat # NC1485, 250.0 mg, 1.37 mmol) in 1,4-dioxane (3.8 mL), potassium carbonate (568 mg, 4.11 mmol), (1R,2R)—N,N'-dimethylcyclohexane-1,2-diamine (77.9 mg, 0.548 mmol), copper(I) iodide (52.1 mg, 0.274 mmol), and 3,5-dimethoxybromobenzene (446 mg, 2.05 mmol) were added sequentially at room temperature. The resulting mixture was then heated at 90° C. under the atmosphere of $N_2$. After 15 h, the reaction was quenched with saturated aq. $NH_4Cl$, and extracted with methylene chloride. The combined organic layers were dried over $MgSO_4$, and then concentrated. The residue was purified on silica gel (eluting with 0 to 0-40% EtOAc in DCM) to afford the desired product (120 mg). LC-MS calculated for $C_{16}H_{16}ClN_2O_3$ [M+H]$^+$ m/z: 319.1. found 319.1.

Step 2. 6-chloro-2-(2,6-difluoro-3,5-dimethoxyphenyl)-4,4-dimethyl-1,4-dihydro-2,7-naphthyridin-3(2H)-one

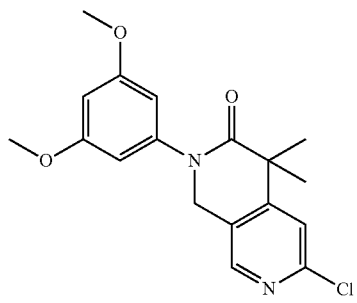 [SMILES: COc1cc(OC)cc(N2Cc3cnc(Cl)cc3C(C)(C)C2=O)c1]

To a stirred solution of 6-chloro-2-(3,5-dimethoxyphenyl)-1,4-dihydro-2,7-naphthyridin-3(2H)-one (109.0 mg, 0.342 mmol) in N,N-dimethylformamide (3.6 mL), cesium carbonate (330 mg, 1.0 mmol) and methyl iodide (53 μL, 0.85 mmol) were added sequentially at room temperature. After 5 hours, the reaction mixture was quenched with saturated aq. $NH_4Cl$, and extracted with methylene chloride. The combined organic layers were dried over $MgSO_4$, and then concentrated to afford the crude product (110 mg), which was used directly in the next step without purification. LC-MS calculated for $C_{18}H_{20}ClN_2O_3$ [M+H]$^+$ m/z: 347.1. found 347.1.

Step 3. tert-butyl [7-(3,5-dimethoxyphenyl)-5,5-dimethyl-6-oxo-5,6,7,8-tetrahydro-2,7-naphthyridin-3-yl]carbamate

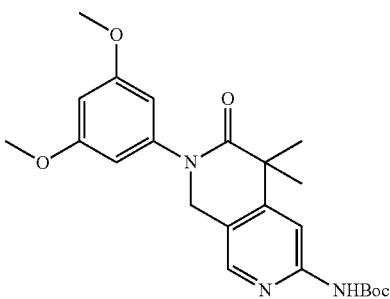 [SMILES: COc1cc(OC)cc(N2Cc3cnc(NC(=O)OC(C)(C)C)cc3C(C)(C)C2=O)c1]

A stirred mixture of 6-chloro-2-(3,5-dimethoxyphenyl)-4,4-dimethyl-1,4-dihydro-2,7-naphthyridin-3(2H)-one (100.0 mg, 0.288 mmol), t-butyl carbamate (40.5 mg, 0.346 mmol), (9,9-dimethyl-9H-xanthene-4,5-diyl)bis(diphenylphosphine) (33 mg, 0.058 mmol), palladium acetate (6.5 mg, 0.029 mmol), and cesium carbonate (93.9 mg, 0.288 mmol) in 1,4-dioxane (5 mL) was heated at 90° C. under the atmosphere of $N_2$. After 12 h, the reaction was quenched with saturated aq. $NH_4Cl$, and extracted with methylene chloride. The combined organic layers were dried over $MgSO_4$, and then concentrated. The residue was purified on silica gel (eluting with 0 to 0-40% EtOAc in DCM) to afford the desired product (22 mg). LC-MS calculated for $C_{23}H_{30}N_3O_5$ [M+H]$^+$ m/z: 428.2. found 428.2.

Step 4. 6-amino-2-(2,6-difluoro-3,5-dimethoxyphenyl)-4,4-dimethyl-1,4-dihydro-2,7-naphthyridin-3(2H)-one To a stirred solution of tert-butyl [7-(3,5-dimethoxyphenyl)-5,5-dimethyl-6-oxo-5,6,7,8-tetrahydro-2,7-naphthyridin-3-yl]carbamate (22.0 mg, 0.0515 mmol) in acetonitrile (1.5 mL), 1-(chloromethyl)-4-fluoro-1,4-diazoniabicyclo[2.2.2]octane ditetrafluoroborate (54.7 mg, 0.154 mmol) was added at 0° C. The resulted mixture was then warmed up to room temperature. After 3 hours, the reaction was quenched with saturated aq. $NaHCO_3$, and extracted with methylene chloride. The combined organic layers were dried over $MgSO_4$, concentrated to dryness, and then dissolved in trifluoroacetic acid (1.0 mL) methylene chloride (1.0 mL, 16 mmol). After 1 hour, the volatiles was removed under reduced pressure and the residue was purified on RP-HPLC (XBridge C18 column, eluting with a gradient of acetonitrile/water containing 0.05% TFA, at a flow rate of 30 mL/min) to afford the desired product (2.0 mg) as its TFA salt. LC-MS calculated for $C_{18}H_{20}F_2N_3O_3$ [M+H]$^+$ m/z: 364.1. found 364.2.

Example 23

2'-(2,6-difluoro-3,5-dimethoxyphenyl)-6'-[(2-morpholin-4-ylethyl)amino]-1',2'-dihydro-3'H-spiro[cyclopropane-1,4'-[2,7]naphthyridin]-3'-one

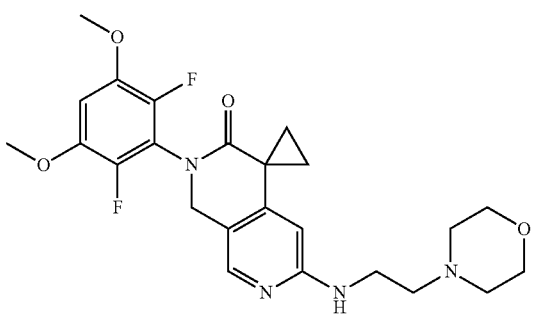 [SMILES: COc1cc(OC)c(F)c(N2Cc3cnc(NCCN4CCOCC4)cc3C3(CC3)C2=O)c1F]

Step 1: 4,6-dichloronicotinaldehyde

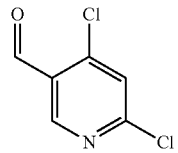

To a stirred solution of 2,4-dichloro-5-carbethoxypyridine (Ark Pharm, cat# AK-25933: 10.0 g, 45.4 mmol) in methylene chloride (100.0 mL) at −78° C. was added a solution of diisobutylaluminum hydride in methylene chloride (50.0 mL, 1.0 M, 50.0 mmol) dropwise. After 2 hours, the reaction was quenched with a saturated solution of Rochelle's salt. After stirring for 12 h, the aqueous solution was extracted with DCM (3×150 mL). The combined organic layers were dried over $Na_2SO_4$ and concentrated in vacuo to afford the crude aldehyde (7.51 g, 42.9 mmol), which was used in the next step without further purification. LC-MS calculated for $C_6H_4Cl_2NO$ [M+H]+ m/z: 176.0. found 176.0.

Step 2: N-[(4,6-dichloropyridin-3-yl)methyl]-2,6-difluoro-3,5-dimethoxyaniline

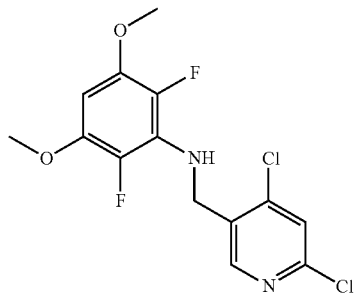 [SMILES: COc1cc(OC)c(F)c(NCc2cnc(Cl)cc2Cl)c1F]

To a stirred solution of 2,6-difluoro-3,5-dimethoxyaniline (CAS #651734-54-2, LakeStar Tech, LSP-210C, Lot: 132-110-05: 9.03 g, 47.7 mmol) and sodium triacetoxyborohydride (38.0 g, 180 mmol) in methylene chloride (60 mL) trifluoroacetic acid (30 mL) was added 4,6-dichloronicotinaldehyde (8.00 g, 45.5 mmol) in small portions at room temperature. After 1 hour, the volatiles were removed in vacuo and saturated aqueous $NaHCO_3$ (200 mL) was added. The resulting mixture was extracted with DCM (3×150 mL). The organic layers were combined, dried over $Na_2SO_4$, and concentrated. The residue was purified on silica gel (eluting with 0 to 40% EtOAc in hexanes) to afford the desired product (15.0 g). LC-MS calculated for $C_{14}H_{13}Cl_2F_2N_2O_2$ [M+H]+ m/z: 349.0. found 349.1.

Step 3: ethyl 3-[[(4,6-dichloropyridin-3-yl)methyl](2,6-difluoro-3,5-dimethoxyphenyl)amino]-3-oxopropanoate

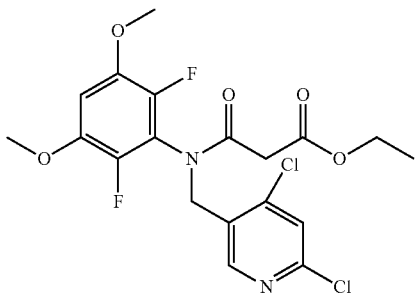 [SMILES: CCOC(=O)CC(=O)N(Cc1cnc(Cl)cc1Cl)c1c(F)c(OC)cc(OC)c1F]

To a stirred solution of N-[(4,6-dichloropyridin-3-yl)methyl]-2,6-difluoro-3,5-dimethoxyaniline (3.50 g, 10.0 mmol) in tetrahydrofuran (20 mL) was added NaH (60% w/w in mineral oil, 421 mg, 10.5 mmol) at room temperature. After 10 minutes, ethyl malonyl chloride (1.92 mL, 15.0 mmol) was added dropwise. After another 1 hour, the reaction was quenched with saturated aqueous $NH_4Cl$, and extracted with DCM (3×100 mL). The organic layers were combined, dried over $Na_2SO_4$, and concentrated. The residue was purified on silica gel (eluting with 0 to 35% EtOAc in hexanes) to afford the desired product (4.20 g, 9.1 mmol). LC-MS calculated for $C_{19}H_{19}Cl_2F_2N_2O_5$ [M+H]+ m/z: 463.1. found 463.1.

Step 4: 6-chloro-2-(2,6-difluoro-3,5-dimethoxyphenyl)-3-oxo-1,2,3,4-tetrahydro-2,7-naphthyridine-4-carboxylate

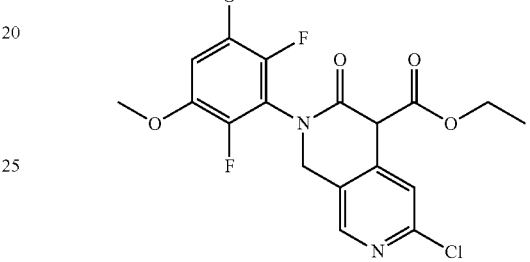

To a stirred solution of ethyl 3-[[(4,6-dichloropyridin-3-yl)methyl](2,6-difluoro-3,5-dimethoxyphenyl)amino]-3-oxopropanoate (1.50 g, 3.24 mmol) in DMF (15. mL) was added NaH (60% w/w in mineral oil, 337 mg, 8.42 mmol) at room temperature. The resulting mixture was then warmed up to 110° C. After 5 hours, the reaction mixture was cooled to room temperature then saturated aqueous $NH_4Cl$ (50 mL) was added forming precipitate. After filtration, the solid was dried in vacuo to give crude cyclized product (0.95 g, 2.23 mmol) which was used in the next step without further purification. LC-MS calculated for $C_{19}H_{18}ClF_2N_2O_5$ [M+H]+ m/z: 427.1. found 427.0.

Step 5: 6-chloro-2-(2,6-difluoro-3,5-dimethoxyphenyl)-1,2-dihydro-2,7-naphthyridin-3(4H)-one

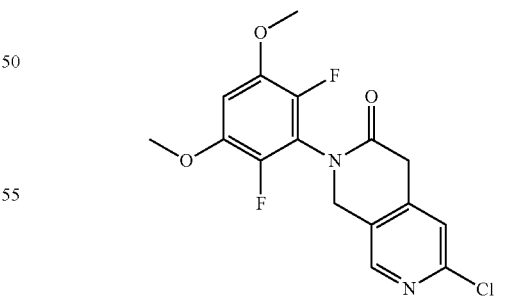

To a stirred solution of 6-chloro-2-(2,6-difluoro-3,5-dimethoxyphenyl)-3-oxo-1,2,3,4-tetrahydro-2,7-naphthyridine-4-carboxylate (0.95 g, 2.23 mmol) in 1,4-dioxane (5 mL) was added hydrogen chloride (4.0 M in dioxane, 2 mL, 8 mmol) at room temperature. The resulting mixture was warmed up to 100° C. After stirring at 100° C. for 4 hours, the reaction mixture was cooled to ambient temperature, quenched with saturated aqueous NaHCO$_3$, and extracted with DCM (3×100 mL). The organic layers were combined, dried over Na$_2$SO$_4$, and concentrated. The residue was purified on silica gel (eluting with 0 to 30% EtOAc in DCM) to afford the desired product (0.75 g, 2.12 mmol). LC-MS calculated for C$_{16}$H$_{14}$ClF$_2$N$_2$O$_3$ [M+H]$^+$ m/z: 355.1. found 355.1.

Step 6: 6'-chloro-2'-(2,6-difluoro-3,5-dimethoxyphenyl)-1',2'-dihydro-3'H-spiro[cyclopropane-1,4'-[2,7]naphthyridin]-3'-one

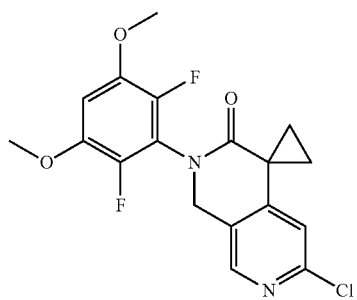 [SMILES: COc1cc(OC)c(F)c(N2Cc3cnc(Cl)cc3C3(CC3)C2=O)c1F]

To a stirred solution of 6-chloro-2-(2,6-difluoro-3,5-dimethoxyphenyl)-1,4-dihydro-2,7-naphthyridin-3(2H)-one (1.50 g, 4.23 mmol) in DMF (10 mL) was added sequentially cesium carbonate (3.03 g, 9.30 mmol) and 1-bromo-2-chloro-ethane (701 µL, 8.46 mmol) at room temperature. After stirring at room temperature for 5 hours, the reaction mixture was quenched with saturated aqueous NH$_4$Cl, and extracted with DCM (3×75 mL). The organic layers were combined, dried over Na$_2$SO$_4$, and concentrated. The residue was purified on silica gel (eluting with 0 to 50% EtOAc in hexanes) to afford the desired product (1.20 g, 3.15 mmol). LC-MS calculated for C$_{18}$H$_{16}$ClF$_2$N$_2$O$_3$ [M+H]$^+$ m/z: 381.1. found 381.1.

Step 7: 2'-(2,6-difluoro-3,5-dimethoxyphenyl)-6'-[(2-morpholin-4-ylethyl)amino]-1',2'-dihydro-3'H-spiro[cyclopropane-1,4'-[2,7]naphthyridin]-3'-one To a stirred solution of 6'-chloro-2'-(2,6-difluoro-3,5-dimethoxyphenyl)-1',2'-dihydro-3'H-spiro[cyclopropane-1,4'-[2,7]naphthyridin]-3'-one (250 mg, 0.657 mmol) and 2-morpholinoethanamine (214 mg, 1.64 mmol) in 1,4-dioxane (6.0 mL) were added sequentially dicyclohexyl(2',4',6'-triisopropyl-3,6-dimethoxybiphenyl-2-yl)phosphine (BrettPhos, Aldrich, cat#718742: 70.5 mg, 0.131 mmol), sodium tert-butoxide (126 mg, 1.31 mmol) and palladium acetate (29.5 mg, 0.131 mmol) at room temperature. The resulting mixture was purged with N$_2$ then heated to 110° C. After stirring at 110° C. for 45 minutes, the reaction mixture was cooled to ambient temperature and was purified on RP-HPLC (XBridge C18 column, eluting with a gradient of acetonitrile/water containing 0.05% TFA, at flow rate of 60 mL/min) to give the desired product (150 mg) as its TFA salt. LC-MS calculated for C$_{24}$H$_{29}$F$_2$N$_4$O$_4$ [M+H]$^+$ m/z: 475.2. found 475.2. $^1$H NMR (500 MHz, DMSO-d$_6$): δ 7.96 (s, 1 H), 7.06 (t, J=10.0 Hz, 1 H), 6.22 (s, 1 H), 4.77 (s, 2 H), 3.88 (s, 6 H), 3.82 (br, 4 H), 3.65 (br, 2 H), 3.27-3.33 (m, 6 H), 1.71 (dd, J=7.0 Hz, 4.0 Hz, 2 H), 1.43 (dd, J=7.0 Hz, 4.0 Hz, 2 H) ppm.

Example 24

6'-amino-2'-(2,6-difluoro-3,5-dimethoxyphenyl)-1'H-spiro[cyclopropane-1,4'-[2,7]naphthyridin]-3'(2'H)-one

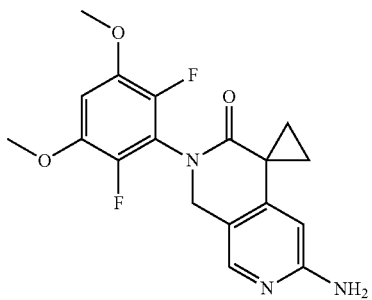 [SMILES: COc1cc(OC)c(F)c(N2Cc3cnc(N)cc3C3(CC3)C2=O)c1F]

To a stirred solution of 6'-chloro-2'-(2,6-difluoro-3,5-dimethoxyphenyl)-1',2'-dihydro-3'H-spiro[cyclopropane-1,4'-[2,7]naphthyridin]-3'-one (Example 23, Step 6: 248 mg, 0.651 mmol) and benzophenone imine (164 µL, 0.977 mmol) in toluene (5 mL) were added sequentially (R)-(+)-2,2'-bis(diphenylphosphino)-1,1'-binaphthyl (40.6 mg, 0.0651 mmol), sodium tert-butoxide (125 mg, 1.30 mmol) and tris(dibenzylideneacetone)dipalladium(O) (23.9 mg, 0.0260 mmol) at room temperature. The resulting mixture was purged with N$_2$ and heated to 90° C. After stirring for 2 hours at 90° C., the reaction mixture was cooled to ambient temperature and the volatiles were removed in vacuo. The residue was dissolved in tetrahydrofuran (5 mL) then a solution of hydrogen chloride in water (1.0 M, 650 µL, 0.65 mmol) was added. After stirring at room temperature for 1 hour, the reaction mixture was concentrated and the residue was purified on RP-HPLC (XBridge C18 column, eluting with a gradient of acetonitrile/water containing 0.05% TFA, at flow rate of 60 mL/min) to give the desired product (202 mg) as its TFA salt. LC-MS calculated for C$_{18}$H$_{18}$F$_2$N$_3$O$_3$ [M+H]$^+$ m/z: 362.1. found 362.1. $^1$H NMR (500 MHz, DMSO-d$_6$): δ 7.90 (s, 1 H), 7.77 (br, 2 H), 7.07 (t, J=10.0 Hz, 1 H), 6.49 (s, 1 H), 4.79 (s, 2 H), 3.89 (s, 6 H), 1.82 (dd, J=10.0 Hz, 5.0 Hz, 2 H), 1.51 (dd, J=10.0 Hz, 5.0 Hz, 2 H) ppm.

Example 25

2'-(2,6-difluoro-3,5-dimethoxyphenyl)-6'-(methylamino)-1',2'-dihydro-3'H-spiro[cyclopropane-1,4'-[2,7]naphthyridin]-3'-one

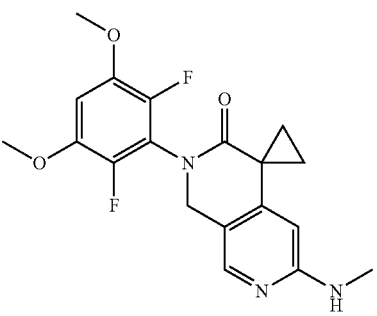

To a stirred solution of 6'-chloro-2'-(2,6-difluoro-3,5-dimethoxyphenyl)-1',2'-dihydro-3'H-spiro[cyclopropane-1,4'-[2,7]naphthyridin]-3'-one (Example 23, Step 6: 90.0 mg, 0.236 mmol) and tert-butyl methylcarbamate (89.5 mg, 0.682 mmol) in 1,4-dioxane (3 mL) were added sequentially dicyclohexyl(2',4',6'-triisopropyl-3,6-dimethoxybiphenyl-2-yl)phosphine (BrettPhos, Aldrich, cat#718742: 24.4 mg, 0.0455 mmol), sodium tert-butoxide (52.4 mg, 0.546 mmol), and palladium acetate (10.2 mg, 0.0455 mmol) at room temperature. The resulting mixture was purged with $N_2$ and heated to 90° C. After stirring for 45 minutes at 90° C., the reaction mixture was cooled to ambient temperature and the volatiles were removed in vacuo. The residue was dissolved in DCM (1 mL) then TFA (1 mL) was added. After stirring at room temperature for 1 hour, the reaction mixture was concentrated and the crude was purified on RP-HPLC (XBridge C18 column, eluting with a gradient of acetonitrile/water containing 0.05% TFA, at flow rate of 60 mL/min) to give the desired product (32 mg) as its TFA salt. LC-MS calculated for $C_{19}H_{20}F_2N_3O_3$ $[M+H]^+$ m/z: 376.1. found 376.2. $^1H$ NMR (500 MHz, DMSO-$d_6$): δ 7.90 (s, 1 H), 7.07 (t, J=10.0 Hz, 1 H), 6.46 (s, 1 H), 4.80 (s, 2 H), 3.89 (s, 6 H),), 2.90 (s, 3 H) 1.79 (dd, J=10.0 Hz, 5.0 Hz, 2 H), 1.56 (dd, J=10.0 Hz, 5.0 Hz, 2 H) ppm.

Example 26

2'-(2,6-difluoro-3,5-dimethoxyphenyl)-6'-(tetrahydro-2H-pyran-4-ylamino)-1',2'-dihydro-3'H-spiro[cyclopropane-1,4'-[2,7]naphthyridin]-3'-one

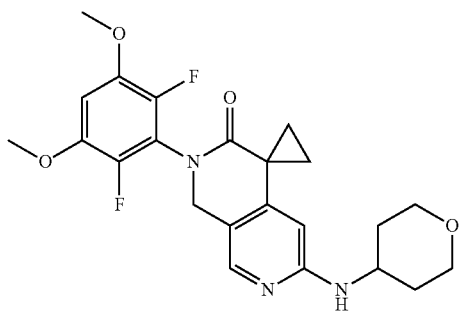 [SMILES: COc1cc(OC)c(F)c(N2Cc3cnc(NC4CCOCC4)cc3C3(CC3)C2=O)c1F]

This compound was prepared using procedures analogous to those for Example 23, Step 7 with tetrahydro-2H-pyran-4-amine replacing 2-morpholinoethanamine. LCMS calculated for $C_{23}H_{26}F_2N_3O_4$ $(M+H)^+$: m/z=446.2. Found: 446.2.

Example 27

(S)-2'-(2,6-difluoro-3,5-dimethoxyphenyl)-6'-(2-hydroxypropylamino)-1'H-spiro[cyclopropane-1,4'-[2,7]naphthyridin]-3'(2'H)-one

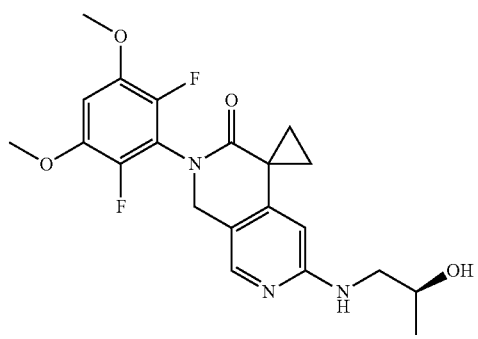 [SMILES: COc1cc(OC)c(F)c(N2Cc3cnc(NC[C@H](C)O)cc3C3(CC3)C2=O)c1F]

This compound was prepared using procedures analogous to those for Example 23, Step 7, with (S)-1-aminopropan-2-ol replacing 2-morpholinoethanamine. LCMS calculated for $C_{21}H_{24}F_2N_3O_4$ $(M+H)^+$: m/z=420.2. Found: 420.2.

Example 28

2'-(2,6-difluoro-3,5-dimethoxyphenyl)-6'-(pyridin-2-ylmethylamino)-1'H-spiro[cyclopropane-1,4'-[2,7]naphthyridin]-3'(2'H)-one

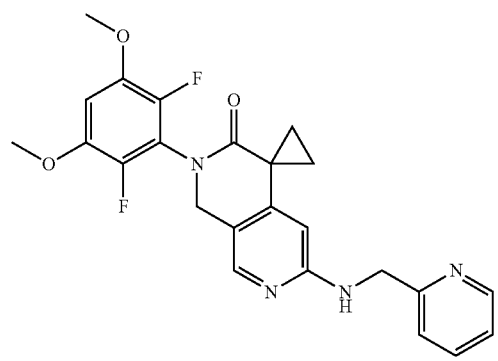 [SMILES: COc1cc(OC)c(F)c(N2Cc3cnc(NCc4ccccn4)cc3C3(CC3)C2=O)c1F]

This compound was prepared using procedures analogous to those for Example 23, Step 7, with pyridin-2-ylmethanamine replacing 2-morpholinoethanamine. LCMS calculated for $C_{24}H_{23}F_2N_4O_3$ $(M+H)^+$: m/z=453.2. Found: 453.2.

Example 29

(S)-2'-(2,6-difluoro-3,5-dimethoxyphenyl)-6'-(tetrahydrofuran-3-ylamino)-1'H-spiro[cyclopropane-1,4'-[2,7]naphthyridin]-3'(2'H)-one

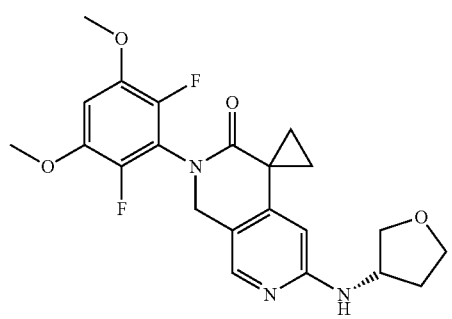

This compound was prepared using procedures analogous to those for Example 23, Step 7, with (S)-tetrahydrofuran-3-amine replacing 2-morpholinoethanamine. LCMS calculated for $C_{22}H_{24}F_2N_3O_4$ $(M+H)^+$: m/z=432.2. Found: 432.2.

Example 30

2'-(2,6-difluoro-3,5-dimethoxyphenyl)-6'-(2-(4-methylpiperazin-1-yl)ethylamino)-1'H-spiro[cyclopropane-1,4'-[2,7]naphthyridin]-3'(2'H)-one

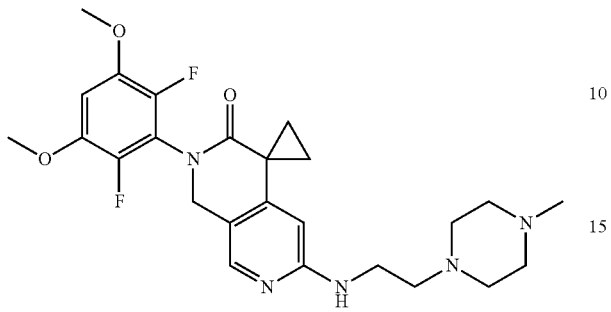

This compound was prepared using procedures analogous to those for Example 23, Step 7, with 2-(4-methylpiperazin-1-yl)ethanamine replacing 2-morpholinoethanamine. LCMS calculated for $C_{25}H_{32}F_2N_5O_4$ (M+H)$^+$: m/z=488.2. Found: 488.2.

Example 31 methyl 2'-(2,6-difluoro-3,5-dimethoxyphenyl)-3'-oxo-2',3'-dihydro-1'H-spiro[cyclopropane-1,4'-[2,7]naphthyridine]-6'-ylcarbamate

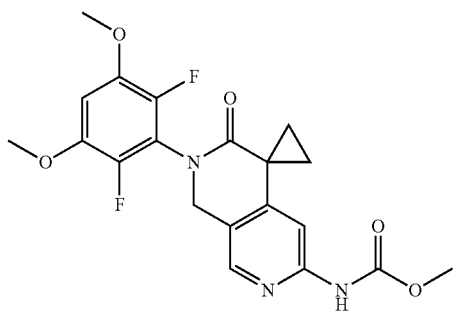

This compound was prepared using procedures analogous to those for Example 23, Step 7, with methyl carbamate replacing 2-morpholinoethanamine. LCMS calculated for $C_{20}H_{20}F_2N_3O_5$ (M+H)$^+$: m/z=420.1. Found: 420.1.

Example 32

2'-(2,6-difluoro-3,5-dimethoxyphenyl)-6'-(pyridin-3-ylamino)-1'H-spiro[cyclopropane-1,4'-[2,7]naphthyridin]-3'(2'H)-one

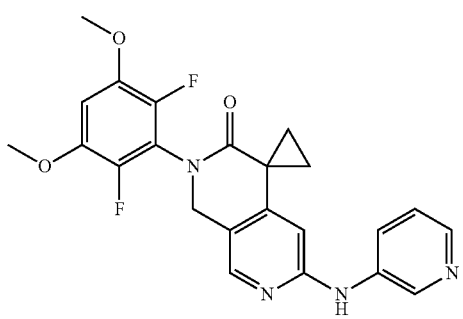 [SMILES: COc1cc(OC)c(F)c(N2Cc3cnc(Nc4cccnc4)cc3C3(CC3)C2=O)c1F]

This compound was prepared using procedures analogous to those for Example 23, Step 7, with pyridin-3-amine replacing 2-morpholinoethanamine. LCMS calculated for $C_{23}H_{21}F_2N_4O_3$ (M+H)$^+$: m/z=439.2. Found: 439.2.

Example 33

2'-(2,6-difluoro-3,5-dimethoxyphenyl)-6'-(3-fluorophenylamino)-1'H-spiro[cyclopropane-1,4'-[2,7]naphthyridin]-3'(2'H)-one

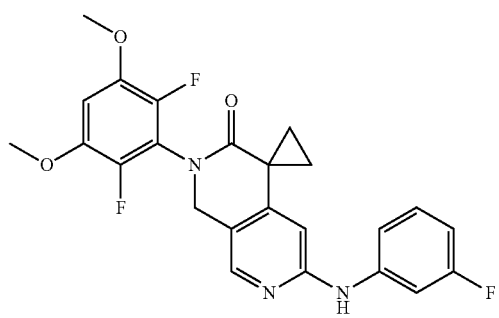 [SMILES: COc1cc(OC)c(F)c(N2Cc3cnc(Nc4cccc(F)c4)cc3C3(CC3)C2=O)c1F]

This compound was prepared using procedures analogous to those for Example 23, Step 7, with 3-fluoroaniline replacing 2-morpholinoethanamine. LCMS calculated for $C_{24}H_{21}F_3N_3O_3$ (M+H)$^+$: m/z=456.2. Found: 456.2.

Example 34

6'-(cyclopentylamino)-2'-(2,6-difluoro-3,5-dimethoxyphenyl)-1'H-spiro[cyclopropane-1,4'-[2,7]naphthyridin]-3'(2'H)-one

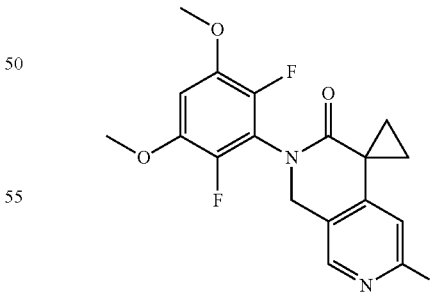

This compound was prepared using procedures analogous to those for Example 23, Step 7, with cyclopentanamine replacing 2-morpholinoethanamine. LCMS calculated for $C_{23}H_{26}F_2N_3O_3$ (M+H)$^+$: m/z=430.2. Found: 430.2.

Example 35

(S)-2'-(2,6-difluoro-3,5-dimethoxyphenyl)-6'-((tetrahydrofuran-2-yl)methylamino)-1'H-spiro[cyclopropane-1,4'-[2,7]naphthyridin]-3'(2'H)-one

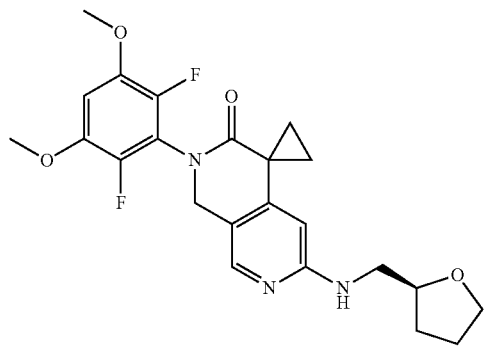 [SMILES: COc1cc(OC)c(F)c(N2Cc3cnc(NC[C@@H]4CCCO4)cc3C3(CC3)C2=O)c1F]

This compound was prepared using procedures analogous to those for Example 23, Step 7, with (S)-(tetrahydrofuran-2-yl)methanamine replacing 2-morpholinoethanamine. LCMS calculated for $C_{23}H_{26}F_2N_3O_4$ (M+H)$^+$: m/z=446.2. Found: 446.2.

Example 36

2'-(2,6-difluoro-3,5-dimethoxyphenyl)-6'-(1-methyl-1H-pyrazol-4-ylamino)-1'H-spiro[cyclopropane-1,4'-[2,7]naphthyridin]-3'(2'H)-one

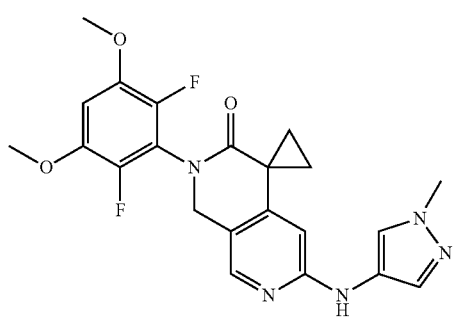 [SMILES: COc1cc(OC)c(F)c(N2Cc3cnc(Nc4cnn(C)c4)cc3C3(CC3)C2=O)c1F]

This compound was prepared using procedures analogous to those for Example 23, Step 7, with 1-methyl-1H-pyrazol-4-amine replacing 2-morpholinoethanamine. LCMS calculated for $C_{22}H_{22}F_2N_5O_3$ (M+H)$^+$: m/z=442.2. Found: 442.2.

Example 37

2'-(2,6-difluoro-3,5-dimethoxyphenyl)-6'-((1-methyl-1H-pyrazol-4-yl)methylamino)-1'H-spiro[cyclopropane-1,4'-[2,7]naphthyridin]-3'(2'H)-one

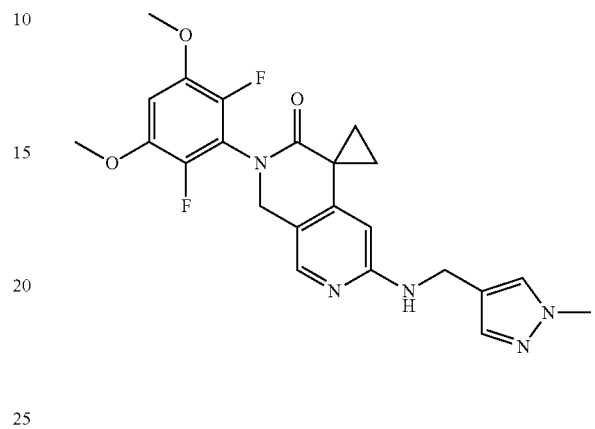

This compound was prepared using procedures analogous to those for Example 23, Step 7, with (1-methyl-1H-pyrazol-4-yl)methanamine replacing 2-morpholinoethanamine. LCMS calculated for $C_{23}H_{24}F_2N_5O_3$ (M+H)$^+$: m/z=456.2. Found: 456.2.

Example 38

(R)-2'-(2,6-difluoro-3,5-dimethoxyphenyl)-6'-(1-phenylethylamino)-1'H-spiro[cyclopropane-1,4'-[2,7]naphthyridin]-3'(2'H)-one

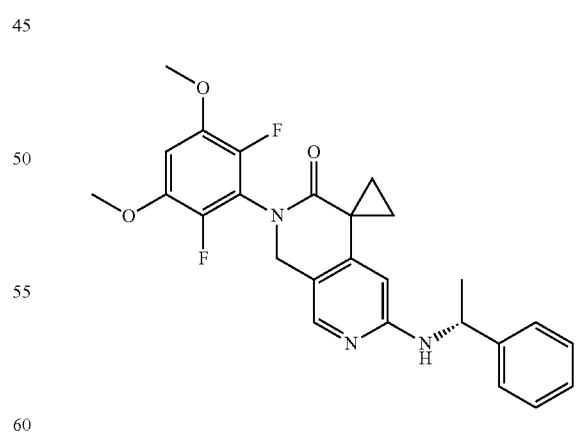

This compound was prepared using procedures analogous to those for Example 23, Step 7, with (R)-1-phenylethanamine replacing 2-morpholinoethanamine. LCMS calculated for $C_{26}H_{26}F_2N_3O_3$ (M+H)$^+$: m/z=466.2. Found: 466.2.

Example 39

6'-(cyclohexylamino)-2'-(2,6-difluoro-3,5-dimethoxyphenyl)-1'H-spiro[cyclopropane-1,4'-[2,7]naphthyridin]-3'(2'H)-one

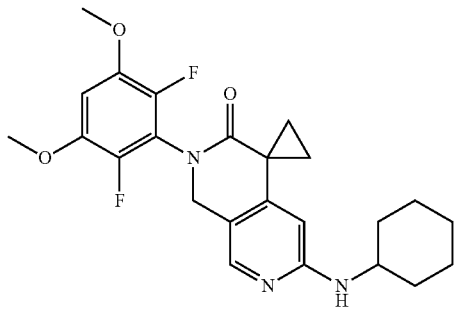 [SMILES: COc1cc(OC)c(F)c(N2Cc3cnc(NC4CCCCC4)cc3C3(CC3)C2=O)c1F]

This compound was prepared using procedures analogous to those for Example 23, Step 7, with cyclohexanamine replacing 2-morpholinoethanamine. LCMS calculated for $C_{24}H_{28}F_2N_3O_3$ (M+H)$^+$: m/z=444.2. Found: 444.2.

Example 40

2'-(2,6-difluoro-3,5-dimethoxyphenyl)-6'-(trans-4-hydroxycyclohexylamino)-1'H-spiro[cyclopropane-1,4'-[2,7]naphthyridin]-3'(2'H)-one

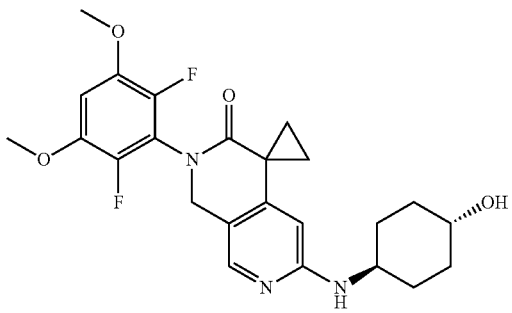 [SMILES: COc1cc(OC)c(F)c(N2Cc3cnc(N[C@H]4CC[C@H](O)CC4)cc3C3(CC3)C2=O)c1F]

This compound was prepared using procedures analogous to those for Example 23, Step 7, with trans-4-aminocyclohexanol replacing 2-morpholinoethanamine. LCMS calculated for $C_{24}H_{28}F_2N_3O_4$ (M+H)$^+$: m/z=460.2. Found: 460.2.

Example 41

6'-(cyclopropylamino)-2'-(2,6-difluoro-3,5-dimethoxyphenyl)-1'H-spiro[cyclopropane-1,4'-[2,7]naphthyridin]-3'(2'H)-one

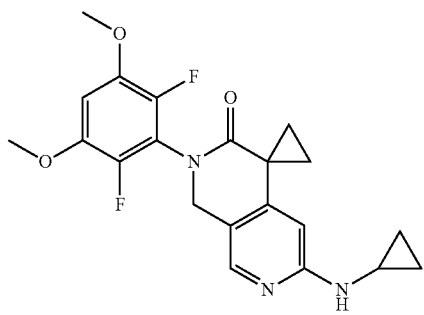 [SMILES: COc1cc(OC)c(F)c(N2Cc3cnc(NC4CC4)cc3C3(CC3)C2=O)c1F]

This compound was prepared using procedures analogous to those for Example 23, Step 7, with cyclopropanamine replacing 2-morpholinoethanamine. LCMS calculated for $C_{21}H_{22}F_2N_3O_3$ (M+H)$^+$: m/z=402.2. Found: 402.2.

Example 42

6'-(cyclobutylamino)-2'-(2,6-difluoro-3,5-dimethoxyphenyl)-1'H-spiro[cyclopropane-1,4'-[2,7]naphthyridin]-3'(2'H)-one

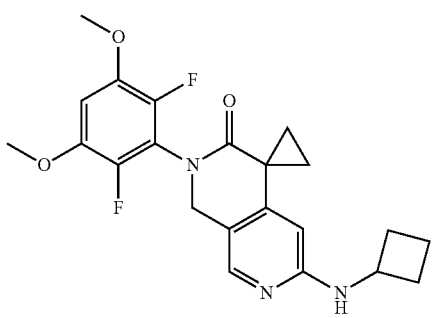 [SMILES: COc1cc(OC)c(F)c(N2Cc3cnc(NC4CCC4)cc3C3(CC3)C2=O)c1F]

This compound was prepared using procedures analogous to those for Example 23, Step 7, with cyclobutylamine replacing 2-morpholinoethanamine. LCMS calculated for $C_{22}H_{24}F_2N_3O_3$ (M+H)$^+$: m/z=416.2. Found: 416.2.

Example 43

2'-(2,6-difluoro-3,5-dimethoxyphenyl)-6'-(3,3-difluorocyclobutylamino)-1'H-spiro[cyclopropane-1,4'-[2,7]naphthyridin]-3'(2'H)-one

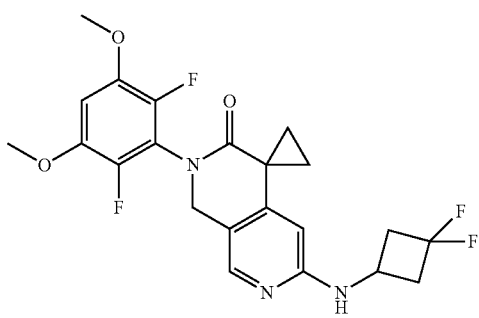 [SMILES: COc1cc(OC)c(F)c(N2Cc3cnc(NC4CC(F)(F)C4)cc3C3(CC3)C2=O)c1F]

This compound was prepared using procedures analogous to those for Example 23, Step 7, with 3,3-difluorocyclobutanamine replacing 2-morpholinoethanamine. LCMS calculated for $C_{22}H_{22}F_4N_3O_3$ (M+H)$^+$: m/z=452.2. Found: 452.2.

Example 44

2'-(2,6-difluoro-3,5-dimethoxyphenyl)-6'-(1-methyl-piperidin-4-ylamino)-1'H-spiro[cyclopropane-1,4'-[2,7]naphthyridin]-3'(2'H)-one

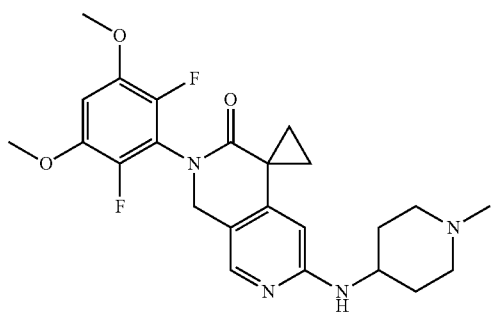

This compound was prepared using procedures analogous to those for Example 23, Step 7, with 1-methylpiperidin-4-amine replacing 2-morpholinoethanamine. LCMS calculated for $C_{24}H_{29}F_2N_4O_3$ (M+H)$^+$: m/z=459.2. Found: 459.2.

Example 45

7-amino-3-(2,6-difluoro-3,5-dimethoxyphenyl)-1-(2-fluorophenyl)-8-methyl-3,4-dihydropyrido[4,3-d]pyrimidin-2(1H)-one

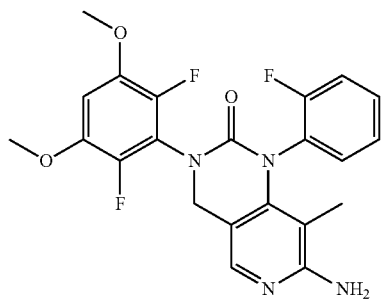 [SMILES: COc1cc(OC)c(F)c(N2Cc3cnc(N)c(C)c3N(c3ccccc3F)C2=O)c1F]

Step 1: (4,6-dichloro-5-methylpyridin-3-yl)methanol

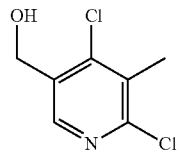

To a stirred solution of ethyl 4,6-dichloro-5-methylnicotinate (1.75 g, 7.48 mmol, Ark Pharm, cat# AK121795) in methylene chloride (30 mL) at −78° C. was added diisobutylaluminum hydride (1.0 M in toluene, 18.0 mL, 18.0 mmol) dropwise. The resulting mixture was stirred at −78° C. for 2 h then quenched with saturated aqueous NH$_4$Cl. The mixture was warmed to room temperature then extracted with DCM (3×20 mL). The combined organic layers were washed with brine, dried over Na$_2$SO$_4$, filtered and concentrated under reduced pressure. The residue was purified by flash chromatography on a silica gel column eluting with MeOH in DCM (0-5%) to afford the desired product (0.80 g, 56%). LCMS calculated for $C_7H_8Cl_2NO$ (M+H)$^+$: m/z=192.0. Found: 192.0.

Step 2: N-[(4,6-dichloro-5-methylpyridin-3-yl)methyl]-2,6-difluoro-3,5-dimethoxyaniline

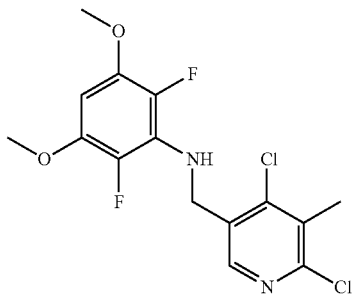 [SMILES: COc1cc(OC)c(F)c(NCc2cnc(Cl)c(C)c2Cl)c1F]

To a stirred solution of (4,6-dichloro-5-methylpyridin-3-yl)methanol (0.80 g, 4.2 mmol) in methylene chloride (20 mL) at 0° C. was added N,N-diisopropylethylamine (1.45 mL, 8.33 mmol), followed by methanesulfonyl chloride (0.42 mL, 5.4 mmol). The resulting mixture was warmed to room temperature and stirred for 2 h then quenched with saturated aqueous NaHCO$_3$. The mixture was extracted with DCM (3×50 mL). The combined organic layers were washed with brine, dried over Na$_2$SO$_4$, filtered and concentrated under reduced pressure. The residue was dissolved in N,N-diisopropylethylamine (3.5 mL) then 2,6-difluoro-3,5-dimethoxyaniline (0.79 g, 4.2 mmol) was added. The mixture was stirred at 100° C. overnight. The reaction mixture was cooled to room temperature then quenched with saturated aqueous NaHCO$_3$, and extracted with ethyl acetate (3×20 mL). The combined organic layers were washed with brine, dried over Na$_2$SO$_4$, filtered and concentrated under reduced pressure. The residue was purified by flash chromatography on a silica gel column eluting with ethyl acetate in hexanes (0-25%) to afford the desired product (1.5 g, 99%). LCMS calculated for $C_{15}H_{15}Cl_2F_2N_2O_2$ (M+H)$^+$: m/z=363.0. Found: 363.0.

Step 3: 4-chloro-5-{[(2,6-difluoro-3,5-dimethoxyphenyl)amino]methyl}-N-(4-methoxybenzyl)-3-methylpyridin-2-amine

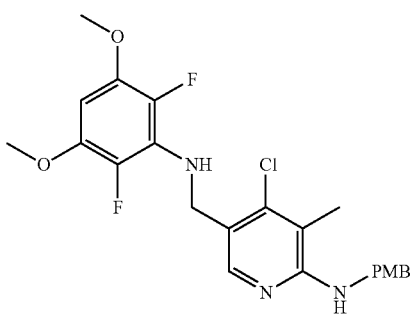

A mixture of N-[(4,6-dichloro-5-methylpyridin-3-yl)methyl]-2,6-difluoro-3,5-dimethoxyaniline (1.5 g, 4.1 mmol), benzenemethanamine, 4-methoxy-(1.1 mL, 8.3 mmol), (R)-(+)-2,2'-bis(diphenylphosphino)-1,1'-binaphthyl (0.26 g, 0.42 mmol), palladium acetate (0.093 g, 0.41 mmol) and cesium carbonate (2.7 g, 8.3 mmol) in 1,4-dioxane (10 mL) was purged with nitrogen then heated to 150° C. and stirred overnight. After cooling to room temperature, the reaction mixture was diluted with ethyl acetate, filtered and concentrated under reduced pressure. The residue was purified by flash chromatography on a silica gel column eluting with ethyl acetate in hexanes (0-25%) to afford the desired product (1.0 g, 52%). LCMS calculated for $C_{23}H_{25}ClF_2N_3O_3$ (M+H)$^+$: m/z=464.2. Found: 464.1.

Step 4: 5-{[(2,6-difluoro-3,5-dimethoxyphenyl)amino]methyl}-N4-(2-fluorophenyl)-N2-(4-methoxybenzyl)-3-methylpyridine-2,4-diamine

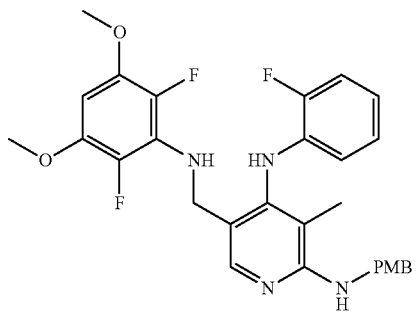

To a mixture of 4-chloro-5-{[(2,6-difluoro-3,5-dimethoxyphenyl)amino]methyl}-N-(4-methoxybenzyl)-3-methylpyridin-2-amine (32 mg, 0.070 mmol), palladium acetate (1.6 mg, 0.0070 mmol), (R)-(+)-2,2'-bis(diphenylphosphino)-1,1'-binaphthyl (4.4 mg, 0.0070 mmol), and cesium carbonate (69 mg, 0.21 mmol) in 1,4-dioxane (1.0 mL) was added 2-fluoroaniline (11 mg, 0.098 mmol). The resulting mixture was purged with nitrogen then heated to 150° C. and stirred overnight. After cooling to room temperature, the reaction mixture was diluted with ethyl acetate, filtered and concentrated under reduced pressure. The residue was used in the next step without further purification. LCMS calculated for $C_{29}H_{30}F_3N_4O_3$ (M+H)$^+$: m/z=539.2. Found: 539.2.

Step 5: 3-(2,6-difluoro-3,5-dimethoxyphenyl)-1-(2-fluorophenyl)-7-[(4-methoxybenzyl)amino]-8-methyl-3,4-dihydropyrido[4,3-d]pyrimidin-2(1H)-one

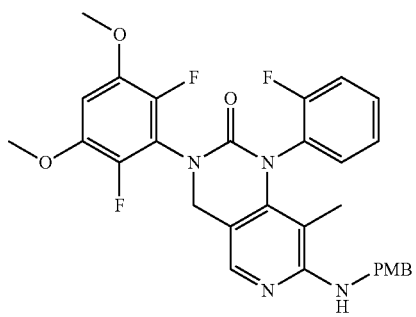

Triphosgene (21 mg, 0.070 mmol) was added to a solution of the crude product from Step 4 and N,N-diisopropylethylamine (73 μL, 0.42 mmol) in tetrahydrofuran (2.0 mL). The resulting mixture was stirred at room temperature for 30 min then 2N NaOH (2 mL) was added. The mixture was stirred at 30° C. for 1 h then cooled to room temperature and extracted with ethyl acetate (3×20 mL). The combined organic layers were washed with brine, dried over $Na_2SO_4$, filtered and concentrated under reduced pressure. The residue was used in the next step without further purification. LCMS calculated for $C_{30}H_{28}F_3N_4O_4$ (M+H)$^+$: m/z=565.2. Found: 565.2.

Step 6: 7-amino-3-(2,6-difluoro-3,5-dimethoxyphenyl)-1-(2-fluorophenyl)-8-methyl-3,4-dihydropyrido[4,3-d]pyrimidin-2(1H)-one The crude product from Step 5 was dissolved in 1 mL of TFA and the reaction mixture was stirred at 85° C. for 3 h. The mixture was cooled to room temperature and concentrated in vacuo. The residue was dissolved in acetonitrile then purified by RP-HPLC (pH=2) to afford the desired product as TFA salt. LCMS calculated for $C_{22}H_{20}F_3N_4O_3$ (M+H)$^+$: m/z=445.1. Found: 445.2.

Example 46

7-amino-3-(2,6-difluoro-3,5-dimethoxyphenyl)-8-methyl-1-(2-methyl-2H-tetrazol-5-yl)-3,4-dihydropyrido[4,3-d]pyrimidin-2(1H)-one

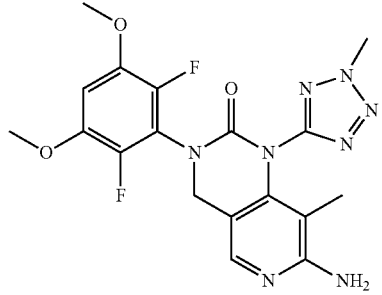 [SMILES: COc1cc(OC)c(F)c(N2Cc3cnc(N)c(C)c3N(c3nnn(C)n3)C2=O)c1F]

This compound was prepared using procedures analogous to those as described for Example 45 with 2-methyl-2H-tetrazol-5-amine (Combi-Blocks, cat#OR-5103) replacing 2-fluoroaniline in Step 4. LCMS calculated for $C_{18}H_{19}F_2N_8O_3$ (M+H)$^+$: m/z=433.2. Found: 433.2.

Example 47

7-amino-3-(2,6-difluoro-3,5-dimethoxyphenyl)-8-methyl-1-[(1-methyl-1H-pyrazol-4-yl)methyl]-3,4-dihydropyrido[4,3-d]pyrimidin-2(1H)-one

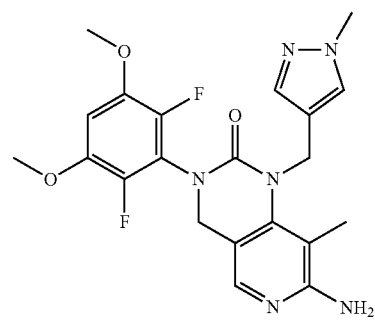

This compound was prepared using procedures analogous to those as described for Example 45 with 1-(1-methyl-1H-pyrazol-4-yl)methanamine hydrochloride (J&W PharmLab, Cat#68R0166) replacing 2-fluoroaniline in Step 4. LCMS calculated for $C_{21}H_{23}F_2N_6O_3$ (M+H)$^+$: m/z=445.2. Found: 445.1.

Example 48 methyl [3-(2,6-difluoro-3,5-dimethoxyphenyl)-1,8-dimethyl-2-oxo-1,2,3,4-tetrahydropyrido[4,3-d]pyrimidin-7-yl]carbamate

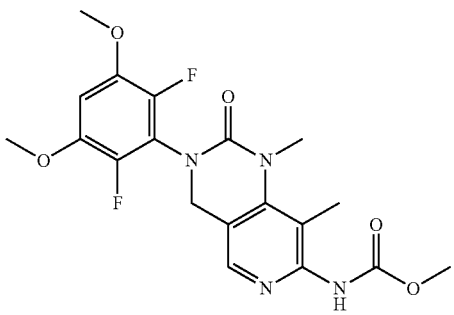

Step 1: [(4,6-dichloro-5-methylpyridin-3-yl)methyl](2,6-difluoro-3,5-dimethoxyphenyl) carbamic chloride

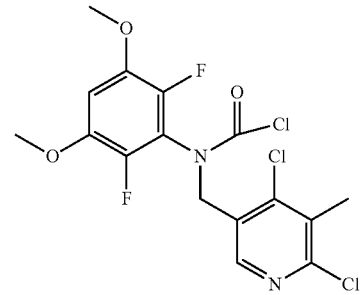 [SMILES: COc1cc(OC)c(F)c(N(Cc2cnc(Cl)c(C)c2Cl)C(=O)Cl)c1F]

To a solution of N-[(4,6-dichloro-5-methylpyridin-3-yl)methyl]-2,6-difluoro-3,5-dimethoxyaniline (Example 45, Step 2: 1.25 g, 3.44 mmol) in methylene chloride (30 mL) at 0° C. was added triphosgene (0.61 g, 2.1 mmol), followed by pyridine (840 μL, 10. mmol). The reaction mixture was stirred at 0° C. for 1 hour then diluted with methylene chloride and washed with 1N HCl solution. Then the aqueous solution was extracted with methylene chloride. The combined organic layers were washed with water, brine, dried over $Na_2SO_4$, then concentrated to give the desired product (1.45 g, 99%) which was used in the next step without further purification. LCMS calculated for $C_{16}H_{14}Cl_3F_2N_2O_3$ (M+H)$^+$: m/z=425.0. Found: 425.0.

Step 2: N-[(4,6-dichloro-5-methylpyridin-3-yl)methyl]-N-(2,6-difluoro-3,5-dimethoxyphenyl)-N'-methylurea

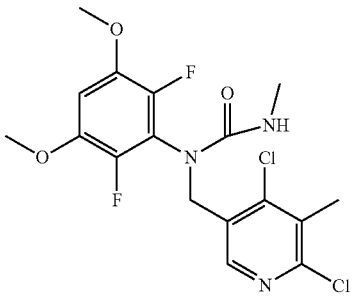 [SMILES: CNC(=O)N(Cc1cnc(Cl)c(C)c1Cl)c1c(F)c(OC)cc(OC)c1F]

To a solution of [(4,6-dichloro-5-methylpyridin-3-yl)methyl](2,6-difluoro-3,5-dimethoxyphenyl)carbamic chloride (1.45 g, 3.41 mmol) in methylene chloride (6 mL) was added methylamine (2M in THF, 3.4 mL, 6.8 mmol) and N,N-diisopropylethylamine (3.0 mL, 17 mmol). The resulting mixture was stirred at room temperature for 30 min then concentrated. The residue was purified on a silica gel column to give the desired product (1.35 g, 94%). LCMS calculated for $C_{17}H_{18}Cl_2F_2N_3O_3$ (M+H)$^+$: m/z=420.1. Found: 420.0.

Step 3: 7-chloro-3-(2,6-difluoro-3,5-dimethoxyphenyl)-1,8-dimethyl-3,4-dihydropyrido[4,3-d]pyrimidin-2(1H)-one

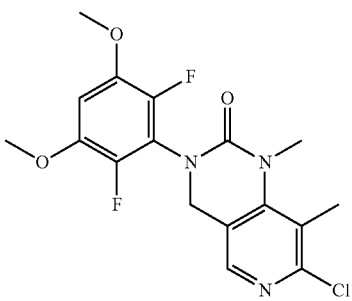 [SMILES: COc1cc(OC)c(F)c(N2Cc3cnc(Cl)c(C)c3N(C)C2=O)c1F]

A mixture of N-[(4,6-dichloro-5-methylpyridin-3-yl)methyl]-N-(2,6-difluoro-3,5-dimethoxyphenyl)-N'-methylurea (0.80 g, 1.9 mmol), cesium carbonate (1.9 g, 5.7 mmol) in N,N-dimethylformamide (7 mL) in a reaction vial was stirred at 110° C. overnight. After cooling to room temperature, the mixture was quenched with sat'd $NH_4Cl$ solution, and extracted with ethyl acetate. The combined extracts were washed with water and brine then dried over $Na_2SO_4$ and concentrated. The residue was purified on a silica gel column to give the desired product (0.58 g, 79%). LCMS calculated for $C_{17}H_{17}ClF_2N_3O_3$ (M+H)$^+$: m/z=384.1. Found: 384.1.

Step 4: 7-amino-3-(2,6-difluoro-3,5-dimethoxyphenyl)-1,8-dimethyl-3,4-dihydropyrido[4,3-d]pyrimidin-2(1H)-one

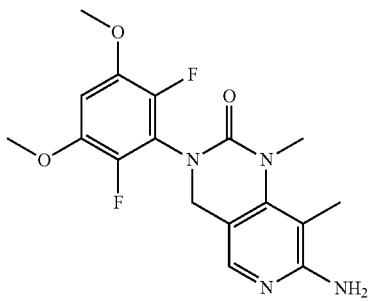 [SMILES: COc1cc(OC)c(F)c(N2Cc3cnc(N)c(C)c3N(C)C2=O)c1F]

A mixture of 7-chloro-3-(2,6-difluoro-3,5-dimethoxyphenyl)-1,8-dimethyl-3,4-dihydropyrido[4,3-d]pyrimidin-2(1H)-one (200 mg, 0.5 mmol), benzophenone imine (110 μL, 0.68 mmol), 2,2'-bis(diphenylphosphino)-1,1'-binaphthyl (32 mg, 0.052 mmol) and tris(dibenzylideneacetone)dipalladium(0) (20 mg, 0.02 mmol) in toluene (4 mL) was purged with nitrogen for 5 min. The mixture was stirred at 90° C. for 2 hours then cooled to room temperature and concentrated. The residue was purified on a silica gel column to give the intermediate (210 mg). The intermediate was dissolved in tetrahydrofuran (3 mL) then hydrogen chloride (1 M in water, 0.3 mL, 0.3 mmol) was added. The mixture was stirred at room temperature for 3 hours then concentrated and the residue was purified on a silica gel column to give the desired product (150 mg). LCMS calculated for $C_{17}H_{19}F_2N_4O_3$ (M+H)$^+$: m/z=365.1. Found: 365.1.

Step 5: methyl [3-(2,6-difluoro-3,5-dimethoxyphenyl)-1,8-dimethyl-2-oxo-1,2,3,4-tetrahydropyrido[4,3-d]pyrimidin-7-yl]carbamate To a solution of 7-amino-3-(2,6-difluoro-3,5-dimethoxyphenyl)-1,8-dimethyl-3,4-dihydropyrido[4,3-d]pyrimidin-2(1H)-one (120 mg, 0.33 mmol) in methylene chloride (5 mL) was added methyl chloroformate (38 μL, 0.49 mmol) and triethylamine (230 μL, 1.6 mmol). The resulting mixture was stirred at room temperature overnight then concentrated. The residue was purified by reverse phase HPLC (pH=2, acetonitrile/water+TFA) to give the desired product as the TFA salt. LCMS calculated for $C_{19}H_{21}F_2N_4O_5$ (M+H)$^+$: m/z=423.1. Found: 423.1. $^1$H NMR (500 MHz, DMSO-d$_6$) δ 9.80 (s, 1H), 8.03 (s, 1H), 7.02 (t, J=8.2 Hz, 1H), 4.67 (s, 2H), 3.88 (s, 6H), 3.68 (s, 3H), 3.34 (s, 3H), 2.21 (s, 3H) ppm.

Example 49

7-amino-1-(cyclopropylmethyl)-3-(2,6-difluoro-3,5-dimethoxyphenyl)-2-oxo-1,2,3,4-tetrahydropyrido[4,3-d]pyrimidine-8-carbonitrile

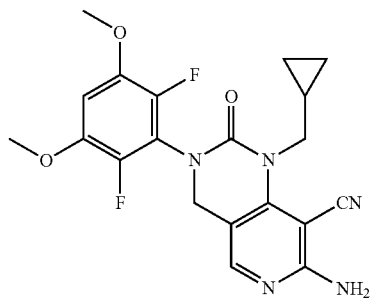 [SMILES: COc1cc(OC)c(F)c(N2Cc3cnc(N)c(C#N)c3N(CC3CC3)C2=O)c1F]

Step 1: 2,4-dichloro-5-formylnicotinonitrile

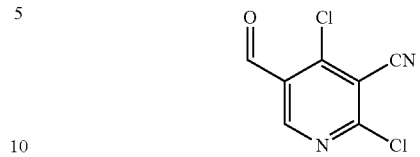

A mixture of malononitrile (2.0 g, 30. mmol) and trimethylorthoacetate (4.0 g, 33 mmol) was heated at reflux for 3 hours then it was cooled to room temperature and concentrated to give (1-methoxyethylidene)malononitrile (3.7 g) which was used in the next step without further purification. A solution of (1-methoxyethylidene)malononitrile (2.0 g, 16 mmol) in N,N-dimethylformamide (4.8 g, 66 mmol) was added dropwise to phosphoryl chloride (10 g, 66 mmol) at 95° C. The resulting mixture was stirred at 95° C. for 3 days then cooled to room temperature and diluted with methylene chloride (50 mL). The mixture was stirred at room temperature for 1 h then water (50 mL) was added and the mixture was stirred at room temperature for an additional 1 h. The mixture was extracted with methylene chloride. The combined organic layers were washed with water and brine then dried over Na$_2$SO$_4$ and concentrated. The residue was purified on a silica gel column to give the desired product (1.46 g, 44%). $^1$H NMR (400 MHz, CDCl$_3$): δ 10.44 (s, 1 H), 8.99 (s, 1 H) ppm.

Step 2: 2,4-dichloro-5-{[(2,6-difluoro-3,5-dimethoxyphenyl)amino]methyl}nicotinonitrile

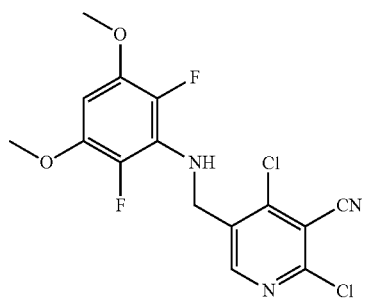 [SMILES: COc1cc(OC)c(F)c(NCc2cnc(Cl)c(C#N)c2Cl)c1F]

To a mixture of sodium triacetoxyborohydride (1.0 g, 5.0 mmol) in trifluoroacetic acid (2 mL, 20 mmol) at room temperature was added a solution of 2,6-difluoro-3,5-dimethoxyaniline (0.52 g, 2.7 mmol) in methylene chloride (20 mL). The resulting mixture was stirred for 5 min at room temperature then a solution of 2,4-dichloro-5-formylnicotinonitrile (0.50 g, 2.5 mmol) in methylene chloride (20 mL) was added. The mixture was stirred at room temperature for 1 h then neutralized with sat'd NaHCO$_3$ solution and extracted with methylene chloride. The combined organic layers were washed with water and brine then dried over Na$_2$SO$_4$ and concentrated. The residue was purified on a silica gel column to give the desired product (0.87 g, 93%). LCMS calculated for $C_{15}H_{12}Cl_2F_2N_3O_2$ (M+H)$^+$: m/z=374.0. Found: 373.9.

Step 3: [(4,6-dichloro-5-cyanopyridin-3-yl)methyl](2,6-difluoro-3,5-dimethoxyphenyl)carbamic chloride

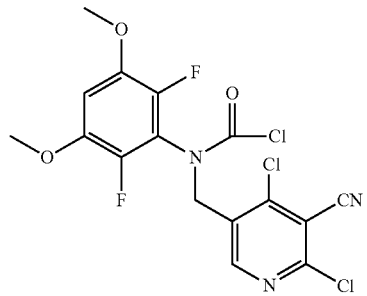 [SMILES: COc1cc(OC)c(F)c(N(Cc2cnc(Cl)c(C#N)c2Cl)C(=O)Cl)c1F]

To a solution of 2,4-dichloro-5-{[(2,6-difluoro-3,5-dimethoxyphenyl)amino]methyl}-nicotinonitrile (810 mg, 2.2 mmol) in methylene chloride (30 mL) at 0° C. was added triphosgene (0.38 g, 1.3 mmol), followed by pyridine (520 μL, 6.5 mmol). The mixture was stirred at 0° C. for 1 hour then diluted with methylene chloride and washed with 1 N HCl solution. The mixture was then extracted with methylene chloride. The combined organic layers were washed with water and brine then dried over $Na_2SO_4$ and concentrated to yield the desired product (0.84 g, 89%) which was used in the next step without further purification. LCMS calculated for $C_{16}H_{11}Cl_3F_2N_3O_3$ (M+H)$^+$: m/z=436.0. Found: 435.8.

Step 4: N'-(cyclopropylmethyl)-N-[(4,6-dichloro-5-cyanopyridin-3-yl)methyl]-N-(2,6-difluoro-3,5-dimethoxyphenyl)urea

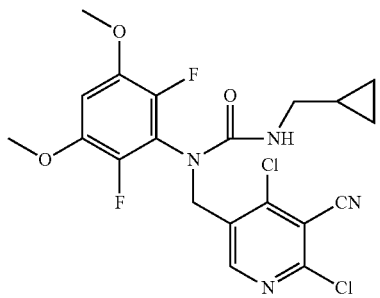 [SMILES: COc1cc(OC)c(F)c(N(Cc2cnc(Cl)c(C#N)c2Cl)C(=O)NCC2CC2)c1F]

To a solution of [(4,6-dichloro-5-cyanopyridin-3-yl)methyl](2,6-difluoro-3,5-dimethoxyphenyl)carbamic chloride (35 mg, 0.080 mmol) in methylene chloride (1 mL) was added cyclopropylmethylamine (8.9 μL, 0.10 mmol) and N,N-diisopropylethylamine (70 μL, 0.40 mmol). The resulting solution was stirred at room temperature for 30 min then diluted with DCM and washed with 1 N HCl aqueous solution. The organic layer was washed with brine then dried over $Na_2SO_4$ and concentrated. The residue was used in the next step without further purification. LCMS calculated for $C_{20}H_{19}Cl_2F_2N_4O_3$ (M+H)$^+$: m/z=471.1. Found: 471.1.

Step 5: 7-chloro-1-(cyclopropylmethyl)-3-(2,6-difluoro-3,5-dimethoxyphenyl)-2-oxo-1,2,3,4-tetrahydropyrido[4,3-d]pyrimidine-8-carbonitrile

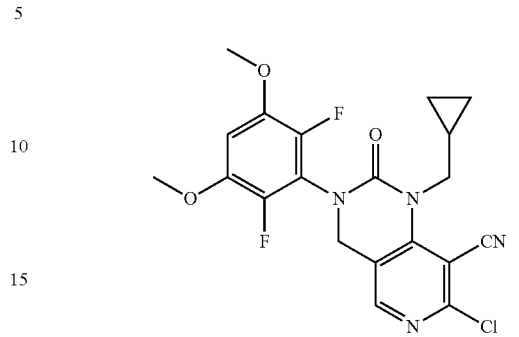

A mixture of the crude product from Step 4 and potassium carbonate (22 mg, 0.16 mmol) in acetonitrile (3 mL) was heated to reflux and stirred overnight. The reaction mixture was cooled to room temperature then diluted with DCM and washed with water and brine. The organic layer was dried over $Na_2SO_4$ then concentrated. The residue was used in the next step without further purification. LCMS calculated for $C_{20}H_{18}ClF_2N_4O_3$ (M+H)$^+$: m/z=435.1. Found: 434.7.

Step 6: 1-(cyclopropylmethyl)-3-(2,6-difluoro-3,5-dimethoxyphenyl)-7-[(diphenylmethylene)-amino]-2-oxo-1,2,3,4-tetrahydropyrido[4,3-d]pyrimidine-8-carbonitrile

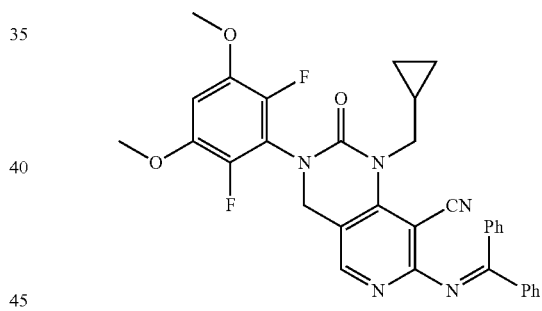

A mixture of the crude product from Step 5, bis(dibenzylideneacetone)palladium(O) (5 mg, 0.008 mmol), (R)-(+)-2,2'-bis(diphenylphosphino)-1,1'-binaphthyl (5 mg, 0.008 mmol), sodium tert-butoxide (15 mg, 0.16 mmol) and benzophenone imine (20. μL, 0.12 mmol) in toluene (5 mL) was evacuated then filled with nitrogen. The resulting mixture was heated to 90° C. and stirred for 3 h. The reaction mixture was cooled to room temperature then diluted with water and extracted with DCM. The combined extracts were dried over $Na_2SO_4$ then concentrated. The residue was purified on a silica gel column eluting with 0 to 100% EtOAc/Hexanes to give the desired product (13 mg) as a yellow solid. LCMS calculated for $C_{33}H_{28}F_2N_5O_3$ (M+H)$^+$: m/z=580.2. Found: 580.0.

Step 7: 7-amino-1-(cyclopropylmethyl)-3-(2,6-difluoro-3,5-dimethoxyphenyl)-2-oxo-1,2,3,4-tetrahydropyrido[4,3-d]pyrimidine-8-carbonitrile The product from Step 6 was dissolved in tetrahydrofuran (3 mL) then 1.0 M hydrogen chloride in water (0.16 mL, 0.16 mmol) was added. The resulting mixture was stirred at room temperature for 2 h then diluted with acetonitrile and purified by prep HPLC (pH=2, acetonitrile/water+TFA) to give the desired product as the TFA salt. LCMS calculated for $C_{20}H_{20}F_2N_5O_3$ (M+H)$^+$: m/z=416.2. Found: 416.2.

Example 50

7-amino-1-cyclopentyl-3-(2,6-difluoro-3,5-dimethoxyphenyl)-2-oxo-1,2,3,4-tetrahydropyrido[4,3-d]pyrimidine-8-carbonitrile

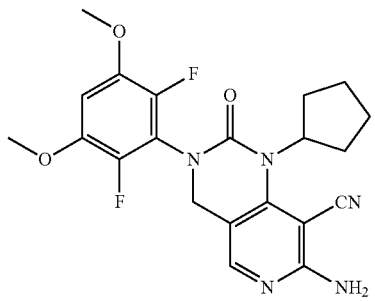 [SMILES: COc1cc(OC)c(F)c(N2Cc3cnc(N)c(C#N)c3N(C3CCCC3)C2=O)c1F]

This compound was prepared using procedures analogous to those as described for Example 49 with cyclopentanamine replacing cyclopropylmethylamine in Step 4. LCMS calculated for $C_{21}H_{22}F_2N_5O_3$ (M+H)$^+$: m/z=430.2. Found: 430.2.

Example 51

7-amino-3-(2,6-difluoro-3,5-dimethoxyphenyl)-1-[(1-methyl-1H-pyrazol-4-yl)methyl]-2-oxo-1,2,3,4-tetrahydropyrido[4,3-d]pyrimidine-8-carbonitrile

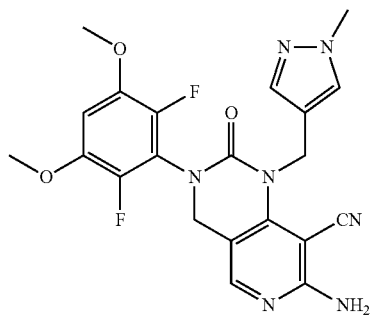

This compound was prepared using procedures analogous to those as described for Example 49 with 1-(1-methyl-1H-pyrazol-4-yl)methanamine (AstaTech, cat#BL009313) replacing cyclopropylmethylamine in Step 4. LCMS calculated for $C_{21}H_{20}F_2N_7O_3$ (M+H)$^+$: m/z=456.2. Found: 456.0.

Example 52

7-amino-1-(3,5-difluorobenzyl)-3-(2,6-difluoro-3,5-dimethoxyphenyl)-2-oxo-1,2,3,4-tetrahydropyrido[4,3-d]pyrimidine-8-carbonitrile

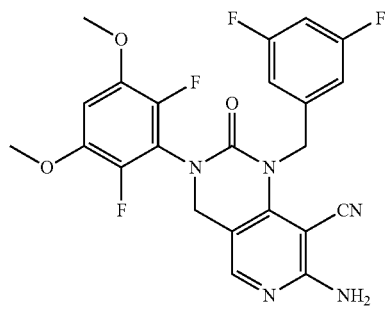 [SMILES: COc1cc(OC)c(F)c(N2Cc3cnc(N)c(C#N)c3N(Cc3cc(F)cc(F)c3)C2=O)c1F]

This compound was prepared using procedures analogous to those as described for Example 49 with 1-(3,5-difluorophenyl)methanamine replacing cyclopropylmethylamine in Step 4. LCMS calculated for $C_{23}H_{18}F_4N_5O_3$ (M+H)$^+$: m/z=488.1. Found: 488.1.

Example 53

7-amino-3-(2,6-difluoro-3,5-dimethoxyphenyl)-1-(2-fluorophenyl)-2-oxo-1,2,3,4-tetrahydropyrido[4,3-d]pyrimidine-8-carbonitrile

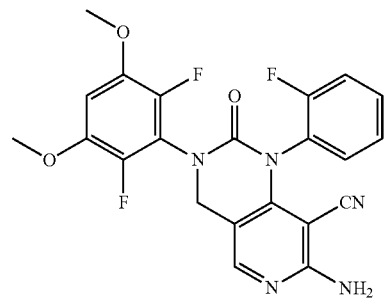 [SMILES: COc1cc(OC)c(F)c(N2Cc3cnc(N)c(C#N)c3N(c3ccccc3F)C2=O)c1F]

Step 1: 7-chloro-3-(2,6-difluoro-3,5-dimethoxyphenyl)-1-(2-fluorophenyl)-2-oxo-1,2,3,4-tetrahydropyrido[4,3-d]pyrimidine-8-carbonitrile

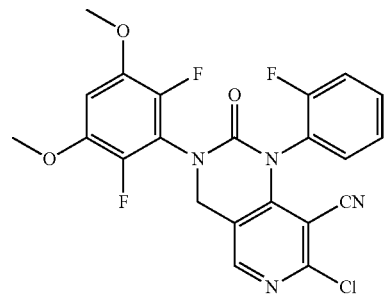 [SMILES: COc1cc(OC)c(F)c(N2Cc3cnc(Cl)c(C#N)c3N(c3ccccc3F)C2=O)c1F]

A mixture of [(4,6-dichloro-5-cyanopyridin-3-yl)methyl] (2,6-difluoro-3,5-dimethoxyphenyl)carbamic chloride (35 mg, 0.080 mmol), 2-fluoro-benzenamine (9.8 mg, 0.088 mmol) and N,N-diisopropylethylamine (42 μL, 0.24 mmol) in 1,2-dichloroethane (0.4 mL) was stirred at 90° C. overnight. The reaction mixture was cooled to room temperature then potassium carbonate (25 mg, 0.18 mmol) and acetonitrile (1 mL) were added. The mixture was stirred at 90° C. for 4 hours. After cooling to room temperature, the mixture was concentrated and the residue was purified on a silica gel column to give the desired product (30 mg, 80%). LCMS calculated for $C_{22}H_{15}ClF_3N_4O_3$ $(M+H)^+$: m/z=475.1. Found: 474.9.

Step 2: 7-amino-3-(2,6-difluoro-3,5-dimethoxyphenyl)-1-(2-fluorophenyl)-2-oxo-1,2,3,4-tetrahydropyrido[4,3-d]pyrimidine-8-carbonitrile This compound was prepared from 7-chloro-3-(2,6-difluoro-3,5-dimethoxyphenyl)-1-(2-fluorophenyl)-2-oxo-1,2,3,4-tetrahydropyrido[4,3-d]pyrimidine-8-carbonitrile using similar conditions as described for Example 49, Step 6-7. LCMS calculated for $C_{22}H_{17}F_3N_5O_3$ $(M+H)^\circ$: m/z=456.1. Found: 455.9.

Example 54

7-amino-8-chloro-3-(2,6-difluoro-3,5-dimethoxyphenyl)-1-methyl-3,4-dihydropyrido[4,3-d]pyrimidin-2(1H)-one

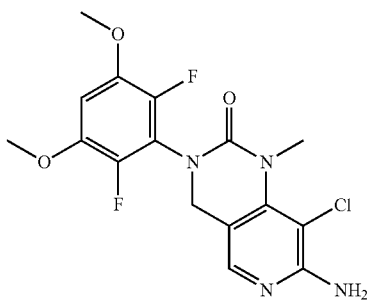

To a solution of 7-amino-3-(2,6-difluoro-3,5-dimethoxyphenyl)-1-methyl-3,4-dihydropyrido[4,3-d]pyrimidin-2(1H)-one (Example 1, Step 6: 15 mg, 0.043 mmol) in DMF (1.0 mL) was added N-chlorosuccinimide (17 mg, 0.13 mmol). The resulting mixture was stirred at room temperature for 1 h then it was purified by prep-HPLC (pH 2, acetonitrile/water+TFA) to afford the desired product as the TFA salt. LC-MS calculated for $C_{16}H_{16}ClF_2N_4O_3$ $[M+H]^+$ m/z: 385.1. found 385.1. $^1$H NMR (500 MHz, DMSO) δ 7.75 (s, 1H), 7.15 (s, 2H), 7.02 (t, J=7.5 Hz, 1H), 4.57 (s, 2H), 3.88 (s, 6H), 3.45 (s, 3H) ppm.

Example A

FGFR Enzymatic Assay

The inhibitor potency of the exemplified compounds was measured in an enzyme assay that measures peptide phosphorylation using FRET measurements to detect product formation. Inhibitors were serially diluted in DMSO and a volume of 0.5 μL was transferred to the wells of a 384-well plate. For FGFR3, a 10 μL volume of FGFR3 enzyme (Millipore) diluted in assay buffer (50 mM HEPES, 10 mM $MgCl_2$, 1 mM EGTA, 0.01% Tween-20, 5 mM DTT, pH 7.5) was added to the plate and pre-incubated for 5-10 minutes. Appropriate controls (enzyme blank and enzyme with no inhibitor) were included on the plate. The assay was initiated by the addition of a 10 μL solution containing biotinylated EQEDEPEGDYFEWLE peptide substrate (SEQ ID NO: 1) and ATP (final concentrations of 500 nM and 140 μM respectively) in assay buffer to the wells. The plate was incubated at 25° C. for 1 hr. The reactions were ended with the addition of 10 μL/well of quench solution (50 mM Tris, 150 mM NaCl, 0.5 mg/mL BSA, pH 7.8; 30 mM EDTA with Perkin Elmer Lance Reagents at 3.75 nM Eu-antibody PY20 and 180 nM APC-Streptavidin). The plate was allowed to equilibrate for ~1 hr before scanning the wells on a PheraStar plate reader (BMG Labtech).

FGFR1 and FGFR2 were measured under equivalent conditions with the following changes in enzyme and ATP concentrations: FGFR1, 0.02 nM and 210 μM, respectively and FGFR2, 0.01 nM and 100 μM, respectively. The enzymes were purchased from Millipore or Invitrogen.

GraphPad prism3 was used to analyze the data. The $IC_{50}$ values were derived by fitting the data to the equation for a sigmoidal dose-response with a variable slope. Y=Bottom+(Top−Bottom)/(1+10^((Log $IC_{50}$−X)*HillSlope)) where X is the logarithm of concentration and Y is the response. Compounds having an $IC_{50}$ of 1 μM or less are considered active.

The compounds of the invention were found to be inhibitors of one or more of FGFR1, FGFR2, and FGFR3 according to the above-described assay. $IC_{50}$ data is provided below in Table 1. The symbol "+" indicates an $IC_{50}$ less than 100 nM.

TABLE 1

| Example No. | FGFR1 IC50 (nM) | FGFR2 IC50 (nM) | FGFR3 IC50 (nM) |
|---|---|---|---|
| 1 | + | + | + |
| 2 | + | + | + |
| 3 | + | + | + |
| 4 | + | + | + |
| 5 | + | + | + |
| 6 | + | + | + |
| 7 | + | + | + |
| 8 | + | + | + |
| 9 | + | + | + |
| 10 | + | + | + |
| 11 | + | + | + |
| 12 | + | + | + |
| 13 | + | + | + |
| 14 | + | + | + |
| 15 | + | + | + |
| 16 | + | + | + |
| 17 | + | + | + |
| 18 | + | + | + |
| 19 | + | + | + |
| 20 | + | + | + |
| 21 | + | + | + |
| 22 | + | + | + |
| 23 | + | + | + |
| 24 | + | + | + |
| 25 | + | + | + |
| 26 | + | + | + |
| 27 | + | + | + |
| 28 | + | + | + |
| 29 | + | + | + |
| 30 | + | + | + |
| 31 | + | + | + |
| 32 | + | + | + |
| 33 | + | + | + |

TABLE 1-continued

| Example No. | FGFR1 IC50 (nM) | FGFR2 IC50 (nM) | FGFR3 IC50 (nM) |
|---|---|---|---|
| 34 | + | + | + |
| 35 | + | + | + |
| 36 | + | + | + |
| 37 | + | + | + |
| 38 | + | + | + |
| 39 | + | + | + |
| 40 | + | + | + |
| 41 | + | + | + |
| 42 | + | + | + |
| 43 | + | + | + |
| 44 | + | + | + |
| 45 | + | + | + |
| 46 | + | + | + |
| 47 | + | + | + |
| 48 | + | + | + |
| 49 | + | + | + |
| 50 | + | + | + |
| 51 | + | + | + |
| 52 | + | + | + |
| 53 | + | + | + |
| 54 | + | + | + |

Example B

FGFR Cell Proliferation/Survival Assays

The ability of the example compounds to inhibit the growth of cells dependent on FGFR signaling for survival can be measured using viability assays. A recombinant cell line over-expressing human FGFR3 was developed by stable transfection of the mouse pro-B BaF3 cells (obtained from the Deutsche Sammlung von Mikroorganismen and Zellkulturen) with a plasmid encoding the full length human FGFR3. Cells were sequentially selected for puromycin resistance and proliferation in the presence of heparin and FGF 1. A single cell clone was isolated and characterized for functional expression of FGFR3. This BaF3-FGFR3 clone is used in cell proliferation assays, and compounds are screened for their ability to inhibit cell proliferation/survival. The BaF3-FGFR3 cells are seeded into 96 well, black cell culture plates at 3500 cells/well in RPMI1640 media containing 2% FBS, 20 µg/mL Heparin and 5 ng/mL FGF1. The cells were treated with 10 µL of 10× concentrations of serially diluted compounds (diluted with medium lacking serum from 5 mM DSMO dots) to a final volume of 100 µL/well. After 72 hour incubation, 100 µL of Cell Titer Glo™ reagent (Promega Corporation) that measures cellular ATP levels is added to each well. After 20 minute incubation with shaking, the luminescence is read on a plate reader. The luminescent readings are converted to percent inhibition relative to DMSO treated control wells, and the $IC_{50}$ values are calculated using GraphPad Prism software by fitting the data to the equation for a sigmoidal dose-response with a variable slope. Compounds having an $IC_{50}$ of 10 µM or less are considered active. Cell lines representing a variety of tumor types including KMS-11 (multiple myeloma, FGFR3 translocation), RT112 (bladder cancer, FGFR3 overexpression), KatoIII (gastric cancer, FGFR2 gene amplification), and H-1581 (lung, FGFR1 gene amplification) are used in similar proliferation assays. In some experiments, MTS reagent, Cell Titer 96® AQueous One Solution Reagent (Promega Corporation) is added to a final concentration of 333 µg/mL in place Cell Titer Glo and read at 490/650 nm on a plate reader. Compounds having an $IC_{50}$ of 5 µM or less are considered active.

Example C

Cell-Based FGFR Phosphorylation Assays

The inhibitory effect of compounds on FGFR phosphorylation in relevant cell lines (BaF3-FGFR3, KMS-11, RT112, KatoIII, H-1581 cancer cell lines and HUVEC cell line) can be assessed using immunoassays specific for FGFR phosphorylation. Cells are starved in media with reduced serum (0.5%) and no FGF1 for 4 to 18 h depending upon the cell line then treated with various concentrations of individual inhibitors for 1-4 hours. For some cell lines, such as Ba/F3-FGFR3 and KMS-11, cells are stimulated with Heparin (20 µg/mL) and FGF1 (10 ng/mL) for 10 min. Whole cell protein extracts are prepared by incubation in lysis buffer with protease and phosphatase inhibitors [50 mM HEPES (pH 7.5), 150 mM NaCl, 1.5 mM $MgCl_2$, 10% Glycerol, 1% Triton X-100, 1 mM sodium orthovanadate, 1 mM sodium fluoride, aprotinin (2 µg/mL), leupeptin (2 µg/mL), pepstatin A (2 µg/mL), and phenylmethylsulfonyl fluoride (1 mM)] at 4° C. Protein extracts are cleared of cellular debris by centrifugation at 14,000×g for 10 minutes and quantified using the BCA (bicinchoninic acid) microplate assay reagent (Thermo Scientific).

Phosphorylation of FGFR receptor in protein extracts was determined using immunoassays including western blotting, enzyme-linked immunoassay (ELISA) or bead-based immunoassays (Luminex). For detection of phosphorylated FGFR2, a commercial ELISA kit DuoSet IC Human Phospho-FGF R2α ELISA assay (R&D Systems, Minneapolis, Minn.) can be used. For the assay KatoIII cells are plated in 0.2% FBS supplemented Iscove's medium (50,000 cells well per 100 µL) into 96-well flat-bottom tissue culture treated plates (Corning, Corning, N.Y.), in the presence or absence of a concentration range of test compounds and incubated for 4 hours at 37° C., 5% $CO_2$. The assay is stopped with addition of 200 µL of cold PBS and centrifugation. The washed cells are lysed in Cell Lysis Buffer (Cell Signaling, #9803) with Protease Inhibitor (Calbiochem, #535140) and PMSF (Sigma, #P7626) for 30 min on wet ice. Cell lysates were frozen at −80° C. before testing an aliquot with the DuoSet IC Human Phospho-FGF R2α ELISA assay kit. GraphPad prism3 was used to analyze the data. The $IC_{50}$ values were derived by fitting the data to the equation for a sigmoidal dose-response with a variable slope.

For detection of phosphorylated FGFR3, a bead based immunoassay was developed. An anti-human FGFR3 mouse mAb (R&D Systems, cat#MAB7661) was conjugated to Luminex MAGplex microspheres, bead region 20 and used as the capture antibody. RT-112 cells were seeded into multi-well tissue culture plates and cultured until 70% confluence. Cells were washed with PBS and starved in RPMI+0.5% FBS for 18 hr. The cells were treated with 10 µL of 10× concentrations of serially diluted compounds for 1 hr at 37° C., 5% $CO_2$ prior to stimulation with 10 ng/mL human FGF1 and 20 µg/mL Heparin for 10 min. Cells were washed with cold PBS and lysed with Cell Extraction Buffer (Invitrogen) and centrifuged. Clarified supernatants were frozen at −80° C. until analysis.

For the assay, cell lysates are diluted 1:10 in Assay Diluent and incubated with capture antibody-bound beads in a 96-well filter plate for 2 hours at room temperature on a plate shaker. Plates are washed three times using a vacuum manifold and incubated with anti-phospho-FGF R1-4 (Y653/Y654) rabbit polyclonal antibody (R&D Systems cat# AF3285) for 1 hour at RT with shaking Plates are washed three times. The diluted reporter antibody, goat anti-rabbit-RPE conjugated antibody (Invitrogen Cat. # LHB0002) is added and incubated for 30 minutes with shaking Plates are washed three times. The beads are suspended in wash buffer with shaking at room temperature for 5 minutes and then read on a Luminex 200 instrument set to count 50 events per sample, gate settings 7500-13500. Data is expressed as mean fluorescence intensity (MFI). MFI from compound treated samples are divided by MFI values from DMSO controls to determine the percent inhibition, and the $IC_{50}$ values are calculated using the GraphPad Prism software. Compounds having an $IC_{50}$ of 1 µM or less are considered active.

Example D

FGFR Cell-Based Signaling Assays

Activation of FGFR leads to phosphorylation of Erk proteins. Detection of pErk is monitored using the Cellu'Erk HTRF (Homogeneous Time Resolved Flurorescence) Assay (CisBio) according to the manufacturer's protocol. KMS-11 cells are seeded into 96-well plates at 40,000 cells/well in RPMI medium with 0.25% FBS and starved for 2 days. The medium is aspirated and cells are treated with 30 µL of 1× concentrations of serially diluted compounds (diluted with medium lacking serum from 5 mM DSMO dots) to a final volume of 30 µL/well and incubated for 45 min at room temperature. Cells are stimulated by addition of 10 µL of Heparin (100 µg/mL) and FGF1 (50 ng/mL) to each well and incubated for 10 min at room temperature. After lysis, an aliquot of cell extract is transferred into 384-well low volume plates, and 4 µL of detection reagents are added followed by incubation for 3 hr at room temperature. The plates are read on a PheraStar instrument with settings for HTRF. The normalized fluorescence readings are converted to percent inhibition relative to DMSO treated control wells, and the $IC_{50}$ values are calculated using the GraphPad Prism software. Compounds having an $IC_{50}$ of 1 µM or less are considered active.

Example E

VEGFR2 Kinase Assay

40 µL Enzyme reactions are run in black 384 well polystyrene plates for 1 hour at 25° C. Wells are dotted with 0.8 µL of test compound in DMSO. The assay buffer contains 50 mM Tris, pH 7.5, 0.01% Tween-20, 10 mM $MgCl_2$, 1 mM EGTA, 5 mM DTT, 0.5 µM Biotin-labeled EQEDEPEGDYFEWLE peptide substrate (SEQ ID NO: 1), 1 mM ATP, and 0.1 nM enzyme (Millipore catalogue number 14-630). Reactions are stopped by addition of 20 µL Stop Buffer (50 mM Tris, pH=7.8, 150 mM NaCl, 0.5 mg/mL BSA, 45 mM EDTA) with 225 nM LANCE Streptavidin Surelight® APC (PerkinElmer catalogue number CR130-100) and 4.5 nM LANCE Eu-W1024 anti phosphotyrosine (PY20) antibody (PerkinElmer catalogue number AD0067). After 20 minutes of incubation at room temperature, the plates are read on a PheraStar FS plate reader (BMG Labtech). $IC_{50}$ values can be calculated using GraphPad Prism by fitting the data to the equation for a sigmoidal dose-response with a variable slope. Compounds having an $IC_{50}$ of 1 µM or less are considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound which is: 2'-(2,6-difluoro-3,5-dimethoxyphenyl)-6'-[(2-morpholin-4-ylethyl)amino]-1',2'-dihydro-3'H-spiro[cyclopropane-1,4'-[2,4]naphthyridin]-3'-one or a pharmaceutically acceptable salt thereof.

2. A pharmaceutical composition comprising the compound of claim 1, or a pharmaceutically acceptable salt thereof, and at least one pharmaceutically acceptable carrier or excipient.

3. A compound which is 2'-(2,6-difluoro-3,5-dimethoxyphenyl)-6'-[(2-morpholin-4-ylethyl)amino]-1',2'-dihydro-3'H-spiro]cyclopropane-1,4'-[2,7]naphthyridin]-3'-one.

4. A pharmaceutical composition comprising the compound of claim 3 and at least one pharmaceutically acceptable carrier or excipient.

5. A pharmaceutically acceptable salt of 2'-(2,6-difluoro-3,5-dimethoxyphenyl) -6'-[(2-morpholin-4-ylethyl)amino]-1',2'-dihydro-3'H -spiro[cyclopropane-1,4'-[2,7]naphthyridin]-3'-one.

6. A pharmaceutical composition comprising the pharmaceutically acceptable salt of claim 5, and at least one pharmaceutically acccpetable carrier or excipient.

* * * * *

UNITED STATES PATENT AND TRADEMARK OFFICE
CERTIFICATE OF CORRECTION

PATENT NO. : 9,533,984 B2
APPLICATION NO. : 14/256438
DATED : January 3, 2017
INVENTOR(S) : Sun et al.

It is certified that error appears in the above-identified patent and that said Letters Patent is hereby corrected as shown below:

On the Title Page

Item (72) Inventor is corrected to read:
-- Yaping Sun, Hockessin, DE;
Liang Lu, Hockessin, DE;
Wenqing Yao, Chadds Ford, PA;
Chunhong He, Chadds Ford, PA;
Fenglei Zhang, Ambler, PA --.

In the Claims

Column 94, Line 44, in Claim 1, delete "A compound which is:
2'-(2,6-difluoro-3,5-dimethoxyphenyl)-6'-[(2-morpholin-4-ylethyl)amino]-1',2'-dihydro-3'*H*-spiro[cyclopropane-1,4'-[2,4]naphthyridin]-3'-one or a pharmaceutically acceptable salt thereof."
and insert -- A compound which is 2'-(2,6-difluoro-3,5-dimethoxyphenyl)-6'-[(2-morpholin-4-ylethyl)amino]-1',2'-dihydro-3'*H*-spiro[cyclopropane-1,4'-[2,7]naphthyridin]-3'-one or a pharmaceutically acceptable salt thereof. --.

Column 94, Line 53, in Claim 3, delete "A compound which is 2'-(2,6-difluoro-3,5-dimethoxyphenyl)-6'-[(2-morpholin-4-ylethyl)amino]-1',2'-dihydro-3'*H*-spiro]cyclopropane-1,4'-[2,7]naphthyridin]-3'-one." and insert -- A compound which is 2'-(2,6-difluoro-3,5-dimethoxyphenyl)-6'-[(2-morpholin-4-ylethyl)amino]-1',2'-dihydro-3'*H*-spiro[cyclopropane-1,4'-[2,7]naphthyridin]-3'-one. --.

Column 94, Line 60, in Claim 5, delete ") -6'-[" and insert -- )-6'-[ --.

Column 94, Line 61, in Claim 5, delete "3'H -spiro[" and insert -- 3'H-spiro[ --.

Column 94, Line 65, in Claim 6, delete "accceptable" and insert -- acceptable --.

Signed and Sealed this
Tenth Day of July, 2018

Andrei Iancu
*Director of the United States Patent and Trademark Office*